US011987787B2

(12) United States Patent
Doshi et al.

(10) Patent No.: US 11,987,787 B2
(45) Date of Patent: May 21, 2024

(54) DEVICES, METHODS, AND KITS FOR PREPARING A CELL SUSPENSION

(71) Applicant: AVITA MEDICAL AMERICAS, LLC, Valencia, CA (US)

(72) Inventors: Niraj Kumar Doshi, Valencia, CA (US); Navin Noel Bunyan, Valencia, CA (US); David Allen Fencil, Valencia, CA (US); Matthew Krywcun, Saugus, CA (US)

(73) Assignee: AVITA Medical Americas, LLC, Valencia, CA (US)

( * ) Notice: Subject to any disclaimer, the term of this patent is extended or adjusted under 35 U.S.C. 154(b) by 732 days.

(21) Appl. No.: 16/935,977

(22) Filed: Jul. 22, 2020

(65) Prior Publication Data

US 2022/0025317 A1 Jan. 27, 2022

(51) Int. Cl.
 *C12M 1/00* (2006.01)
 *B01L 3/00* (2006.01)
 *B01L 9/00* (2006.01)
 *C12M 1/33* (2006.01)
 *C12N 5/071* (2010.01)

(52) U.S. Cl.
 CPC ............. *C12M 45/22* (2013.01); *B01L 3/508* (2013.01); *B01L 3/52* (2013.01); *B01L 3/545* (2013.01); *B01L 9/00* (2013.01); *C12M 45/02* (2013.01); *C12M 45/09* (2013.01); *C12N 5/0625* (2013.01); *B01L 2200/16* (2013.01); *B01L 2200/18* (2013.01); *B01L 2300/021* (2013.01); *B01L 2300/025* (2013.01);

(Continued)

(58) Field of Classification Search
None
See application file for complete search history.

(56) References Cited

U.S. PATENT DOCUMENTS 4,595,102 A * 6/1986 Cianci ................... A61B 50/33
206/370
4,736,850 A * 4/1988 Bowman ............... A61F 2/0095
206/370

(Continued)

FOREIGN PATENT DOCUMENTS

EP 2828378 B1 11/2015
WO WO 2019/232504 A2 12/2019

(Continued)

*Primary Examiner* — P. Kathryn Wright
(74) *Attorney, Agent, or Firm* — Knobbe, Martens, Olson & Bear, LLP

(57) ABSTRACT

In some embodiments, a kit for preparing a cell suspension may include a device and a housing. The device may include a first label identifying a first reservoir of the device for use with a first portion of a tissue processing method and a second label identifying a second reservoir of the device for use with a second portion of the tissue processing method. The housing includes a first housing portion configured to store a first set of components associated with the first portion of the tissue processing method. The first housing portion includes a first visual indicator associated with the first label of the device. The second housing portion may be configured to store a second set of components associated with the second portion of the tissue processing method. The second housing portion may include a second visual indicator associated with the second label of the device.

27 Claims, 37 Drawing Sheets

(52) U.S. Cl.
CPC ....... *B01L 2300/16* (2013.01); *C12N 2509/00* (2013.01); *C12N 2509/10* (2013.01)

(56) References Cited

U.S. PATENT DOCUMENTS

| | | | |
|---|---|---|---|
| 5,012,929 | A | 5/1991 | Roosa |
| 5,100,621 | A * | 3/1992 | Berke ................... B01L 99/00 434/428 |
| 6,454,097 | B1 | 9/2002 | Blanco |
| 6,830,149 | B2 * | 12/2004 | Merboth .............. A01N 1/0263 206/461 |
| 6,861,250 | B1 | 3/2005 | Cole et al. |
| 7,155,306 | B2 | 12/2006 | Haitin et al. |
| 7,641,898 | B2 | 1/2010 | Lyles |
| 8,162,247 | B2 | 4/2012 | Faulker |
| 8,286,899 | B2 | 10/2012 | Schowalter et al. |
| 8,951,513 | B2 | 2/2015 | Alt et al. |
| 9,011,684 | B2 | 4/2015 | Kyle |
| 9,663,760 | B2 | 5/2017 | Taghizadeh et al. |
| 9,726,687 | B2 | 8/2017 | Murali et al. |
| 9,795,761 | B2 | 10/2017 | Lockwood et al. |
| 9,909,094 | B2 | 3/2018 | Cimino et al. |
| 9,926,530 | B2 | 3/2018 | Vacher et al. |
| 9,963,676 | B2 | 5/2018 | Broeckx et al. |
| 10,138,457 | B2 | 11/2018 | Cimino et al. |
| 10,626,370 | B2 | 4/2020 | Vacher et al. |
| 10,801,001 | B2 | 10/2020 | Brown et al. |
| 10,869,900 | B2 | 12/2020 | Funk |
| 2002/0106353 | A1 | 8/2002 | Wood et al. |
| 2015/0110750 | A1 | 4/2015 | Garza et al. |
| 2016/0024450 | A1 | 1/2016 | Quick et al. |
| 2016/0340651 | A1 | 11/2016 | Maslowski et al. |
| 2018/0280575 | A1 | 10/2018 | Delaney et al. |
| 2019/0001290 | A1 | 1/2019 | Fletcher |
| 2019/0031990 | A1 | 1/2019 | Timmins et al. |
| 2019/0071644 | A1 | 3/2019 | Chi et al. |
| 2019/0085283 | A1 | 3/2019 | Cimino et al. |
| 2019/0127681 | A1 | 5/2019 | Wurzer et al. |
| 2020/0033232 | A1 | 1/2020 | Lin et al. |
| 2020/0150005 | A1 | 5/2020 | Slutter et al. |
| 2020/0182757 | A1 | 6/2020 | Hamstrom et al. |
| 2020/0248117 | A1 | 8/2020 | Choi et al. |
| 2020/0305418 | A1 * | 10/2020 | Wu ...................... A01N 1/0284 |
| 2020/0352578 | A1 | 11/2020 | Torrie et al. |
| 2020/0352587 | A1 | 11/2020 | Davenport et al. |
| 2020/0354675 | A1 | 11/2020 | Vacher et al. |
| 2021/0085356 | A1 | 3/2021 | Knowlton |
| 2021/0102875 | A1 | 4/2021 | Levers et al. |
| 2021/0123838 | A1 | 4/2021 | Davenport et al. |
| 2021/0139840 | A1 | 5/2021 | Khalaj |
| 2021/0140856 | A1 | 5/2021 | Reis et al. |

FOREIGN PATENT DOCUMENTS

| | | |
|---|---|---|
| WO | WO 2020/230039 A1 | 11/2020 |
| WO | WO 2021/048441 A1 | 3/2021 |

\* cited by examiner

300

302
Identifying a first match between a first label disposed proximate a first reservoir of the device and a first visual indicator included in a first housing portion of the housing

304
In response to identifying the first match, removing a first set of components from the first housing portion and using the first set of components to perform a first portion of a tissue processing method associated with the first reservoir

306
Identifying a second match between a second label disposed proximate a second reservoir of the device and a second visual indicator included in a second housing portion of the housing

308
In response to identifying the second match, removing a second set of components from the second housing portion and using the second set of components to perform a second portion of the tissue processing method associated with the second reservoir

FIG. 3

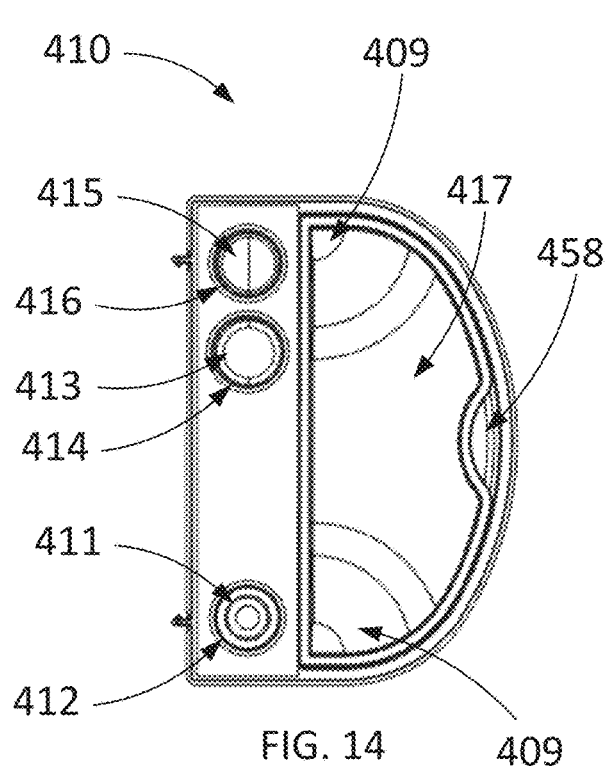
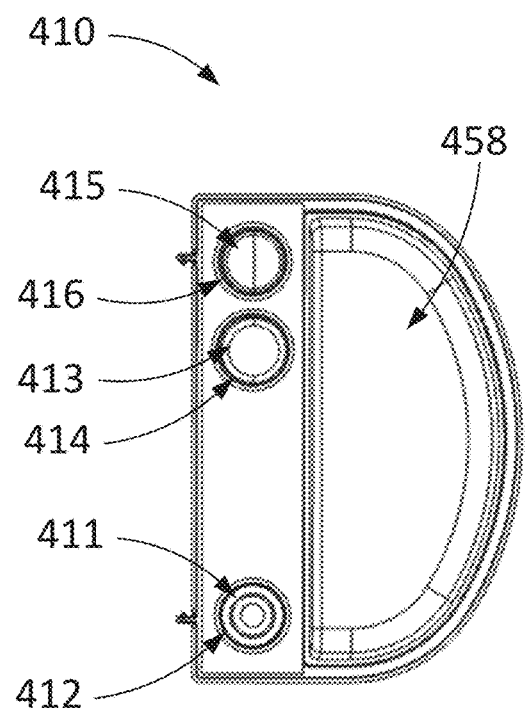
FIG. 14  FIG. 15
FIG. 16

DEVICES, METHODS, AND KITS FOR PREPARING A CELL SUSPENSION

TECHNICAL FIELD

This invention relates generally to the field of devices, methods, and kits for processing tissue, such as for preparation of a cell suspension.

BACKGROUND

Application of a cell suspension to a patient tissue treatment site may serve as an effective treatment for skin conditions such as wounds (e.g., burns, chronic wounds), pigmentation disorders, etc. Current approaches for preparing and applying a cell suspension to a skin surface, however, may be vulnerable to user error and inefficiencies due to, for example, the number of similar tools and overall number of components required to complete the operational steps. Thus, a need for improved cell suspension preparation techniques and equipment exists.

SUMMARY

In some embodiments, a kit for preparing a cell suspension may include a device and a housing. The device may define a first reservoir and a second reservoir. The device may include a first label identifying the first reservoir for use with a first portion of a tissue processing method and a second label identifying the second reservoir for use with a second portion of the tissue processing method. The housing may be configured to receive the device. The housing may include a first housing portion configured to store a first set of components associated with the first portion of the tissue processing method. The first housing portion may include a first visual indicator associated with the first label of the device. The second housing portion may be configured to store a second set of components associated with the second portion of the tissue processing method. The second housing portion may include a second visual indicator associated with the second label of the device.

In some embodiments, a packaging system for a device for preparing a cell suspension may include a first housing portion and a second housing portion. The device may include a first reservoir having a first label and a second reservoir having a second label. The first housing portion may include a set of recesses configured to receive a first set of components associated with a first portion of a tissue processing method. The first housing portion may include a first visual indicator associated with the first label of the device. The second housing portion may include a set of recesses configured to receive a second set of components associated with a second portion of the tissue processing method. The second housing portion may include a second visual indicator associated with the second label of the device.

In some embodiments, a method for preparing a cell suspension using a device packaged in a housing may include identifying a first match between a first label disposed proximate a first reservoir of the device and a first visual indicator included in a first housing portion of the housing. In response to identifying the first match, a first set of components may be removed from the first housing portion and the first set of components may be used to perform a first portion of a tissue processing method associated with the first reservoir. A second match between a second label disposed proximate a second reservoir of the device and a second visual indicator included in a second housing portion of the housing may be identified. In response to identifying the second match, a second set of components from the second housing portion may be removed and used, where the second set of components may be used to perform a second portion of the tissue processing method associated with the second reservoir.

BRIEF DESCRIPTION OF THE DRAWINGS

FIG. 3 is flow diagram of a method for preparing a cell suspension using a device packaged in a housing, in accordance with some embodiments.

FIGS. 4-24 are various views of the components of a kit for preparing a cell suspension, according to an embodiment.

DETAILED DESCRIPTION

Figure 1:
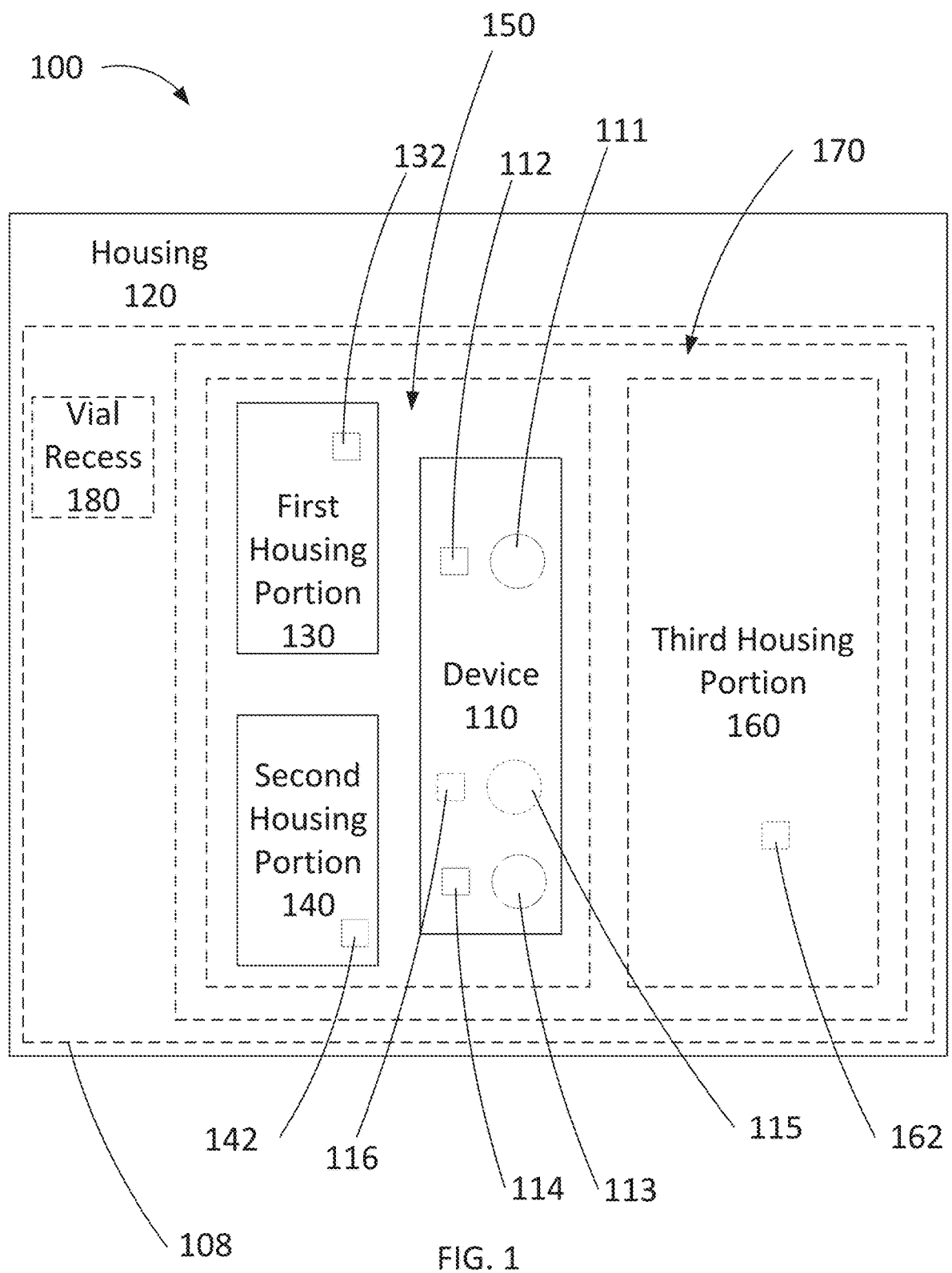
FIG. 1 is a schematic block diagram of a kit for preparing a cell suspension, according to an embodiment.

In some embodiments, a kit for preparing a cell suspension may include a device and a housing. The housing may, for example, function as device packaging for storage and/or transport of the device. The device may define one or more reservoirs for use with a tissue processing method. For example, the device may define a first reservoir and a second reservoir. The device may include a first label identifying the first reservoir for use with a first portion of a tissue processing method and a second label identifying the second reservoir for use with a second portion of the tissue processing method. The housing may be configured to receive the device. The housing may include a first housing portion configured to store a first set of components associated with the first portion of the tissue processing method. The first housing portion may include a first visual indicator associated with the first label of the device. The second housing portion may be configured to store a second set of components associated with the second portion of the tissue processing method. The second housing portion may include a second visual indicator associated with the second label of the device. Thus, in some embodiments, the first housing portion may be identified as including a first set of components associated with the first reservoir of the device, where the first set of components and the first reservoir of the device may be used in the first portion of the tissue processing method. Similarly, in some embodiments, the second housing portion may be identified as including a second set of components associated with the second reservoir of the device, where the second set of components and the second reservoir of the device may be used in the second portion of the tissue processing method. Any suitable number (e.g., three, four, or more) of housing portions and respective reservoirs may be identified and labeled in a similar manner associated with other portions of the tissue processing method. It should also be understood that in some embodiments, non-reservoir device features (e.g., surfaces) may additionally or alternatively be labeled in a similar manner associated with one or more housing portions via corresponding labels and visual indicators.

In some embodiments, a packaging system for a device for preparing a cell suspension may include a first housing portion and a second housing portion. The device may include a first reservoir having a first label and a second reservoir having a second label. The first housing portion may define a set of one or more recesses configured to receive a first set of one or more components associated with a first portion of a tissue processing method. The first housing portion may include a first visual indicator associated with the first label of the device (e.g., thereby identifying the first housing portion as including components associated with the first reservoir of the device, where such first set of components and first reservoir of the device may be used in the first portion of the tissue processing method). The second housing portion may define a set of one or more recesses configured to receive a second set of one or more components associated with a second portion of the tissue processing method. The second housing portion may include a second visual indicator associated with the second label of the device (e.g., thereby identifying the second housing portion as including components associated with the second reservoir of the device, where such second set of components and second reservoir of the device may be used in the second portion of the tissue processing method). Any suitable number of housing portions (e.g., three, four, or more) and respective reservoirs may be identified and labeled in a similar manner associated with other portions of the tissue processing method. It should also be understood that in some embodiments, non-reservoir device features (e.g., surfaces) may additionally or alternatively be labeled in a similar manner associated with one or more housing portions via corresponding labels and visual indicators.

In some embodiments, a method for preparing a cell suspension using a device packaged in a housing includes identifying a first match between a first label disposed proximate a first reservoir of the device and a first visual indicator included in a first housing portion of the housing. In response to identifying the first match, a first set of components may be removed from the first housing portion and the first set of components may be used to perform a first portion of a tissue processing method associated with the first reservoir. A second match between a second label disposed proximate a second reservoir of the device and a second visual indicator included in a second housing portion of the housing may be identified. In response to identifying the second match, a second set of components from the second housing portion may be removed and used the second set of components may be used to perform a second portion of the tissue processing method associated with the second reservoir. In some embodiments, the method may include identifying matches between any suitable number of housing portions (e.g., three, four or more) and respective reservoirs and similarly removing and using components from these housing portions for use in other portions of the tissue processing method. It should also be understood that in some embodiments, non-reservoir device features (e.g., surfaces) may additionally or alternatively be labeled in a similar manner associated with one or more housing portions via corresponding labels and visual indicators.

Kits and Devices for Cell Suspension

FIG. 1 is a schematic illustration of a kit 100 for preparing a cell suspension. The kit 100 includes a device 110 and a housing 120. The device 110 may also be referred to as a processing unit. Generally, the device 110 may include features (e.g., reservoirs, preparation tray for tissue manipulation, etc.), as further described below, for use in a tissue processing method (e.g., for preparing a cell suspension), while the housing 120 may function as packaging for the device 110 and/or various components (e.g., tools) for use in a tissue processing method involving the device 110. Additional example features of the housing and device are described in further detail below.

For example, the device 110 may include a first reservoir 111 and a second reservoir 113. The device 110 may include a first label 112 identifying the first reservoir 111 for use with a first portion of a tissue processing method and a second label 114 identifying the second reservoir 113 for use with a second portion of a tissue processing method.

The housing 120 may be configured to receive the device 110. The housing 120 may include a first housing portion 130 and a second housing portion 140. The first housing portion 130 may be configured to store a first set of components associated with the first portion of the tissue processing method. The second housing portion 140 may be configured to store a second set of components associated with the second portion of the tissue processing method. The first housing portion 130 may include a first visual indicator 132 associated with the first label 112 of the device. The second housing portion 140 may include a second visual indicator 142 associated with the second label 114 of the device. One or both of the first and second housing portions may include recesses each sized and shaped to receive a specific kind of component (e.g., tool) for use in the tissue processing method.

In some implementations, the first housing portion 130 and the second housing portion 140 may be integrally formed as portions of an integrated tray portion 150. In some implementations, the housing 120 may include an integrated tray portion 150 configured to removably receive the first housing portion 130 and the second housing portion 140, which may be integrally formed with each other or may be distinct tray portions. The integrated tray portion 150 may define one or more recesses configured to receive the first housing portion 130 and/or the second housing portion 140. In some implementations, the integrated tray portion 150 may also define a recess configured to receive the device 110.

In some implementations, the first housing portion 130 and the second housing portion 140 may be removably coupled to each other. For example, in some embodiments the housing portion 130 and the second housing 140 may be coupled to each other via a perforated connecting portion such that the first housing portion 130 may be separated from the second housing portion 140 via separating (e.g., tearing) the perforations. As another example, in some embodiments the housing portion 130 and the second housing 140 may be coupled to each other via one or more fasteners (e.g., adhesive, mechanical fasteners, etc.) and/or mating or interlocking features (e.g., the first housing portion 130 may include a first mating feature and the second housing portion 140 may including a second mating feature, where the first and second mating features are snap fit or otherwise removably coupled to one another).

In some implementations, the housing 120 may include a third housing portion 160. The device 110 may define a third reservoir 115 and may include a third label 116 identifying the third reservoir 115 for use with a third portion of a tissue processing method. The third housing portion 160 is configured to store a third set of components associated with the third portion of the tissue processing method. For example, in some implementations, the third housing portion 160 may define a recess for each component of the third set of components. In some implementations, the third housing portion 160 may define a recess for each type of component of the third set of components (e.g., a single recess may be configured to receive a subset of common or identical components). The third housing portion 160 may include a third visual indicator 162 associated with the third label 116 of the device. In some implementations, the third housing portion 160 may be removably coupled to the first housing portion 130 and/or the second housing portion 140 (e.g., via a perforated connecting portion such that the third housing portion 160 may be separated from the first housing portion 130 and/or the second housing portion 140 via separating (e.g., tearing) the perforations, and/or via one or more fasteners, mating, or interlocking features as described above with respect the first and second housing portions). It should be understood that in some embodiments, the housing 120 may include any other suitable number of housing portions (e.g., two, three, four, five, or more), with respective visual indicators corresponding to respective labels of device features for use with respective portions of a tissue processing method.

In some implementations, the housing 120 may include a base 170 configured to receive various housing portions, such as the first housing portion 130, the second housing portion 140, and the third housing portion 160 as shown in FIG. 1. The base 170 may be configured to receive the device 110 in addition to the first housing portion 130, the second housing portion 140, and the third housing portion 160. In some implementations, the base 170 may be configured to receive the integrated tray portion 150 (e.g., the integrated tray portion 150 containing the first housing portion 130, the second housing portion 140, and the device 110) and the third housing portion 160. For example, the base 170 may define a first recess configured to receive the integrated tray portion 150 and a second recess configured to receive the third housing portion 160. Accordingly, in some embodiments, each of the integrated tray portion 150 (with the first housing portion 130, second housing portion 140, and device 110) and the third housing portion 160 may be individually removed from the base 170, such as to enable a user to easily and efficiently remove the integrated tray portion 150 and device 110 from the base and set them aside in an area that is separate from the third housing portion 160.

In some implementations, the housing 120 may include a box 108 or other suitable enclosure within which the base 170 may be disposed (e.g., the base 170 containing the integrated tray portion 150 and the third housing portion 160). The box 108 may, for example, including cardboard that is folded and/or otherwise secured into a suitable enclosure that partially or entirely surrounds the rest of the housing 120 (e.g., trays, etc.). In some implementations, the box 108 (or box insert arranged therein) may define a vial recess 180. The vial recess 180 may be located in a pull-out tab, insert, or other structure, and may be configured to receive a vial containing an enzyme (e.g., an enzyme vial disposed in a sterile pouch). The enzyme may, for example, be suitable for chemically disaggregating tissue, as described in further detail below. In some implementations, the housing 120 may include a divider separating the vial recess 180 from the first housing portion 130, the second housing portion 140, the device 110, and the optional third housing portion 160. For example, the divider may separate the vial recess 180 from the base 170. The vial recess 180 may, for example, enable sterilization of the enzyme vial that is separate from sterilization of the rest of the housing 120 (or at least sterilization of the device 110). Accordingly, different sterilization processes may be used for the enzyme vial and the rest of the housing 120 (e.g., device 110). Such separate sterilization processes may, for example, help avoid damage or other compromise of either the enzyme or the device 110. For example, in some embodiments the enzyme may be at risk of compromise if it undergoes ethylene oxide sterilization, while the device 110 (which may include a processor and/or other electronics) may be at risk of compromise if it undergoes gamma radiation sterilization. Accordingly, the enzyme vial and the device 110 may each undergo a respective sterilization process that decreases risk of compromise to the sterilized component. For example, a portion of the housing 120 including electronics (e.g., in device 110) may be sterilized with a first sterilization process (e.g., with ethylene oxide), while the enzyme vial may be separately sterilized with a second sterilization process (e.g., with gamma radiation) before being inserted into the vial recess 180 of the housing 120. In some embodiments, the sterilized enzyme vial may be placed into a sterile pouch prior to being placed in the vial recess 180. Before or as an early step of the first portion of the tissue processing method, the enzyme vial within the sterile pouch may then be removed from the vial recess 180, the enzyme vial may be removed from the sterile pouch, and the enzyme vial may be disposed within an enzyme vial recess defined in the first housing portion 130 such that the enzyme vial may be transported with the first set of components within the first housing portion 130 (e.g., to a workspace near or within the sterile field).

In some implementations, the device 110 may include any suitable features or components such that the device 110 may be used to perform a tissue processing method. For example, the device 110 may include a skin tissue manipulation area surrounded by sidewalls. The skin tissue manipulation area may optionally include a textured surface region. In some implementations, the device 110 may include a preparation tray to be used to perform at least a portion of the tissue processing method (e.g., to be used during the second portion and/or the third portion of the tissue processing method). The preparation tray may be an insert tray removable from a complementary recessed area of the device 110 (e.g., lifted out, removed from a slot, etc.). Alternatively, in some embodiments, the preparation tray may be integrally formed with the device 110, such as integrally formed as a region within a base structure of the device 110. Furthermore, in some embodiments, the preparation tray may be removably coupled to the device 110, such as with one or more snap-off connector pieces, perforations, disengaging mating features, an adhesive (e.g., tape) that may be removed, etc. In some implementations, the preparation tray may include the skin tissue manipulation area and the surrounding sidewalls. In some implementations, the preparation tray may include one or more collection areas disposed relative to other portions of a bottom surface of the preparation tray including the skin tissue manipulation area such that fluid flows from the skin tissue manipulation area of the preparation tray toward and/or into the collection area.

In some implementations, the skin tissue manipulation area may be a smooth, flat surface. In some implementations, the skin tissue manipulation area may include or define one or more dimples, ridges, ramps, inclines, or pathways (e.g., a spout) toward a collection area (e.g., a collection area including a filter) or the third reservoir 115. In some implementations, at least a portion of the preparation tray (e.g., the skin tissue manipulation area) may be at least partially formed of an antimicrobial material (e.g., by impregnating the skin tissue manipulation area surface via plastic injection molding). Additionally or alternatively, at least a portion of the preparation tray (e.g., the skin tissue manipulation area) may include an antimicrobial coating applied to the surface of the preparation tray. For example, the preparation tray may include one or more antimicrobial drugs such as sulfonamide drugs, trimethoprim, quinolones, and/or nitrofuranes, etc. As another example, the preparation tray may additionally or alternatively include antimicrobial nanotechnology or other antimicrobial technology (e.g., silver nanoparticles, phenols, polybiguanides (e.g., polyhexamethylene biguanide (PHMB)), chitosan, and/or halamines (e.g., N-halamines)). As another example, the preparation tray may include one or more antibiotics (e.g., minocycline, rifampin, vancomycin, silver sulfadiazine, ceftazidime implants, gentamicin implants, etc.), such as in a coating, attached via bond (e.g., covalent bond, ionic bond), and/or in a matrix. As another example, the preparation tray may additionally or alternatively include one or more other suitable antibacterial or other antimicrobial coatings or substances (e.g., organosiloxanes). As another example, the preparation tray may additionally or alternatively include one or more antiseptics (e.g., chlorhexidine) through impregnation and/or as a coating. Furthermore, the preparation tray may additionally or alternatively include one or more noble metals (e.g., silver salts, ions, complexes, and/or nanostructured silver, gold, copper, or palladium, etc.), such as incorporated in the material of the preparation tray and/or as a coating. Additionally or alternatively, the preparation tray may include one or more non-antibiotic substances (through impregnation and/or as a coating) such as methylene blue and/or phenothiazine, which functions to operate synergistically with one or more antibiotics or other antimicrobial substances.

In some implementations, the device 110 may include a heating assembly configured to heat the contents of the first reservoir 111. The heating assembly may include any suitable heating mechanism, energy storage device, indicator lights (e.g., LEDs), one or more activation buttons, and/or associated electronics. For example, the heating assembly may be configured to be activated via pressing a button of the heating assembly. The heating assembly may be configured to illuminate a first indicator light during a first time period when the heating mechanism is heating to a target temperature or target temperature range. In some implementations, the heating assembly my illuminate a second indicator light during a second time period when the heating mechanism is operating at the target temperature or within a target temperature range. In some implementations, the heating assembly may illuminate a second indicator light during a time period when the first reservoir 111 and/or the contents of the first reservoir 111 are at the target temperature or within a target temperature range. In some implementations, the heating assembly may illuminate the first indicator light to indicate that the heating mechanism is actively operating to maintain the contents of the first reservoir 111 at the target temperature or within the target range such that the first indicator light may turn on and off periodically or intermittently. The heating assembly may be configured to maintain a temperature of the first reservoir 111 for a first time period (e.g., fifteen, twenty, or sixty minutes). After the first time period, the heating assembly may be configured to continue maintaining the temperature at the target temperature or in the target range for a second time period (e.g., fifteen minutes). In some implementations, the heating assembly may include an alarm (e.g., an audible alarm) configured to provide an audible indication at periodic intervals during the second time period (e.g., once each minute). In some implementations, after the first time period or the second time period, the heating assembly may automatically cease operating to provide heat to the first reservoir 111.

In some implementations, the first set of components may include a vial containing a volume of water (e.g., sterile water), a needle, and/or an enzyme syringe. For example, the syringe may be a 10 ml syringe or any suitable capacity. The needle may be configured to be coupled to the syringe (e.g., snap fit, threads, other suitable fasteners, etc.). In some implementations, the first set of components may include a cell strainer. In some implementations, the first set of components may include an enzyme vial. The first housing portion 130 may define a recess associated with each component of the first set of components that is shaped to complement the shape of each component of the first set of components.

In some implementations, the second set of components may include a buffer vial, a needle, and/or a buffer syringe. In some implementations, the second set of components may include a first buffer vial, a second buffer vial, a needle, a first syringe (e.g., a syringe intended for transferring buffer), a second syringe (e.g., a syringe intended for transferring unfiltered suspension), and two surgical scalpels. The first syringe and the second end may each be, for example, 10 ml syringes or any suitable capacity. The fill needle may be, for example, a blunt fill needle. The surgical scalpels may be disposable. The first buffer vial may include, for example, 10 ml of buffer or any suitable volume. The second buffer vial may include, for example, 30 ml of buffer or any suitable volume. The second housing portion 140 may define a recess associated with each component or subset of identical components of the second set of components that is shaped to complement the shape of each component or subset of identical components of the second set of components.

In some implementations, the third set of components may include a buffer vial, a cell strainer, a set of skin cell syringes, a set of needles, an unfiltered suspension syringe, a set of spray nozzles, and a pair of scalpels. For example, the set of skin cell syringes may include four skin cell syringes (e.g., 10 ml syringes). The set of needles may include four needles (e.g., blunt fill needles) or any suitable number of needles. The set of spray nozzles may include four spray nozzles. Each skin cell syringe may be coupled to a needle of the set of needles or, alternatively, a spray nozzle of the set of spray nozzles (e.g., single-handedly). The buffer vial may include, for example, 30 ml of buffer or other suitable volume. In some implementations, the third set of components may include a set of skin cell syringes, a set of needles, and a set of spray nozzles. The third housing portion 160 may define a recess associated with each component or subset of identical components of the second set of components that is shaped to complement the shape of each component or subset of identical components of the second set of components.

The visual indicators in the housing 120 and the labels of features of the device 110 may correspond in any suitable manner. In some implementations, the first label 112 and the first visual indicator 132 both include the same alphanumeric character, such as "A" (e.g., A, B, C, 1, 2, 3, etc.). In some implementations, the first label 112 and the first visual indicator 132 may additionally or alternatively both include the same color such as blue (e.g., red, orange, yellow, green, blue, violet, etc.). In some implementations, the first label 112 and the first visual indicator 132 may additionally or alternatively both include the same symbol, such as a geometrical symbol (e.g., circle, ellipse, triangle, square, rectangle, etc.), punctuation, or other unique symbol (e.g., wavy line, zig-zag line, etc.). In some implementations, the first label 112 and the first visual indicator 132 both include the same combination of a letter, a color, a number, and/or a symbol.

Similarly, in some implementations, the second label 114 and the second visual indicator 142 may include the same alphanumeric character, color, and/or symbol, similar to that described above for the first label 112 and the first visual indicator 132. For example, the second label 114 and the second visual indicator 142 may both include the same alphanumeric character (e.g., B). In some implementations, the second label 114 and the second visual indicator 142 may both include the same color (e.g., grey). In some implementations, the second label 114 and the second visual indicator 142 both include the same symbol. In some implementations, the second label 114 and the second visual indicator 142 both include the same combination of a letter, a color, a number, and/or a symbol (e.g., different from the common letter, color, number, or symbol of the first label 112 and the first visual indicator 132).

Similarly, in some implementations, the third label 116 and the third visual indicator 162 may include the same alphanumeric character, color, and/or symbol, similar to that described above for the first label 12 and the first indicator 132. For example, the third label 116 and the third visual indicator 162 may both include the same alphanumeric character (e.g., C). In some implementations, the third label 116 and the third visual indicator 162 may both include the same color (e.g., green). In some implementations, the third label 116 and the third visual indicator 162 may both include the same number (e.g., 3). In some implementations, the third label 116 and the third visual indicator 162 may both include the same symbol. In some implementations, the third label 116 and the third visual indicator 162 may both include the same combination of a letter, a color, a number, and/or a symbol (e.g., different from the common letter, color, number, or symbol of the first label 112 and the first visual indicator 132 and different from the common letter, color, number, or symbol of the second label 114 and the second visual indicator 142).

It should be understood that any of the visual indicators described herein may have other suitable forms, such as textural features or patterning (e.g., bumps, wells, ribs, recesses, etc.) that uniquely identify the housing portions (and components contained therein) as corresponding to respective features of the device 110 (e.g., respective features labeled in a similar manner as the corresponding housing portions) and/or respective portions of the method for processing tissue. Additionally or alternatively, some or all of the components contained in the housing portions may be individually identified as corresponding to respective features of the device 110 and/or respective portions of the method for processing tissue. For example, some or all of the components may include handles that are labeled in a similar manner as described above for the housing portions (e.g., with visual indicators that are alphanumeric, color, symbolic, textural, etc.).

In some embodiments, at least a portion of the housing 120 (e.g., housing portions including recesses) may be formed at least in part through injection molding, or other suitable process such as milling, 3D printing, folding, etc. At least a portion of the housing 120 may include a suitable rigid or semi-rigid material (e.g., plastic, metal, cardboard, etc.). For example, the first housing portion 130, the second housing portion 140, the optional third housing portion 160, the optional integrated tray portion 150, the optional base 170, and the optional box 108 may each be formed of any suitable material. For example, the first housing portion 130, the second housing portion 140, and the third housing portion 160 may each be formed of plastic (e.g., translucent or transparent plastic). The integrated tray portion 150 and the base 170 may each be formed of plastic (e.g., translucent plastic). The box 108 may be formed of cardboard or other suitable rigid or semi-rigid material. In some implementations, one or more components of the kit 100 may be sterilized via a single method of sterilization (e.g., via ethylene oxide sterilization).

Figure 60A:
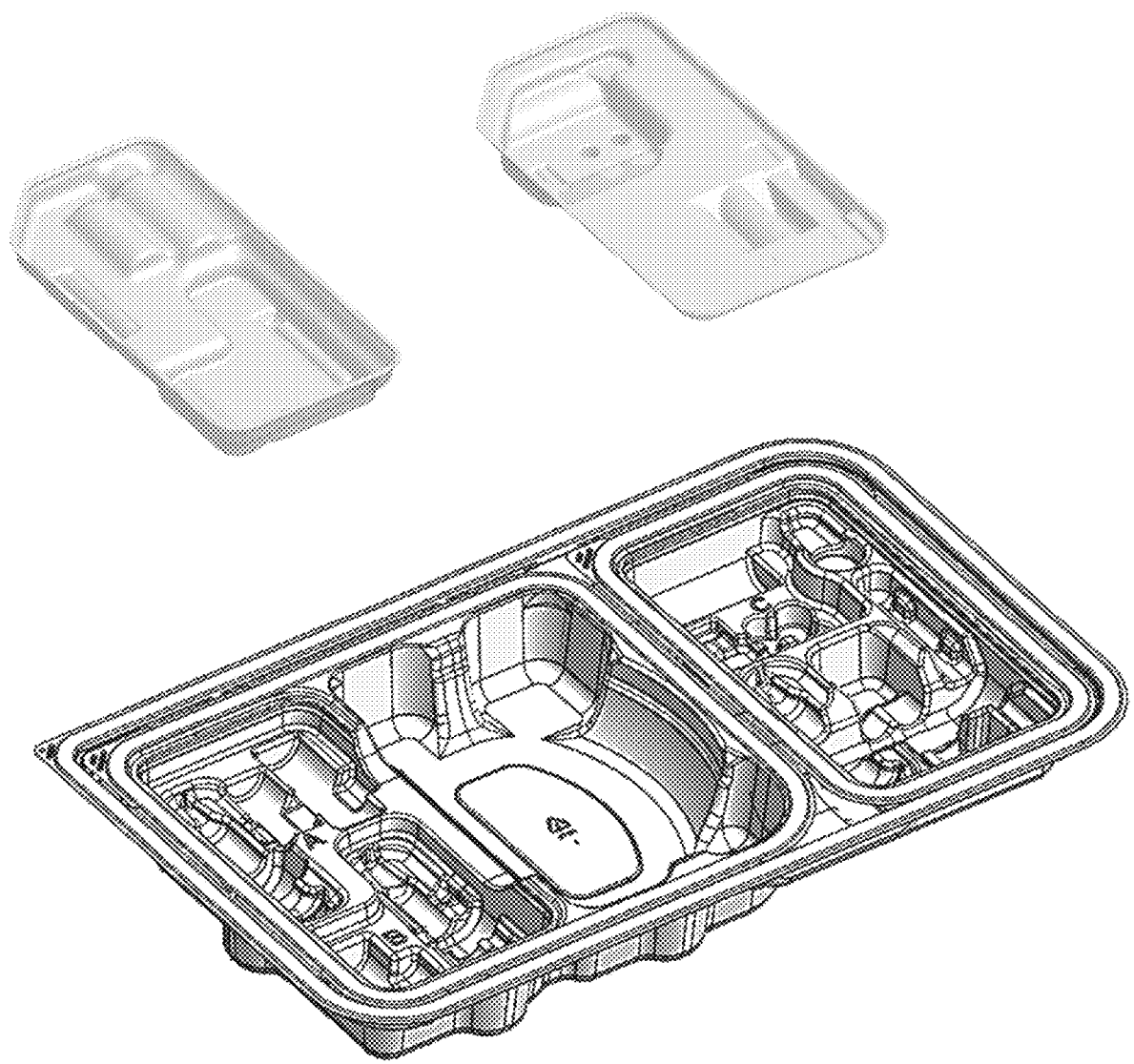
FIGS. 60A and 60B are an exploded view (with housing liners) and a top plan view (without housing liners), respectively, of a housing in a kit for preparing a cell suspension, according to an embodiment.
Figure 60B:
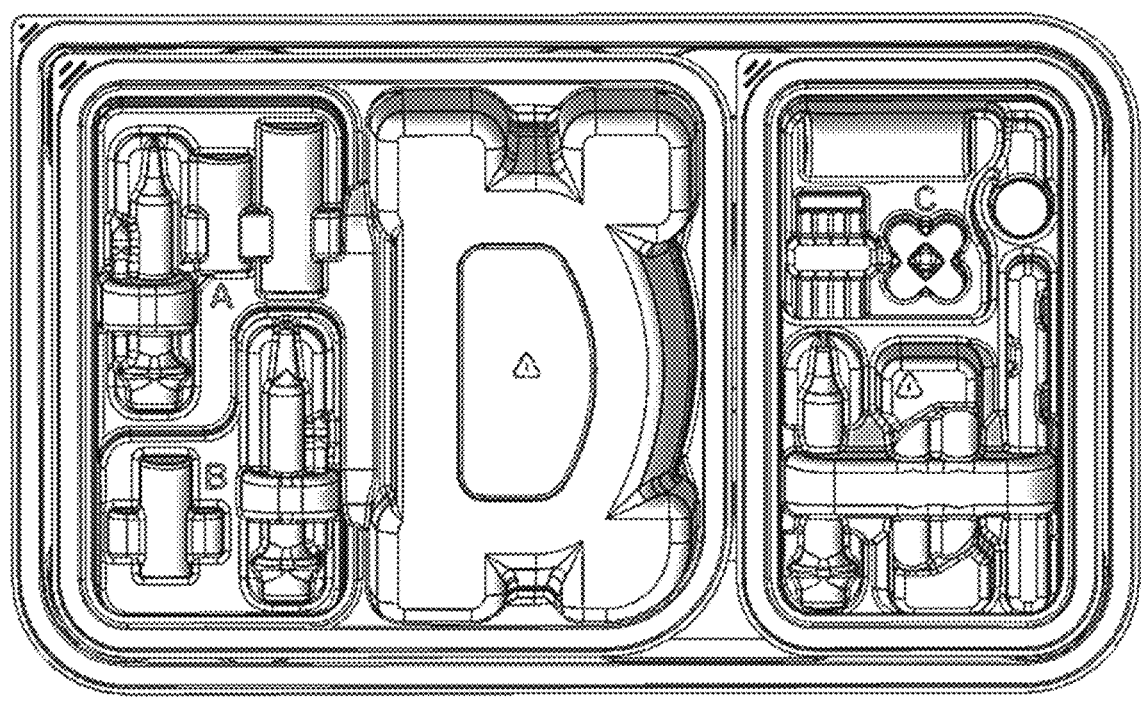
Figure 61A:
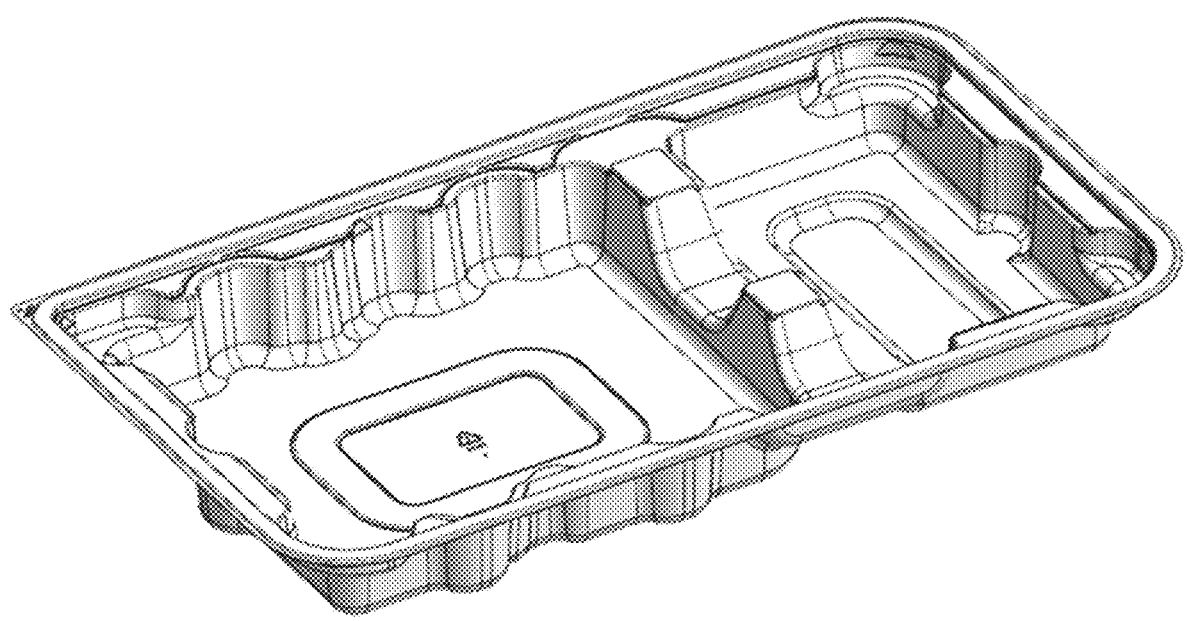
FIGS. 61A-61G are a perspective view, a rear view, a top plan review, a front view, a bottom view, a left view, and a right view, respectively, of a base in a kit for preparing and/or supplying a cell suspension, according to an embodiment.
Figure 61B:
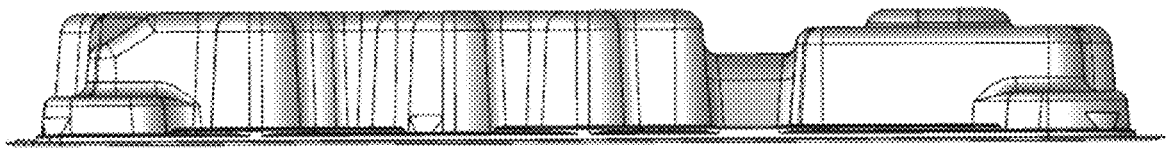
Figure 61C:
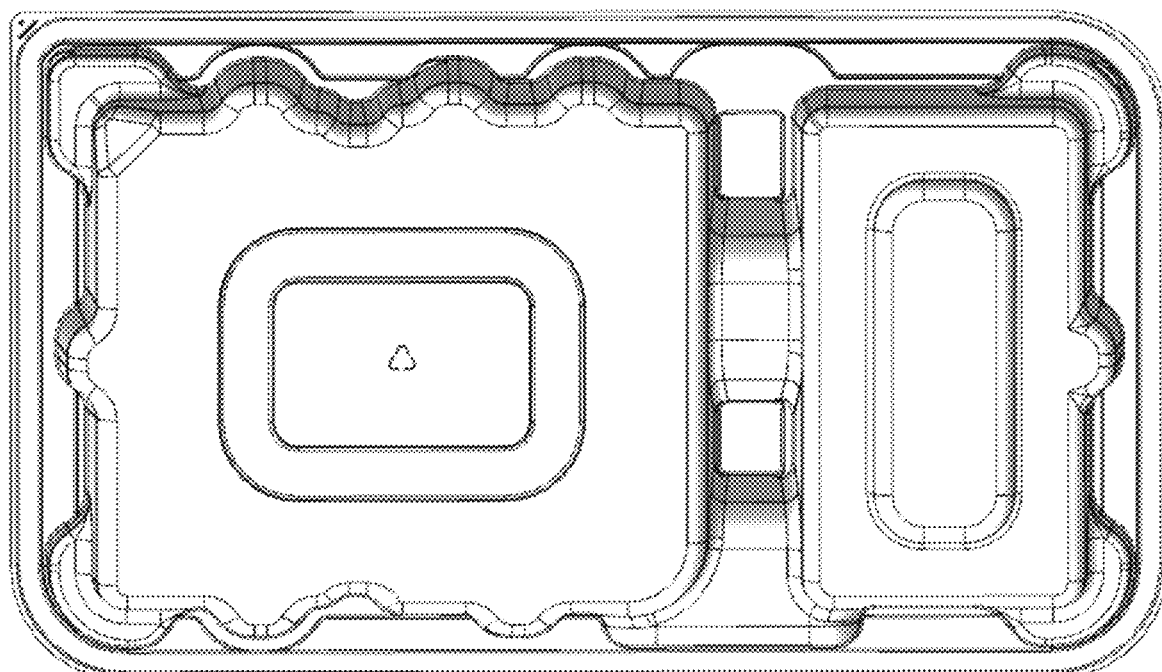
Figure 61D:
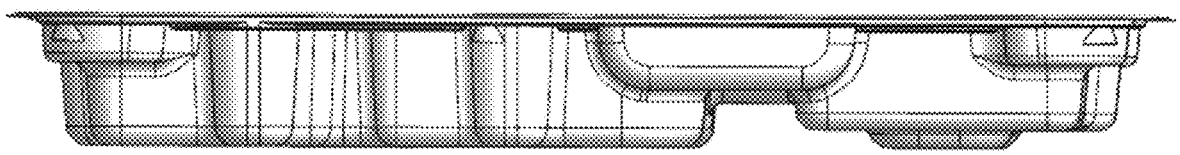
Figure 61E:
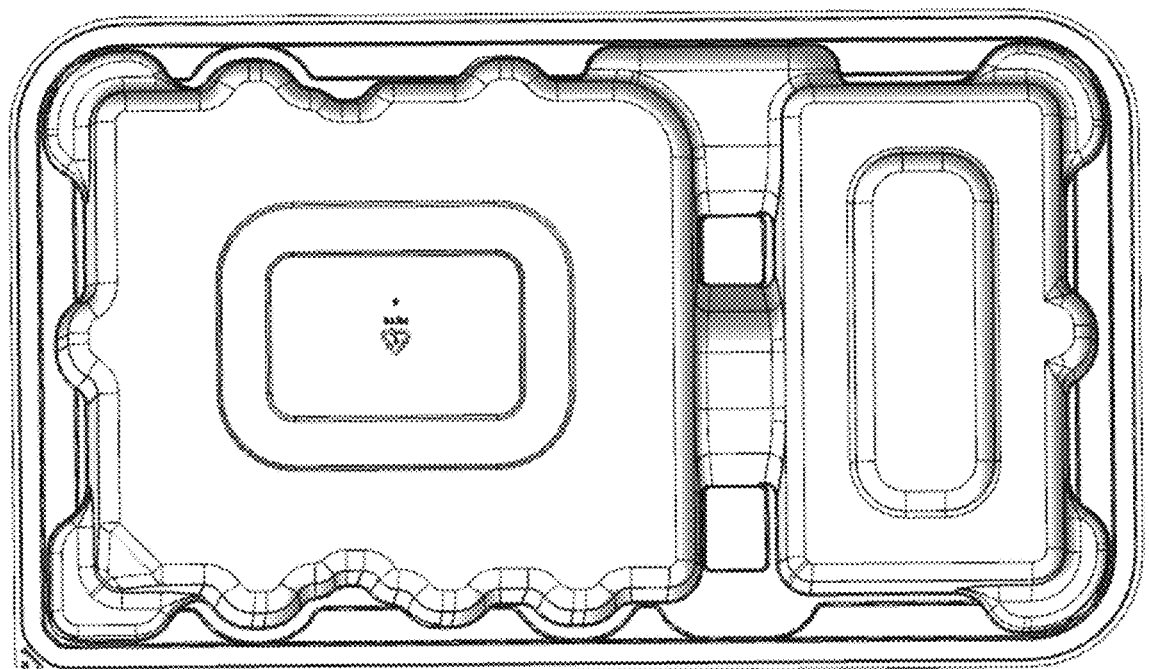
Figure 61F:
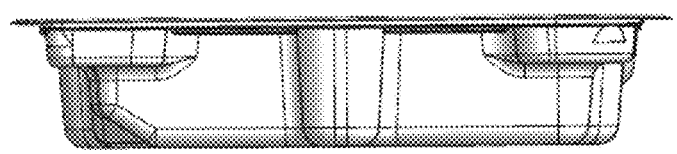
Figure 61G:
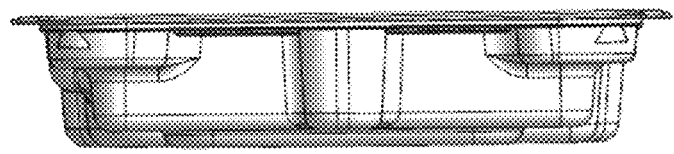
Figure 62A:
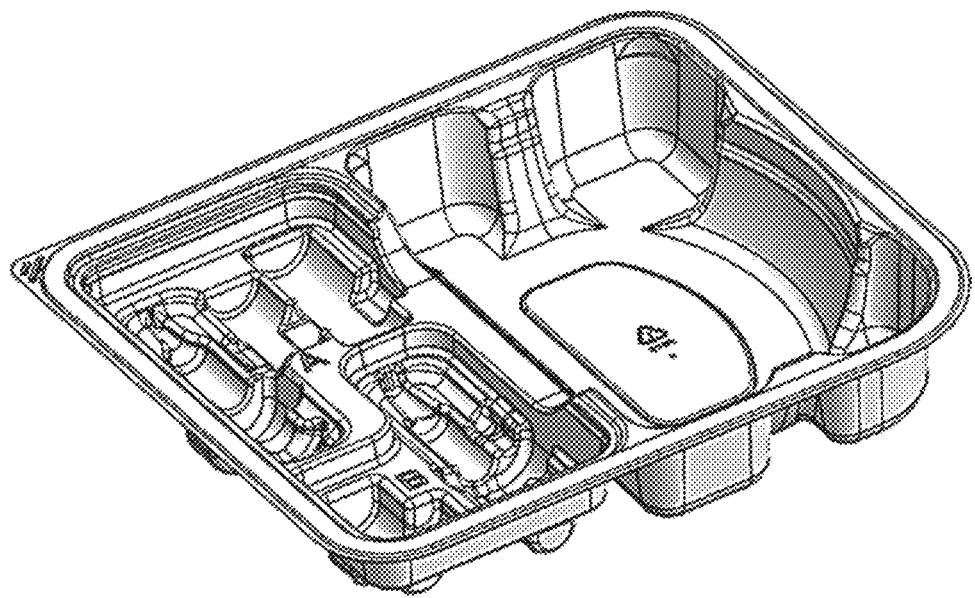
FIGS. 62A-62G are a perspective view, a rear view, a top plan review, a front view, a bottom view, a left view, and a right view, respectively, of an integrated tray portion in a kit for preparing and/or supplying a cell suspension, according to an embodiment.
Figure 62B:
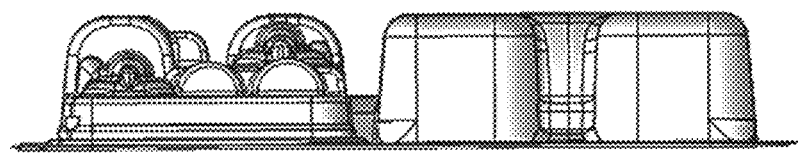
Figure 62C:
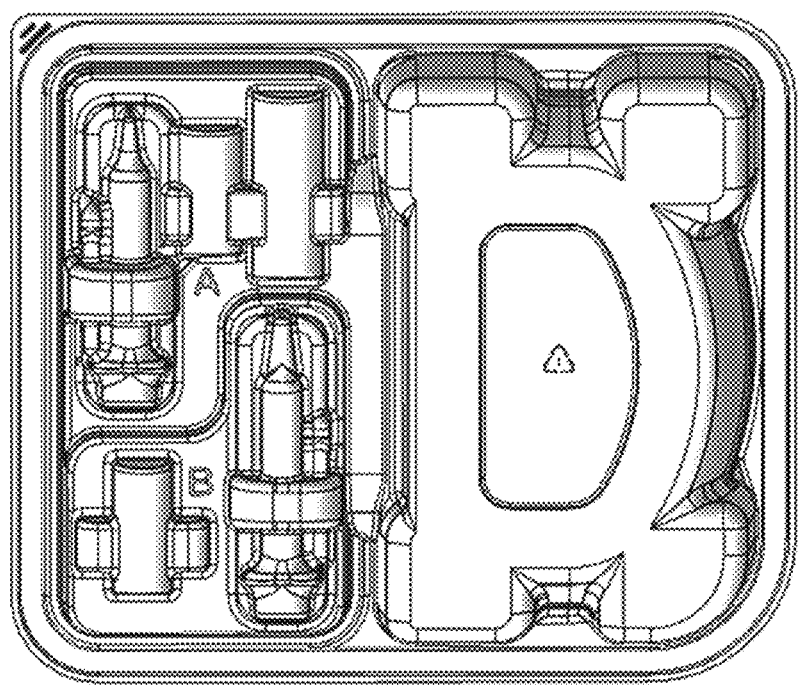
Figure 62D:
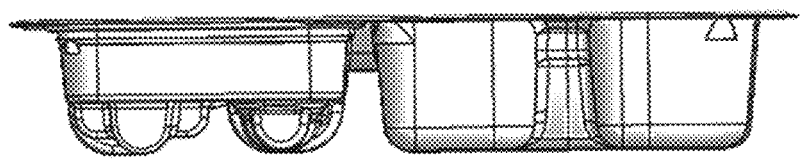
Figure 62E:
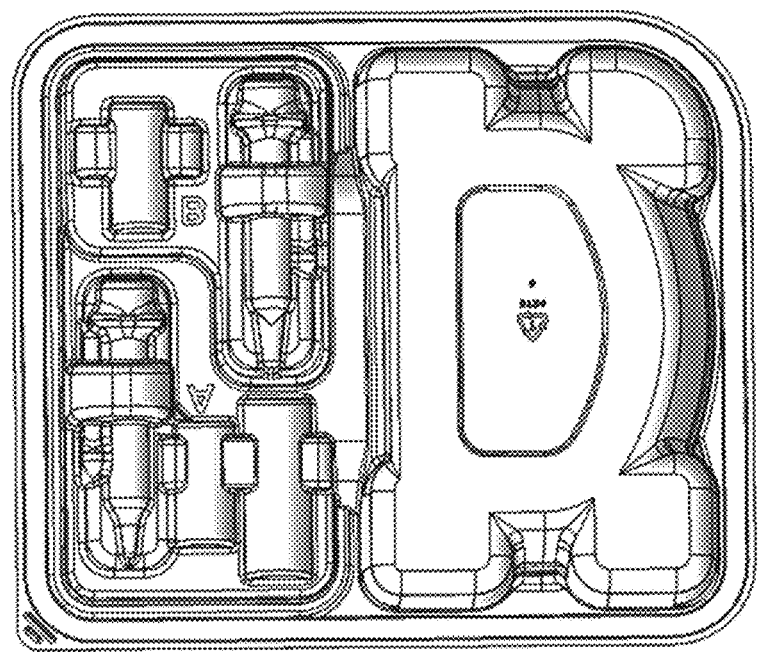
Figure 62F:
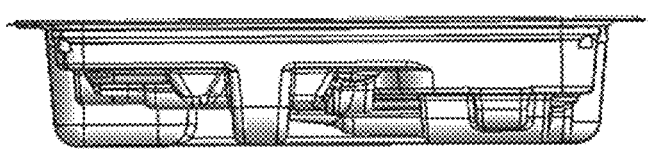
Figure 62G:
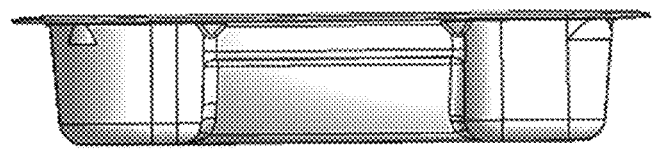

FIGS. 60A and 60B are detailed illustrations of an example embodiment of a packaging system for a kit for preparing and/or applying a cell suspension. Specifically, FIGS. 60A and 60B depict an example assembly of a housing including a base, an integrated tray portion (including first and second housing portions, with visual indicators "A" and "B", as well as a device recess), and a third housing portion with a visual indicator "C". Each of the first, second, and third housing portions include recesses for receiving in a snap-fit manner various first, second, and third components for use in first, second, and third portions of a method for preparing and/or applying a cell suspension. FIG. 60A depicts an exploded view of the assembly with housing liners configured to be arranged over the first and second housing portions, while FIG. 60B depicts the assembly without housing liners.

FIGS. 61A-61G are detailed illustrations of a base in the example housing assembly shown in FIGS. 60A and 60B. Specifically, FIGS. 61A-61G depict a perspective view, a rear view, a top plan review, a front view, a bottom view, a left view, and a right view, respectively, of a base in a kit for preparing and/or supplying a cell suspension.

FIGS. 62A-62G are detailed illustrations of an integrated tray portion in the example housing assembly shown in FIGS. 60A and 60B. Specifically, FIGS. 62A-62G depict a perspective view, a rear view, a top plan review, a front view, a bottom view, a left view, and a right view, respectively, of an integrated tray portion in a kit for preparing and/or supplying a cell suspension.

Figure 63A:
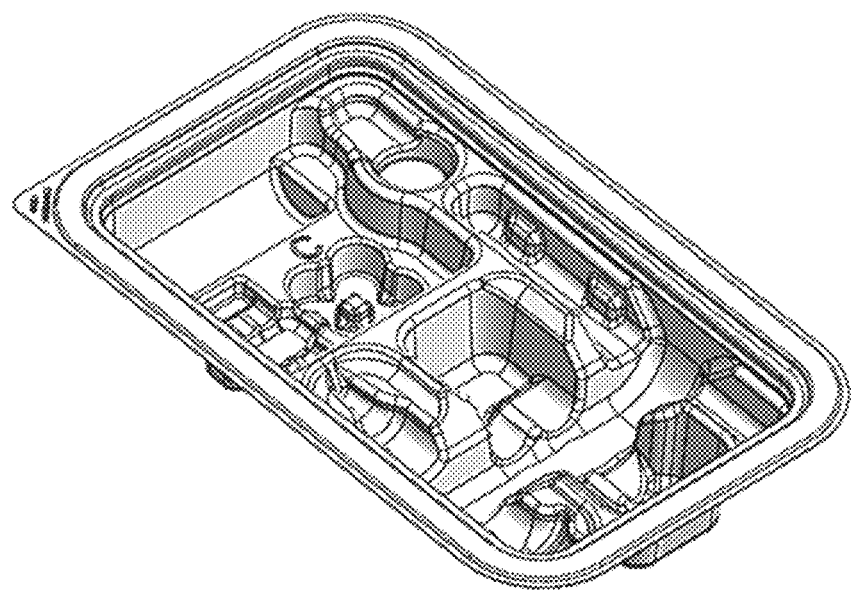
FIGS. 63A-63G are a perspective view, a rear view, a top plan review, a front view, a bottom view, a left view, and a right view, respectively, of a housing portion in a kit for preparing and/or supplying a cell suspension, according to an embodiment.
Figure 63B:
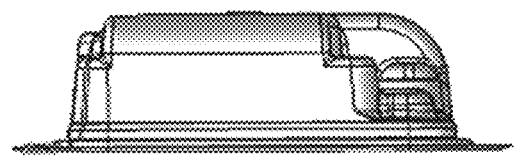
Figure 63C:
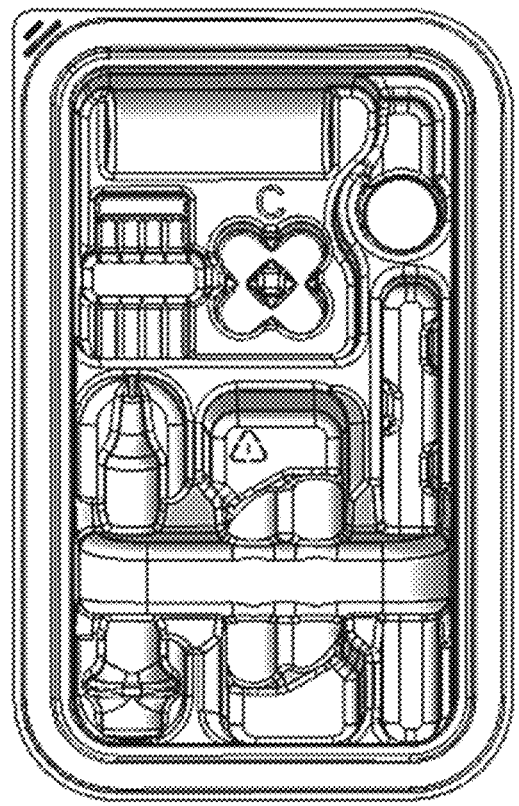
Figure 63D:
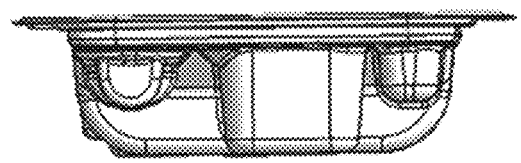
Figure 63E:
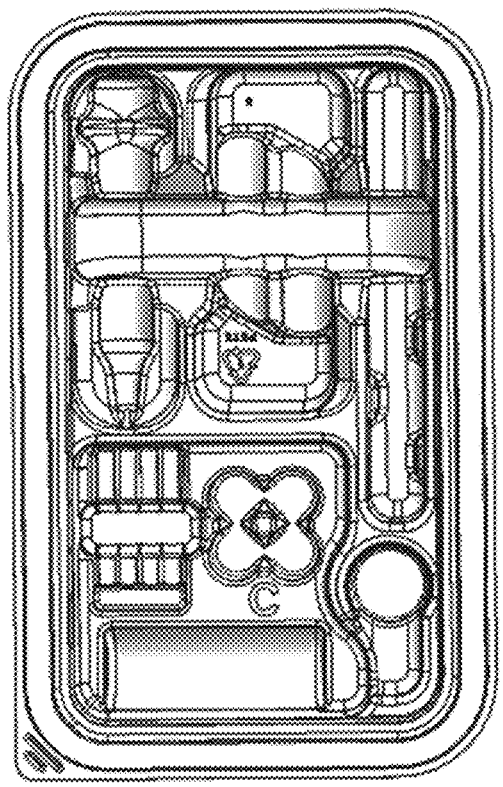
Figure 63F:
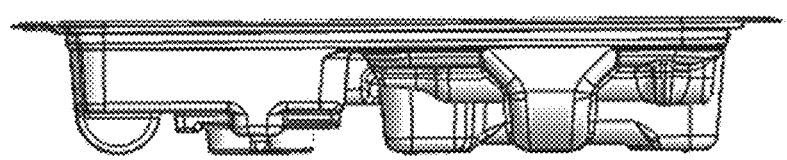
Figure 63G:
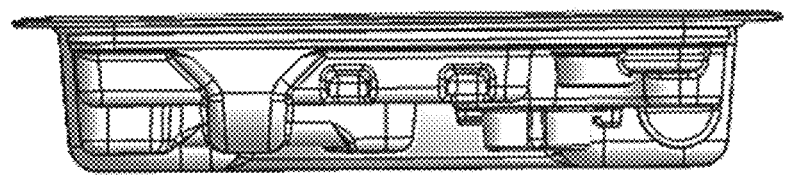

FIGS. 63A-63G are detailed illustrations of a third housing portion in the example housing assembly shown in FIGS. 60A and 60B. Specifically, FIGS. 63A-63B depict a perspective view, a rear view, a top plan review, a front view, a bottom view, a left view, and a right view, respectively, of a third housing portion in a kit for preparing and/or supplying a cell suspension.

Methods for Preparing and Applying a Cell Suspension

Kits and devices such as that described above may be used to perform a tissue processing method, such as a method for preparing and applying a cell suspension. Described below are example variations of such a method.

As discussed above, the tissue processing method may include a first portion, a second portion, and optionally a third portion. Prior to performing one of the first portion, the second portion, or the third portion of the tissue processing method, a user may identify which of the first housing portion 130, the second housing portion 140, and the optional third housing portion 160 are associated with the particular portion of the tissue processing method. For example, the user may do so at least in part by identifying a match between one of the first label 112, the second label 114, and the third label 116 and one of the first visual indicator 132, the second visual indicator 142, and the third visual indicator 162. For example, a user may view the device 110 and identify the first label 112 associated with the first reservoir 111, and then seek to identify a corresponding first visual indicator 132 among the first housing portion 130, the second housing portion 140, and the third housing portion 160. Upon identifying that the first visual indicator 132 is associated with the first housing portion 130, the user may begin the first portion of the tissue processing method using the first set of components stored in the recesses of the first housing portion 130. Following a similar procedure with respect to the second reservoir 113, upon identifying that the second housing portion 140 includes the second visual indicator 142 that corresponds to the second label 114 associated with the second reservoir 113, the user may begin the second portion of the tissue processing method using the second set of components stored in the recesses of the second housing portion 140. Following a similar procedure with respect to the third reservoir 115, upon identifying that the third housing portion 160 includes the third visual indicator 162 that corresponds to the third label 116 associated with the third reservoir 115, the user may begin the third portion of the tissue processing method using the third set of components stored in the recesses of the third housing portion 160.

In some implementations, the first portion of the tissue processing method may include preparing an enzyme mixture for the tissue processing method and delivering the enzyme mixture into the first reservoir 111. For example, the first housing portion 130 may be moved to an intended workspace (e.g., from the box 108 and/or integrated tray portion 150 into or near a sterile field). A cover of the enzyme vial may be removed from the enzyme vial recess of the first housing portion and a diaphragm of the vial may be optionally wiped with a sterile alcohol wipe and allowed to dry. A needle (e.g., of the first set of components) may be fluidically coupled to a syringe of the first set of components. The needle of the first set of components may be inserted into an interior of a water vial (e.g., of the first set of components) and a volume of water (e.g., the entire volume of the water vial) may be drawn from the water vial into the syringe. The volume of water (e.g., the entire volume of water in the syringe) may be injected from the syringe into the interior of the enzyme vial and mixed gently (e.g., without shaking to avoid foaming) until the enzyme is dissolved in the water to form an enzyme mixture. The enzyme mixture may be drawn back into the syringe. The enzyme mixture may then be dispensed into the first reservoir 111 of the device 110. The syringe and needle may be discarded.

In some implementations, the second portion of the tissue processing method may include preparing a buffer for the tissue processing method (e.g., drawing a volume of the buffer from a buffer vial and delivering the volume of the buffer to the second reservoir 113). A subset of components from the second set of components may be transferred from a non-sterile preparation area of the workspace into a sterile field. In the sterile field, an empty buffer syringe (e.g., of the second set of components) may optionally be marked "buffer" and an empty unfiltered suspension syringe (e.g., if included in the second set of components) may optionally be marked "unfiltered suspension." In implementations in which the unfiltered suspension syringe is included in the third set of components, the unfiltered suspension is not handled during the second portion of the tissue processing method. In the non-sterile preparation area, a cover may be removed from a buffer vial (e.g., of the second set of components) and a diaphragm of the buffer vial may be optionally wiped with a sterile alcohol wipe and allowed to dry. In the sterile field, a needle (e.g., of the second set of components) may be coupled to the buffer syringe. In the non-sterile preparation area, the buffer vial may be positioned such that a user in the sterile field may draw a volume of the buffer from the buffer vial. The user in the sterile field may dispose a free end of the needle in an interior of the buffer vial and a volume of the buffer (e.g., the entire volume of the buffer) may be drawn into the syringe. In the sterile field, the volume of the buffer may be dispensed into the second reservoir 113 of the device 110. The syringe with the needle attached may be set aside within the sterile field.

In some implementations, the third portion of the tissue processing method may include preparing for delivery of a cell suspension to a patient (e.g., disaggregating a skin sample, creating a cell suspension including cells from the disaggregated skin sample, and drawing the cell suspension into a skin cell syringe). A set of skin cell syringes (e.g., four skin cell syringes), a set of needles, and a set of spray nozzles (e.g., all from the third set of components) may be disposed in the sterile field (e.g., within the third housing portion 160 or after being removed from the third housing portion 160). The wound bed of the patient may be prepared. For example, the wound bed may be clean and vascularized (e.g., via rotating diamond-head burr, laser ablation, sharp dissection, or other alternative techniques). Additionally, prophylactic antibiotics may be optionally administered and/or the wound may be swabbed about forty-eight hours prior to the tissue processing method or procedure. All necrotic tissue may be removed and pinpoint bleeding may be observed. A skin sample may be extracted from a donor site of the patient such that pinpoint bleeding occurs at the donor site. The skin sample may be about 0.15-0.20 mm thick. The skin sample may be a thin, split-thickness skin sample. In some implementations, a dermatome or a similar device may be used to remove the skin sample.

In some embodiments, an area of skin sample may be correlated to an estimated cell suspension volume and/or skin treatment area. For example, in some embodiments, each square centimeter of skin sample may create 1 ml of cell suspension using the kit 100 for preparing a cell suspension. Each milliliter of cell suspension may be disposed over a treatment area between about 10 $cm^2$ and about 100 $cm^2$, between about 25 $cm^2$ and about 100 $cm^2$, between about 50 $cm^2$ and about 100 $cm^2$, or up to about 25 $cm^2$, up to about 50 $cm^2$, up to about 75 $cm^2$, or up to about 100 $cm^2$. For example, in some embodiments, each milliliter of cell suspension may be disposed over a treatment area of up to about 80 $cm^2$ (e.g., allowing for an expansion ratio of up to about 1:80). Thus, a 6 $cm^2$ skin sample may yield about 6 ml of cell suspension. Each kit 100 may process up to four 6 $cm^2$ skin samples to produce up to 24 ml of cell suspension. The 24 ml of cell suspension may be used to treat a treatment area of approximately up to 1,920 $cm^2$. For example, by way of example only, Table 1 includes a skin sample size that may be obtained to treat a variety of treatment area sizes using the kit 100.

TABLE 1

| Treatment Area | Skin Sample Size |
|---|---|
| up to 80 $cm^2$ | 1 cm × 1 cm (1 $cm^2$) |
| up to 160 $cm^2$ | 2 cm × 1 cm (2 $cm^2$) |
| up to 320 $cm^2$ | 2 cm × 2 cm (4 $cm^2$) |
| up to 480 $cm^2$ | 3 cm × 2 cm (6 $cm^2$) |
| up to 960 $cm^2$ | 2 ea. 3 cm × 2 cm (12 $cm^2$) |
| up to 1440 $cm^2$ | 3 ea. 3 cm × 2 cm (18 $cm^2$) |
| up to 1920 $cm^2$ | 4 ea. 3 cm × 2 cm (24 $cm^2$) |

Using the device 110, the enzyme mixture in the first reservoir 111 may be heated (e.g., using the heating assembly of the device 110 described above). For example, an activation button on the device 110 may be pressed to initiate heating of the enzyme mixture in the first reservoir 111. As the enzyme mixture is heated to a target temperature, a first light indicator (e.g., an orange warming light) may be illuminated. Upon the enzyme mixture reaching the target temperature, a second light indicator may be illuminated (e.g., a green check light). In some implementations, the heating of the enzyme mixture to the target temperature may be achieved in about three minutes or other suitable period of time. In some implementations, the first light indicator may flash briefly to indicate that the heating element has been intermittently or periodically activated to maintain the temperature of the enzyme mixture.

One or more skin samples (e.g., two skin samples each having a size equal to or less than six $cm^2$) may be placed into the first reservoir 111 and submerged in the heated enzyme mixture for a first period of time such that the enzyme mixture may break down protein-protein interactions. The first period of time may be, for example, between about fifteen minutes and about twenty minutes. Thicker skin samples may be incubated for a longer period of time (e.g., up to sixty minutes). In some implementations, an audio and/or visual alarm of the device 110 may provide a notification, such as every five minutes, every ten minutes, every fifteen minutes, every twenty minutes, every thirty minutes, etc. Additionally or alternatively, an audio and/or visual alarm may provide a notification at varying frequencies, such as after completion of a first period of time (e.g., between about fifteen minutes and about twenty minutes), and thereafter indicate passage of periodic intervals (e.g., each minute, each five minutes) for a second period of time. After a certain amount of time (e.g., after fifteen minutes, after thirty minutes, after sixty minutes, etc.) the device 110 may deactivate such that the heating assembly ceases heating the enzyme mixture. Examples of audio alarms include sound effects (e.g., beeps, tones, etc.), dictated indication of time (e.g., "fifteen minutes"), and dictated instructions (e.g., "remove sample" or "check sample"). Examples of visual alarms include activation of lights (e.g., LED) and text notifications (e.g., on the device 110). It should be understood that an alarm communicating these notifications may be in any suitable form (e.g., audio, visual, tactile, etc.) and/or communicated to a third party device (e.g., monitor screen, mobile computing device) that provides the notification.

In some implementations, at least a portion of the second portion of the tissue processing method may be performed simultaneously with a third portion of the tissue processing method. For example, the buffer may be delivered to the second reservoir 113 while the skin samples are incubating in the enzyme mixture in the first reservoir 111.

The skin sample(s) may be removed from the heated enzyme mixture and placed dermal side down on the preparation tray of the device 110. For example, sterile forceps or scalpels of the third set of components may be used to remove the skin sample(s) from the first reservoir 111 and to place the skin sample(s) on the preparation tray. The epidermis edge of each skin sample may be scraped gently with the scalpel to test if the cells disaggregate (e.g., if the epidermal cells separate easily). If the cells disaggregate, the scraping may be stopped. If the cells do not disaggregate, the skin sample may be returned to the heated enzyme mixture for a period of time (e.g., about five to ten minutes), and then removed for additional test scraping to determine whether the cells disaggregate. If the cells scrape freely, the skin sample may be placed in the second reservoir 113 and submerged in the buffer to rinse off any residual enzyme mixture on the skin sample. When applicable, the second incubated skin sample may also be placed in the second reservoir 113 after passing the disaggregation test. If a third skin sample and/or a fourth skin sample are desired to be processed, each of the third skin sample and the fourth skin sample may be placed in the first reservoir 111 and submerged in the enzyme mixture while the first and second skin sample are being rinsed in the second reservoir 113.

A volume of buffer may be drawn into the buffer syringe of the second set of components from a second buffer vial (e.g., of the third set of components). The volume of buffer may include, for example, about 1 ml of buffer per square centimeter of the first skin sample and an additional amount (e.g., about 0.5 ml) of buffer to allow for loss during processing. Table 2 describes example starting volume of buffer and approximate resultant suspension volume for various treatment area surface sizes per syringe volume and skin sample sizes. As described above, in some embodiments each milliliter of cell suspension may be disposed over a treatment area between about 10 cm² and about 100 cm², between about 25 cm² and about 100 cm², between about 50 cm² and about 100 cm², or up to about 25 cm², up to about 50 cm², up to about 75 cm², or up to about 100 cm². In some embodiments, each 1 ml of the suspension may be used to treat up to 80 cm² of treatment area (e.g., allowing for an expansion ratio of up to about 1:80). In some embodiments, the volume of cell suspension to be applied may vary depending on the application method. For example, in some embodiments a suspension volume of greater than or equal to 2 ml may be applied to the treatment area via spraying. As another example, in some embodiments a suspension volume of less than 1 ml may be applied to the treatment area using the drip method.

TABLE 2

| Surface Area to be Treated per Syringe | Skin Sample Size | Starting Volume of Buffer, per Sample | Approximate Resultant Suspension Volume |
|---|---|---|---|
| Up to 80 cm² | 1 cm² (1 cm × 1 cm) | 1.5 ml | 1.0 ml |
| Up to 160 cm² | 2 cm² (2 cm × 1 cm) | 2.5 ml | 2.0 ml |
| Up to 320 cm² | 4 cm² (2 cm × 2 cm) | 4.5 ml | 4.0 ml |
| Up to 480 cm² | 6 cm² (3 cm × 2 cm) | 6.5 ml | 6.0 ml |

A skin sample may be removed from the second reservoir 113 and placed on the preparation tray (e.g., dermal side down). A few drops of buffer from the buffer syringe may be applied to the skin sample. Using forceps or other suitable instrument to anchor the skin sample, the epidermal surface may be gently scraped with the blade of the scalpel. Once the epidermis has been scraped into a cell suspension, the remaining dermis may be scraped more vigorously until the dermis has nearly disintegrated. The remaining buffer in the first syringe may be used to rinse the scalpel and tray such that the cell suspension may be collected in a collection area of the preparation tray. For example, the suspension of cells may be collected in a corner of the tray that may be below other regions of the tray when the device 110 including the preparation tray are disposed on a level surface. The tray may be tilted to pool the cell suspension in the corner as needed. Example features (e.g., textural features, elevation features, etc.) of various embodiments of the preparation tray are described in further detail below. The buffer syringe may be set aside for later use.

The cell suspension may be drawn into an unfiltered suspension syringe (e.g., of the third set of components) and then delivered to the preparation tray to rinse the preparation tray. The cell suspension may be repeatedly drawn up and delivered to rinse the tray to maximize cell collection, and then at least a portion (e.g., substantially all) of the cell suspension may be drawn into the unfiltered suspension syringe. If not already disposed in the third reservoir 115, a cell strainer (e.g., of the third set of components) may then be placed in the third reservoir 115. The cell suspension may be dispensed from the unfiltered suspension syringe through the cell strainer and into the third reservoir 115. The cell strainer may be configured with a filter size suitable to remove large particulates, such as to prevent nozzle blockage when spraying the cellular suspension onto the treatment surface. For example, in some embodiments the cell strainer may have a filter size of less than about 200 μm, less than about 150 μm, less than about 100 μm, less than about 50 μm, or other suitable filter size. The unfiltered suspension syringe may be set aside within the sterile field for later use associated with any remaining skin samples. After passing the cell suspension through the cell strainer, the cell strainer may be removed from the third reservoir 115. The cell strainer may optionally be tapped over the third reservoir 115 to release any drops of cell suspension into the third reservoir 115. If the cell suspension becomes clogged (e.g., when processing multiple skin samples), the cell suspension may be drawn from the cell strainer back into the unfiltered suspension syringe and a new cell strainer (e.g., from another kit 100) may be installed in the third reservoir 115 for performing additional filtering.

A needle (e.g., of the third set of components) may be coupled to a skin cell syringe (e.g., of the third set of components). The filtered cell suspension in the third reservoir 115 may be drawn into the skin cell syringe. The third reservoir 115 may be shaped to include a conical bottom to aid in collection of the filtered cell suspension and drawing the filtered cell suspension into the needle coupled to the skin cell syringe. The skin cell syringe may be set aside for later application of the filtered cell suspension to the treatment surface. The steps of scraping the skin sample to creating an unfiltered suspension of skin cells, rinsing the tray to maximize cell collection, passing the cell suspension through the filter, and drawing the filtered cell suspension into a skin cell syringe (e.g., of the third set of components) may be repeated to produce a skin cell syringe of a filtered cell suspension for each skin sample.

In some embodiments, one or more dressings may be prepared prior to delivery of the filtered cell suspension to the treatment surface (e.g. wound bed, site of pigmentation condition, etc.). Each dressing may be cut to a proper shape and/or size and may be disposed at or near the lower aspect of the treatment surface (e.g., via being fixed using surgical glue, sutures, or staples, or via being held) prior to applying the cell suspension to reduce runoff from the treatment surface. The cell suspension may then be applied to the treatment surface. In some embodiments, the cell suspension may be applied directly to partial-thickness wounds or in combination with meshed autografts for full-thickness wounds.

Application of the prepared cell suspension to a treatment surface of a patient may be performed in various manners. For example, the cell suspension may be sprayed or dripped onto the treatment surface depending on the volume of cell suspension to be applied and the size of the treatment surface. Prior to application, the skin cell syringe may be inverted several times to help ensure that the suspension is applied evenly.

For a spray application of the cell suspension, the needle may be removed from the skin cell syringe containing the cell suspension. A spray nozzle from a set of spray nozzles (e.g., from the third set of components) may be coupled to the skin cell syringe in place of the needle. The spray nozzle may be oriented toward the treatment surface and positioned above the treatment surface (e.g., disposed about 10 cm from the most elevated point of the treatment surface) and in a position such that the first drop of suspension may fall onto the treatment surface. By applying pressure to a plunger of the skin cell syringe, the cell suspension may be sprayed at the most elevated portion of the treatment surface so that any run-off flows to cover the lower areas of the treatment surface. The cell suspension may be sprayed as a fine mist to the treatment surface. For larger treatment surfaces, the spray applicator (e.g., spray nozzle and skin cell syringe combination) may be moved in a continuous motion from one side to the other while spraying.

For a drip application, the needle may remain on the skin cell syringe containing the cell suspension. in some embodiments, starting at the most elevated portion of the treatment surface, cell suspension may be carefully dripped onto the treatment surface so that any run-off flows to cover the lower areas of the treatment surface.

After applying the cell suspension, the treatment surface may be covered with the one or more dressings. The dressings may be non-adherent, non-absorbent, and/or a small pore dressing. In some implementations, the dressings may be lightly soaked in sterile saline before dressing the treatment surface. The dressings may be fixed to the treatment surface with surgical glue, sutures, or staples, or other suitable fastener(s) as needed. A secondary dressing may be placed over the primary dressing. The secondary dressing may be moderately absorbent, minimally adherent, low shear, and readily removable. An absorbent gauze may be placed over the secondary dressing.

In some implementations, the kit 100 may include a mechanism configured to enable removal of vial lids, needle sheaths, and/or syringe caps. For example, the kit 100 may include a bottle opener. In some implementations, the housing 120 may include a single piece protective packaging layer that includes a pull tab coupled to a removable sealing portion of the packaging layer such that pulling on the pull tab breaks the sealing portion and allows the interior of the packaging layer to be accessed. The packing layer may include a viewing window (e.g., a transparent region allowed a user to see into the packaging interior). Instructions may be included on the packaging layer (e.g., molded into the packaging layer or printed on the packaging layer). In some implementations, the base 170, integrated tray portion 150, the first housing portion 130, the second housing portion 140, and/or the third housing portion 160 may include a single piece protective packaging layer and/or be collectively surrounded by a single piece protective packaging layer.

Figure 2:
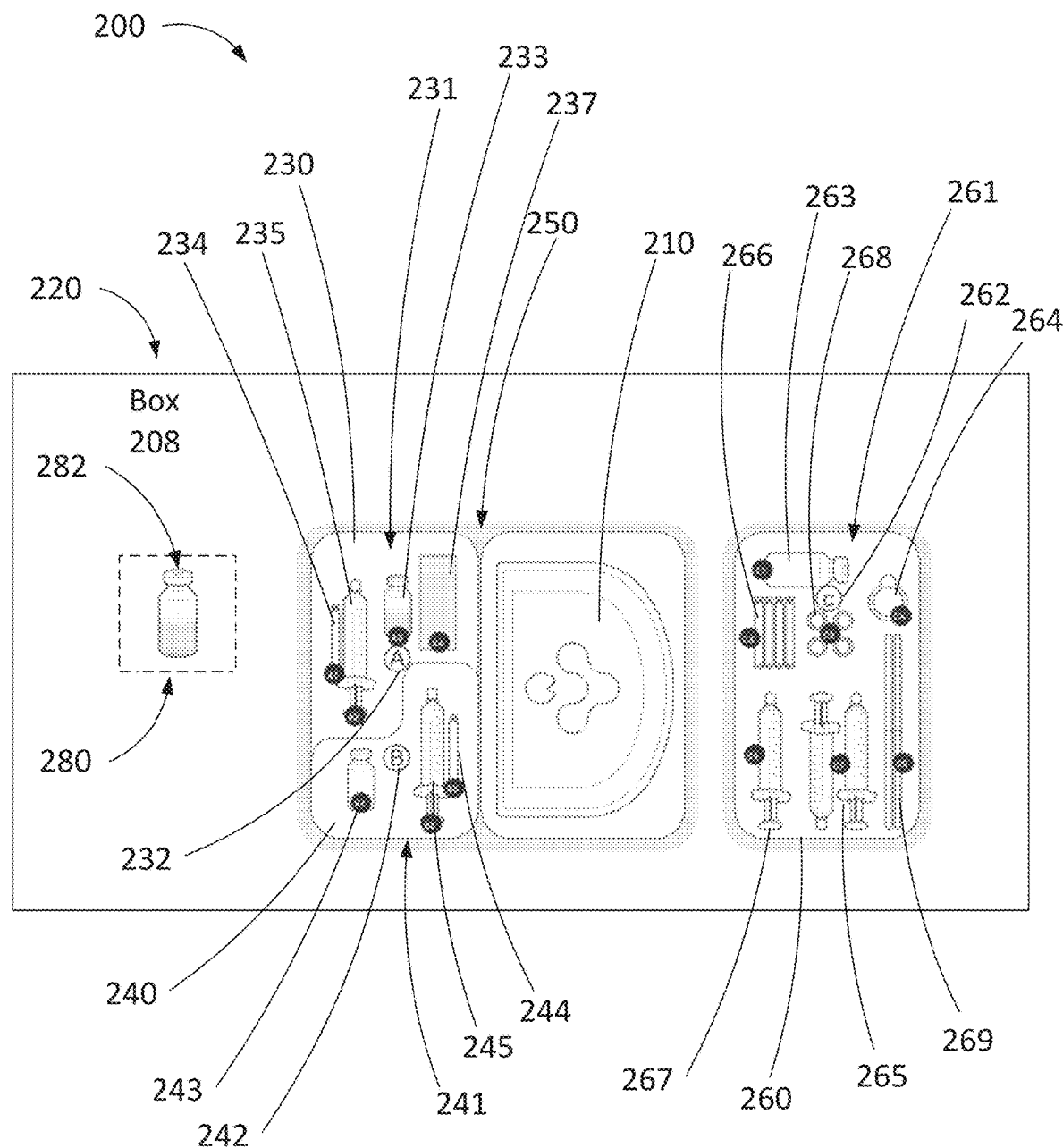
FIG. 2 is a schematic illustration of a kit for preparing a cell suspension, according to an embodiment.

FIG. 2 is a schematic illustration of an example kit 200 for preparing a cell suspension. The kit 200 may be the same or similar in structure and/or function to the kit 100 described above. For example, the kit 200 includes a housing 220 and a device 210, which may be the same or similar in structure and/or function to the housing 120 and the device 110, respectively. The housing 220 includes a box 208, a first housing portion 230, a second housing portion 240, a third housing portion 260, and an integrated tray portion 250, which may be the same or similar in structure and/or function to the box 108, the first housing portion 130, the second housing portion 140, the third housing portion 160, and the integrated tray portion 150 described above with respect to FIG. 1. For example, the housing 220 may optionally define a vial recess 280 configured to receive a vial 282. The vial 282 may contain an enzyme (e.g., an enzyme suitable for dissociating cellular stratum in a skin tissue sample, such as trypsin, trypsin-EDTA, dispase, collagenase, thermolysin, pronase, hyaluronidase, pancreatin, elastase, papain, etc.). Additionally, the first housing portion 230 includes a first visual indicator 232, the second housing portion 240 includes the second visual indicator 242, and the third housing portion 260 includes the third visual indicator 262. Each of the first visual indicator 232, the second visual indicator 242, and the third visual indicator 262 are configured to correspond to a first label, a second label, and a third label (not shown) of the device 210 similarly as described above with respect to the kit 100 of FIG. 1.

As shown in FIG. 2, a first set of components 231 associated with a first portion of a tissue processing method may be disposed in the first housing portion 230, a second set of components 241 associated with a second portion of the tissue processing method may be disposed in the second housing portion 240, and a third set of components 261 associated with a third portion of the tissue processing method may be disposed in the third housing portion 260.

The first set of components 231 includes a water vial 233 containing a volume of water (e.g., sterile water), a needle 234, and an enzyme syringe 235. For example, the enzyme syringe 235 may be a 10 ml syringe. The needle 234 may be configured to be coupled to the enzyme syringe 235. As shown in FIG. 2, the first housing portion 230 may define a recess 237 configured to receive the enzyme vial 282 (e.g., for transporting the enzyme vial 282 from a box 208 to a workspace). The second set of components 241 may include a vial 243 containing a buffer, a needle 244, and a buffer syringe 245. The needle 244 is configured to be coupled to the buffer syringe 245. The needle 244 may be, for example, a blunt fill needle. The third set of components 261 includes a vial 263 containing a buffer, a cell strainer 264, a set of skin cell syringes 265, a set of needles 266, an unfiltered suspension syringe 267, a set of spray nozzles 268, and a pair of scalpels 269. The buffer vial 263 may include, for example, 30 ml of buffer or other suitable volume of buffer. The buffer may include a suitable solution for diluting or neutralizing the enzyme. For example, in some embodiments the buffer may include a physiological saline (e.g., Ringer's lactate solution, or sodium lactate solution or Hartmann's solution). For example, the set of skin cell syringes 265 may include a suitable number of syringes, such as four skin cell syringes (e.g., 10 ml syringes). The set of needles 266 may include a suitable number of needles, such as four needles (e.g., blunt fill needles stacked 2 by 2 in the third housing portion 260). The set of spray nozzles 268 may include a suitable number of spray nozzles, such as four spray nozzles. Each needle of the set of needles 266 may be coupled to a skin cell syringe of the set of skin cell syringes 265. Additionally, in the alternative to a needle from the set of needles 266, each spray nozzle of the set of spray nozzles 268 may be coupled to a skin cell syringe of the set of skin cell syringes 265. Each of the components of the first set of components 231, the second set of components 241, and the third set of components 261 may be the same or similar in structure and/or function to the corresponding component of the first set of components, the second set of components, and the third set of components described above with respect to the kit 100 of FIG. 1.

FIG. 3 is a flow chart illustrating a method 300 for preparing a cell suspension using a device packaged in a housing, such as a device packaged in a housing of a kit for preparing a cell suspension as described herein. The kit may be any of the kits described herein, such as the kit 100 and/or the kit 200 described above.

The method 300 includes identifying 302 a first match between a first label disposed proximate a first reservoir of the device and a first visual indicator included in a first housing portion of the housing. In response to (or after) identifying the first match, a first set of components from the first housing portion may be removed 304 and the first set of components may be used to perform a first portion of a tissue processing method associated with the first reservoir. A second match may be identified 306 between a second label disposed proximate a second reservoir of the device and a second visual indicator included in a second housing portion of the housing. In response to (or after) identifying the second match, a second set of components may be removed 308 from the second housing portion and the second set of components may be used to perform a second portion of the tissue processing method associated with the second reservoir.

One or more housing portions may be transferred to a sterile procedure area during the method. In some implementations, in response to (or after) identifying the first match, the first housing portion may be transferred into a sterile procedure area. In some implementations, in response to (or after) identifying the second match, the second housing portion may be transferred into a sterile procedure area. In some implementations, a match may be identified between third match between a third label disposed proximate a third reservoir of the device and a third visual indicator included in the third housing portion of the housing. In response to identifying the third match between a third label disposed proximate a third reservoir of the device and a third visual indicator included in the third housing portion of the housing, a third set of components may be removed from the third housing portion and using the third set of components to perform a third portion of the tissue processing method associated with the third reservoir. In some implementations, a tissue manipulation portion of the tissue processing method may be performed on a preparation tray of the device, as described above. In some implementations, the first set of components may include a vial of sterile water, a syringe, and an enzyme vial.

The first portion of the tissue processing method associated with the first reservoir may include preparing an enzyme mixture and delivering the enzyme mixture into the first reservoir. In some implementations, an enzyme vial may be removed from a sterile pouch and the enzyme vial may be disposed in a recess defined in the first housing portion. In some implementations, the second set of components may include a buffer vial and a syringe. The second portion of the tissue processing method associated with the second reservoir may include drawing a volume of the buffer from the buffer vial into the syringe, and delivering the volume of the buffer from the syringe to the second reservoir. In some implementations, the third set of components includes a syringe. The third portion of the tissue processing method associated with the third reservoir may include disaggregating a skin sample, creating a cell suspension including cells from the disaggregated skin sample, and drawing the cell suspension into the syringe.

Example Embodiments

Figure 4:
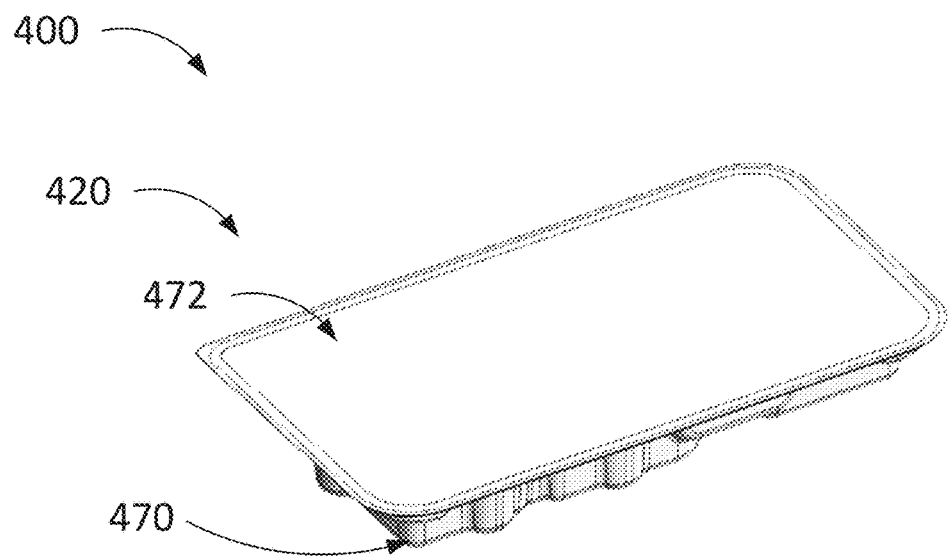
Figure 5:
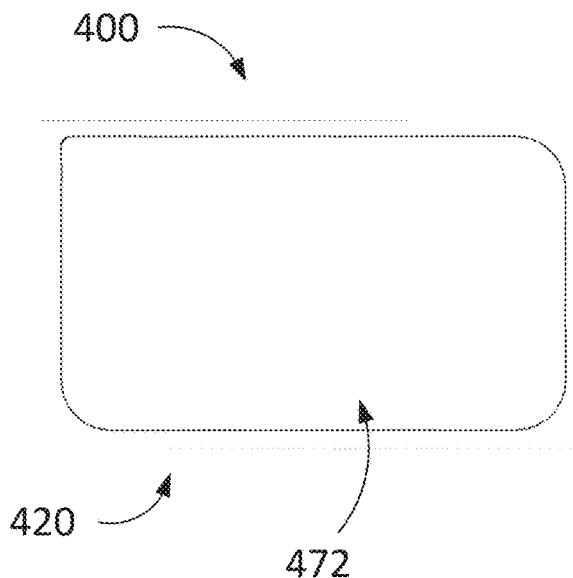
Figure 6:
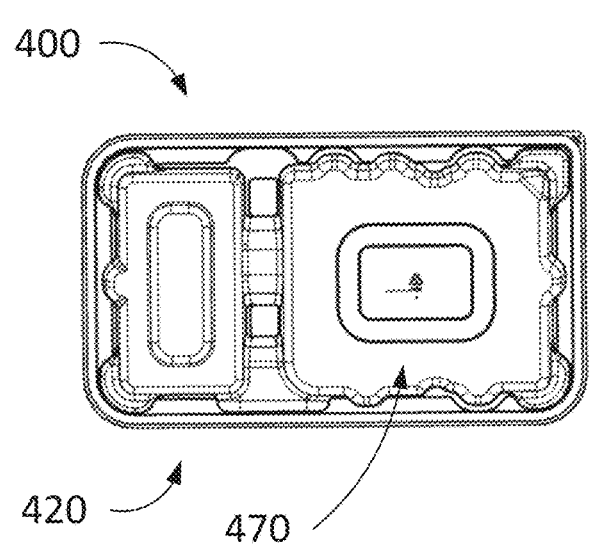

FIGS. 4-6 are a perspective view, a top view, and a bottom view, respectively, of a kit 400. The kit 400 may be the same or similar in structure and/or function to any of the kits described herein, such as the kit 100 or the kit 200. The kit 400 may be used to prepare a cell suspension. The kit 400 includes a housing 420 that may be the same or similar in structure and/or function to any of the housings described herein, such as the housing 120 and the housing 220. As shown in FIG. 4, the housing 420 includes a base 470 and a lid 472 coupled to the base 470 to collectively define an enclosed space and maintain the sterility of the interior of the base 470 prior to use of the kit 400. The lid 472 may, for example, include a cover that is removably coupled to the base 470 via one or more fasteners (e.g., adhesive, mechanical fasteners), snap fit, and/or the like. In some embodiments, the lid 472 may include a cover such as a thin film (e.g., coupled to the base 470 via adhesive) including a polymer, a foil, etc. The lid 472 may be transparent or translucent, thereby allowing visualization of the contents of the housing 420. For example, the lid 472 may include Tyvek®. Alternatively, in some embodiments the lid 472 may include a hinged cover (e.g., similar to clamshell packaging).

Figure 7:
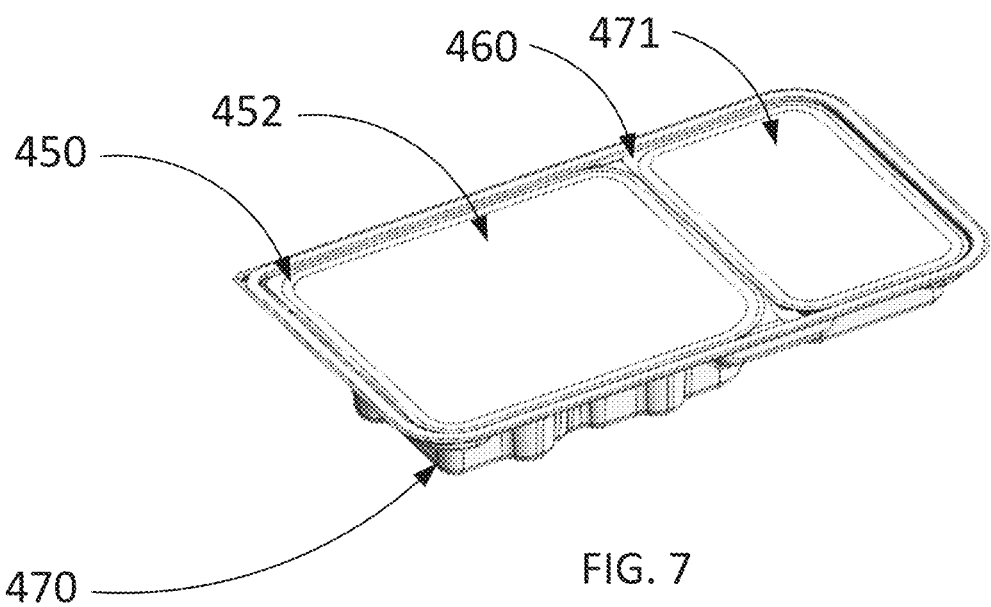
Figure 8:
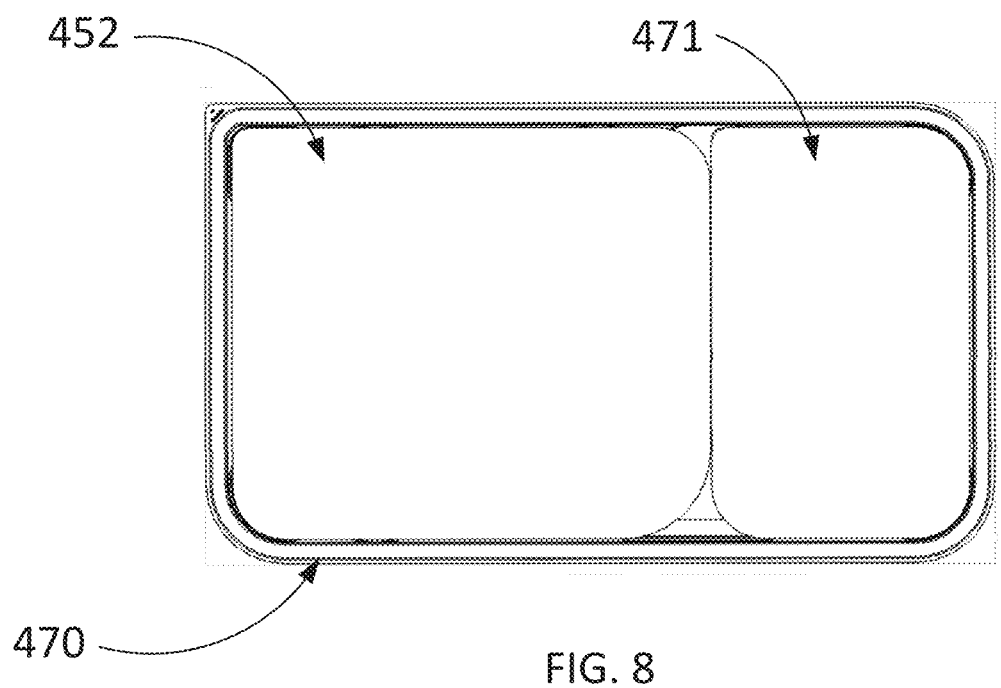
Figure 9:
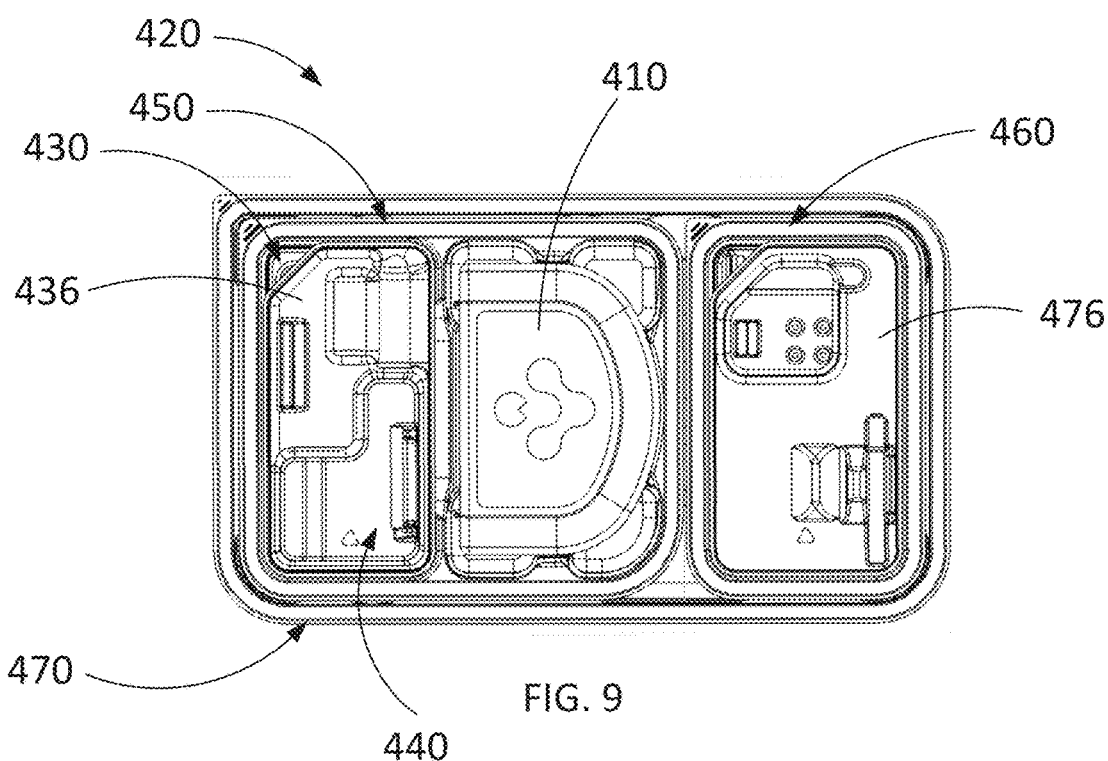

FIGS. 7 and 8 are a perspective view and a top view of the housing 420 with the lid 472 removed from the base 470. As shown in FIGS. 7 and 8, an integrated tray portion 450 having a lid 452 and a third housing portion 460 having a lid 471 are disposed within the base 470. In some embodiments, the lid 452 and/or the lid 471 may be similar in material and function as that of the lid 472. FIG. 9 is a top view of the housing 420 with the lids 452 and 471 removed, thereby exposing the first housing portion 430, the second housing portion 440, and the third housing portion 460. As shown in FIG. 9, a first housing portion 430, a second housing portion 440, and a device 410 are disposed in the integrated tray portion 450. A liner 436 may be coupled to some or all of integrated tray portion 450 (e.g., the first housing portion 430 and/or the second housing portion 440, thereby providing a cover (e.g., for better retention of the first and/or second sets of components in the first housing portion 430 and/or the second housing portion 440). In some embodiments, the first housing portion 430 and the second housing portion 440 may have separate and distinct liners (e.g., a first liner coupled to the first housing portion 430, and a second liner coupled to the second housing portion 440). Similarly, a liner 476 may be coupled to the third housing portion 460, thereby providing a cover for the third set of components in the third housing portion 460. Liner 436 and/or liner 476 may, for example, include one or more cavities or recesses with a perimeter that matches the shape of one or more components in the housing. In some embodiments, one or both liners may include a suitable polymer such as Polyethylene terephthalate glycol (PETG), or other suitable material.

Figure 10:
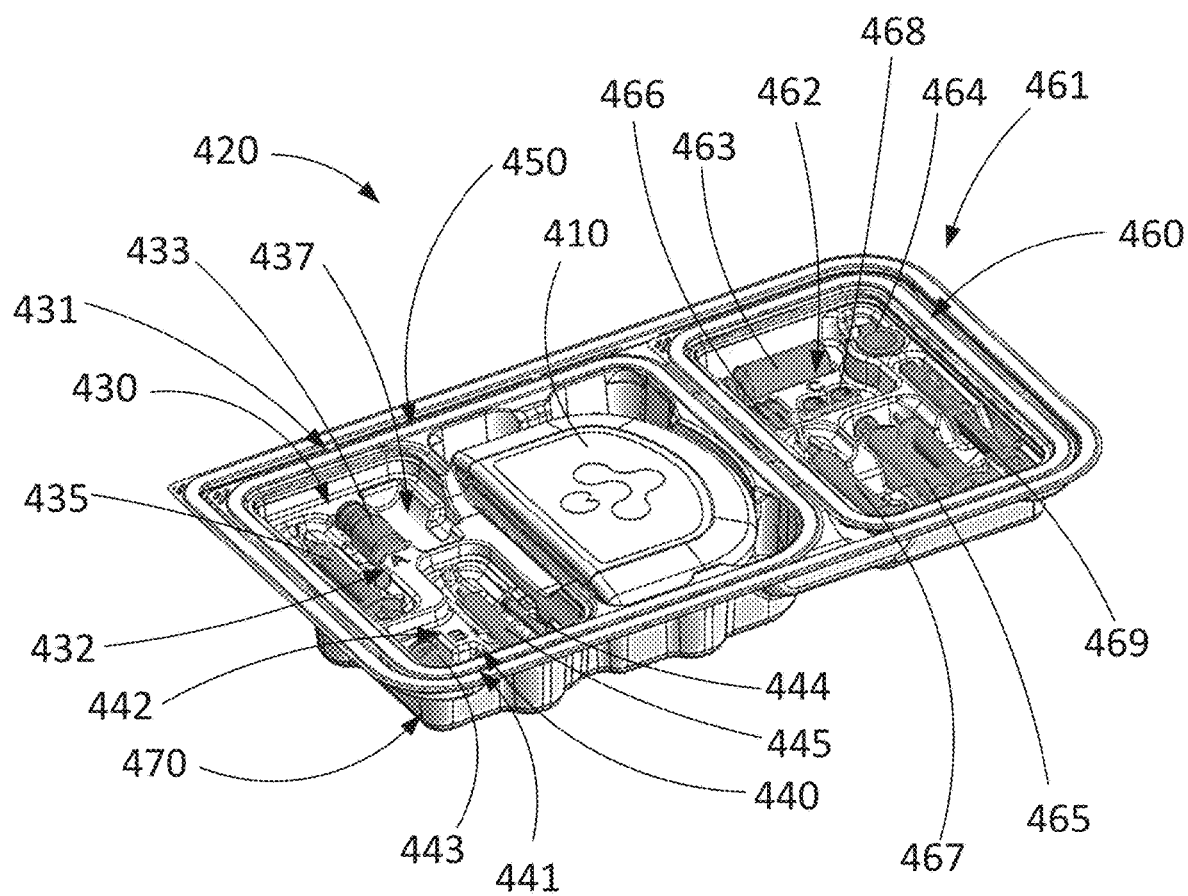

FIG. 10 is a perspective view of the housing 420 with the liner 436 removed from the integrated tray portion 450 and the liner 476 removed from the third housing portion 460. The first housing portion 430 and the second housing portion 440 may be integrally formed with each other to form one unitary structure (e.g., a tray). In some embodiments, the first and second housing portions may be removably coupled to one another as described above (e.g., via perforations). As shown in FIG. 10, the first housing portion 430 includes a first visual indicator 432 (e.g., the letter "A"), the second housing portion 440 includes a second visual indicator 442 (e.g., the letter "B"), and the third housing portion 460 includes a third visual indicator 462 (e.g., the letter "C"). These visual indicators may be molded into the housing portions, applied to the surface as decals or other suitable markings, or arranged on the housing portions in any suitable manner. Furthermore, these visual indicators may match or otherwise correspond to labels of device features as described below, and may associate the components arranged within the respective housing portions with respective portions of a tissue processing method.

The first housing portion 430 includes one or more recesses configured to receive a first set of components 431. For example, the first set of components 431 includes a vial 433 containing a volume of water (e.g., sterile water), a needle 434 (shown in FIG. 19), and an enzyme syringe 435. The first housing portion 430 defines a vial recess 437 configured to receive a vial containing enzyme. For example, the enzyme syringe 435 may be a 10 ml syringe. The needle 434 is configured to be coupled to the enzyme syringe 435. However, the first set of components 431 may include any suitable components appropriate for the tissue processing method. The recesses may be configured to receive the first set of components 431 via snap fit (e.g., the recesses may be sized and shaped with suitable tolerances to retain components that may be overcome with a suitable force) and/or one or more fasteners (e.g., elastics, straps, overhanging features, covers, etc.), and/or the like.

The second housing portion 440 includes one or more recesses configured to receive a second set of components 441. The second set of components 441 includes a vial 443 containing a buffer, a needle 444, and a buffer syringe 445. The needle 444 is configured to be coupled to the buffer syringe 445. The needle 444 may be, for example, a blunt fill needle. However, the second set of components 441 may include any suitable components appropriate for the tissue processing method. Like the recesses of the first housing portion 430, the recesses of the second housing portion 440 may be configured to receive the second set of components 441 via snap fit, one or more fasteners, and/or the like.

As shown in FIG. 10, the integrated tray 450 may further include a device recess configured to receive the device 410 (e.g., as described in further detail herein). The device recess may be sized and shaped with suitable tolerances to retain the deice via snap fit and/or one or more fasteners (e.g., elastics, straps, overhanging features, covers, etc.) and/or the like.

The third housing portion 460 includes one or more recesses configured to receive a third set of components 461. The third set of components 461 includes a vial 463 containing a buffer such as that described above, a cell strainer 464, a set of skin cell syringes 465, a set of needles 466, an unfiltered suspension syringe 467, a set of spray nozzles 468, and a pair of scalpels 469. The buffer vial 463 may include, for example, 30 ml of buffer. The set of skin cell syringes 465 may include any suitable number of syringes, such as four skin cell syringes (e.g., 10 ml syringes). The set of needles 466 may include any suitable number of needles, such as four needles (e.g., blunt fill needles stacked 2 by 2 in the third housing portion 460). The set of spray nozzles 468 may include any suitable number of spray nozzles, such as four spray nozzles. Each needle of the set of needles 466 may be coupled to a skin cell syringe of the set of skin cell syringes 465. Additionally, in the alternative to a needle from the set of needles 466, each spray nozzle of the set of spray nozzles 468 may be coupled to a skin cell syringe of the set of skin cell syringes 465. However, the third set of components 461 may include any suitable components appropriate for the tissue processing method. Like the recesses of the first housing portion 430, the recesses of the third housing portion 460 may be configured to receive the third set of components 461 via snap fit, one or more fasteners, and/or the like.

Figure 11:
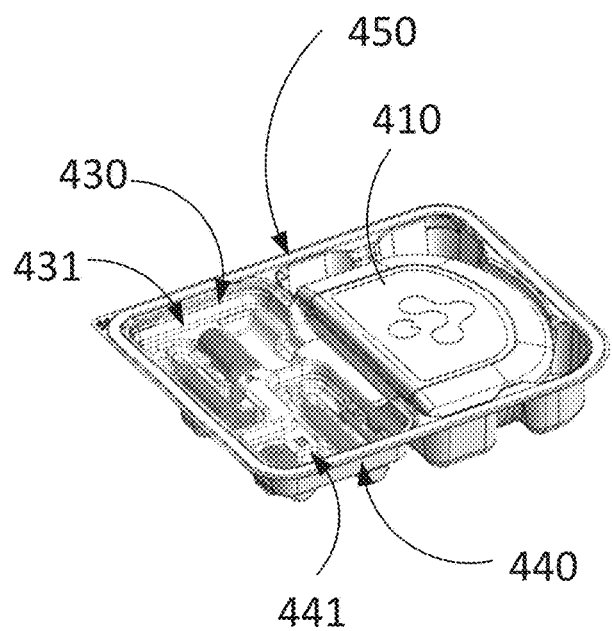
Figure 12:
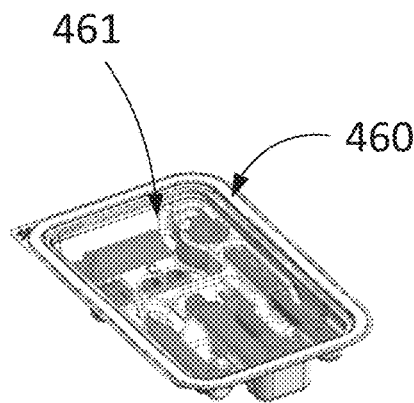
Figure 13:
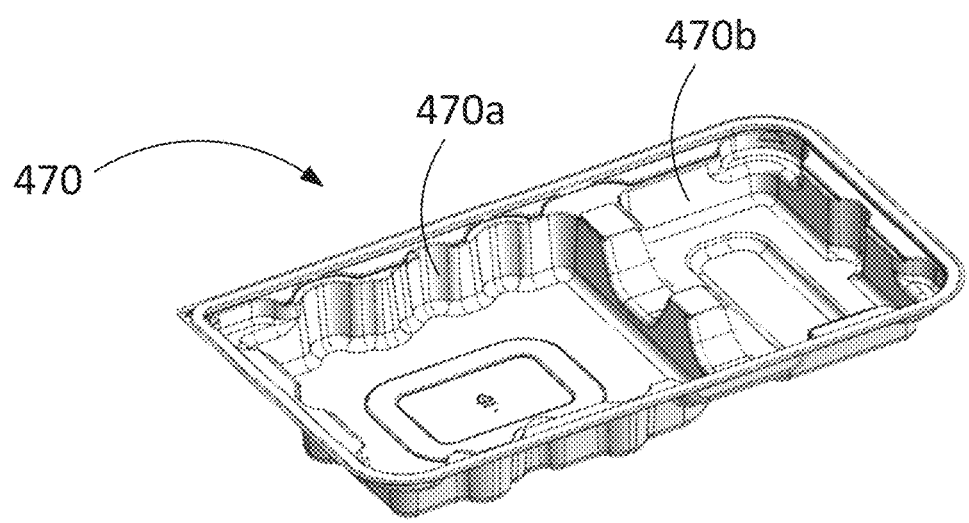

The integrated tray portion 450 and the third housing portion 460 may be removed from the base 470. For example, FIG. 11 is a perspective view of the integrated tray portion 450 after being removed from the base 470. The device 410, the first housing portion 430 including the first set of components 431, and the second housing portion 440 including the second set of components 441 are shown disposed in the integrated tray portion 450. FIG. 12 is a perspective view of the third housing portion 460 after being removed from the base 470 and including the third set of components 461. FIG. 13 is a perspective view of the base 470 separate from the other components of the kit 400. As shown, the base 470 defines a first recessed area 470a configured to receive the integrated tray portion 450 and a second recessed area 470b configured to receive the third housing portion 460 in a nested manner.

Figure 17:
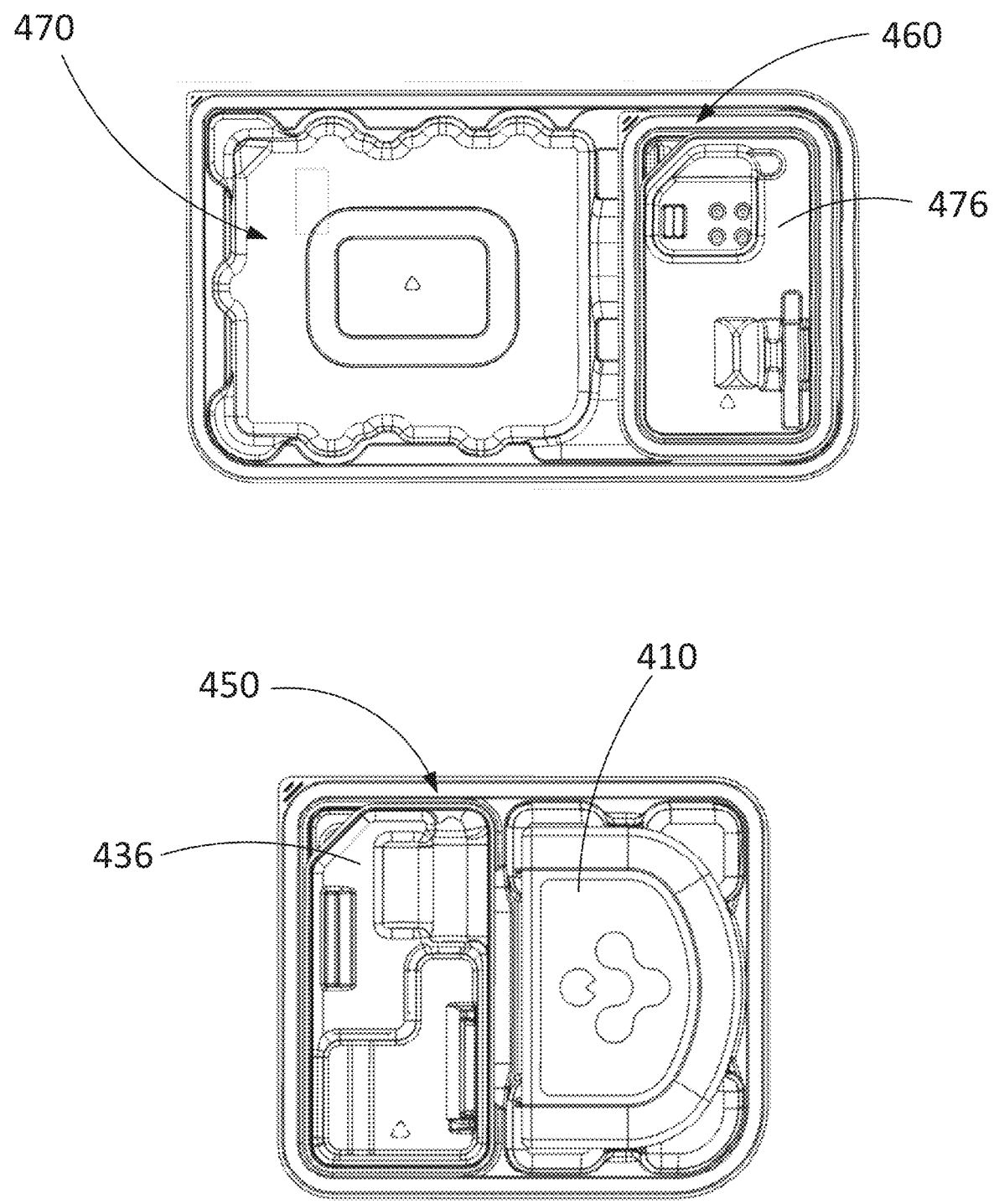

FIG. 17 is a top view of a partially disassembled housing, including the base 470 containing the third housing portion 460 with the liner 476, and the integrated tray portion 450 removed from the base 470. For example, the integrated tray portion 450 may be lifted out of the base 470 and transferred to a work area to aid in performance of a first and second portion of a tissue processing method.

Figure 18:
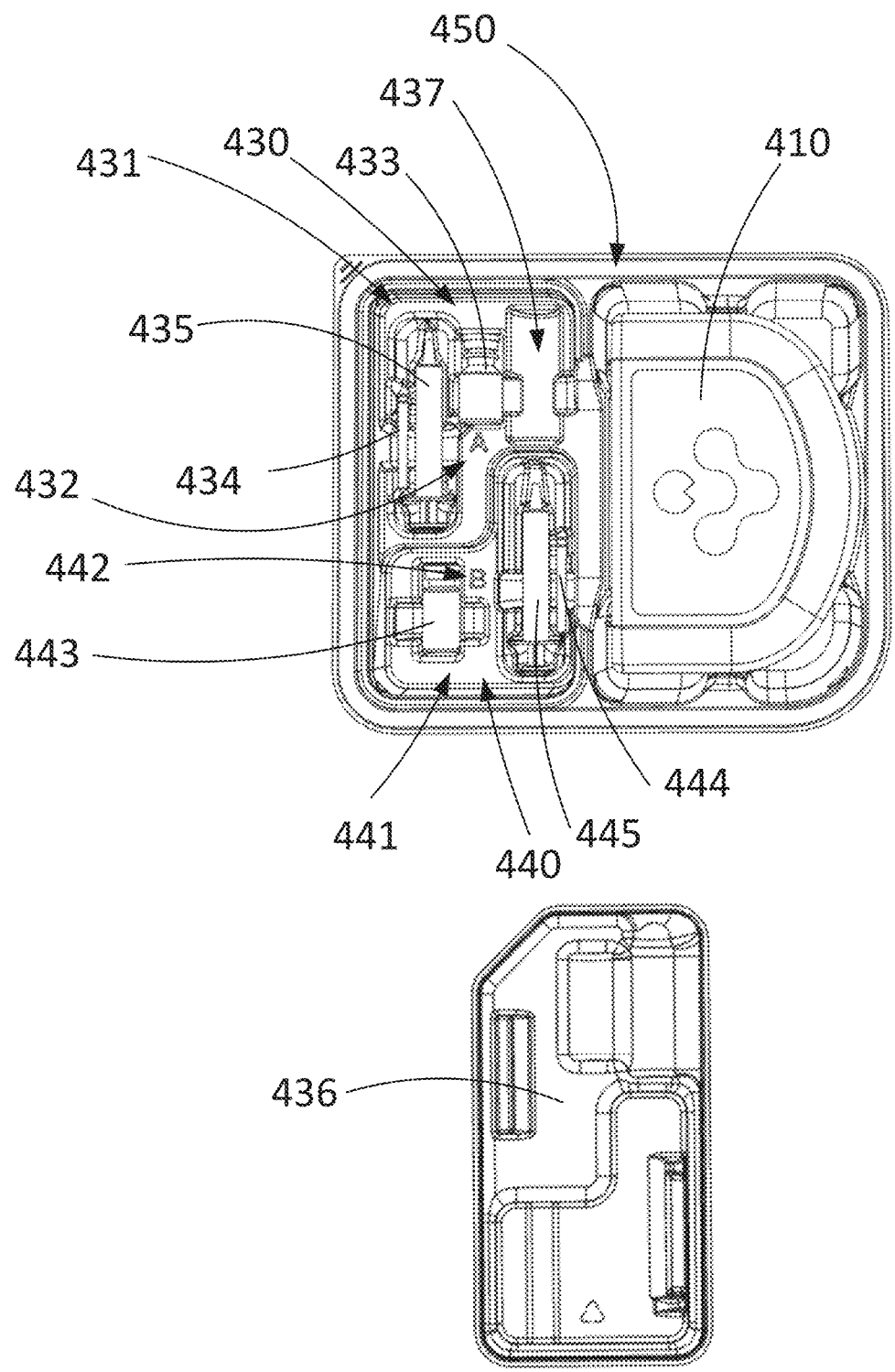
Figure 19:
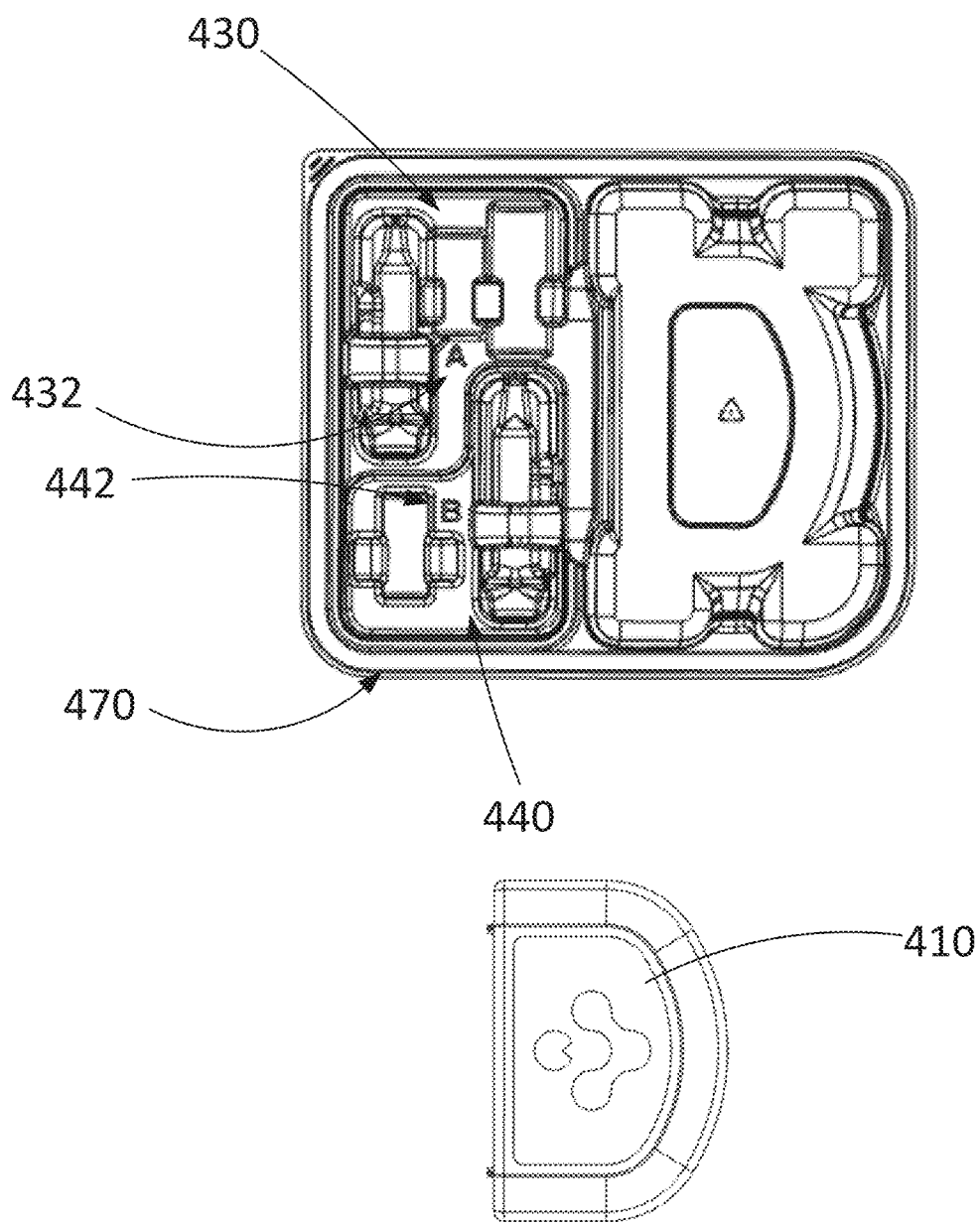

FIG. 18 is a top view of a partially disassembled housing, including the integrated tray portion 450 containing the first housing portion 430, the second housing portion 440, and the device 410, and the liner 436 removed and separated from the first housing portion 430 and the second housing portion 440. FIG. 19 is a top view of the integrated tray portion 450, with the first set of components 431 and the second set of components 443 removed from the integrated tray portion 450 and not shown, and with the device 410 removed and separated from the integrated tray portion 450.

Figure 23:
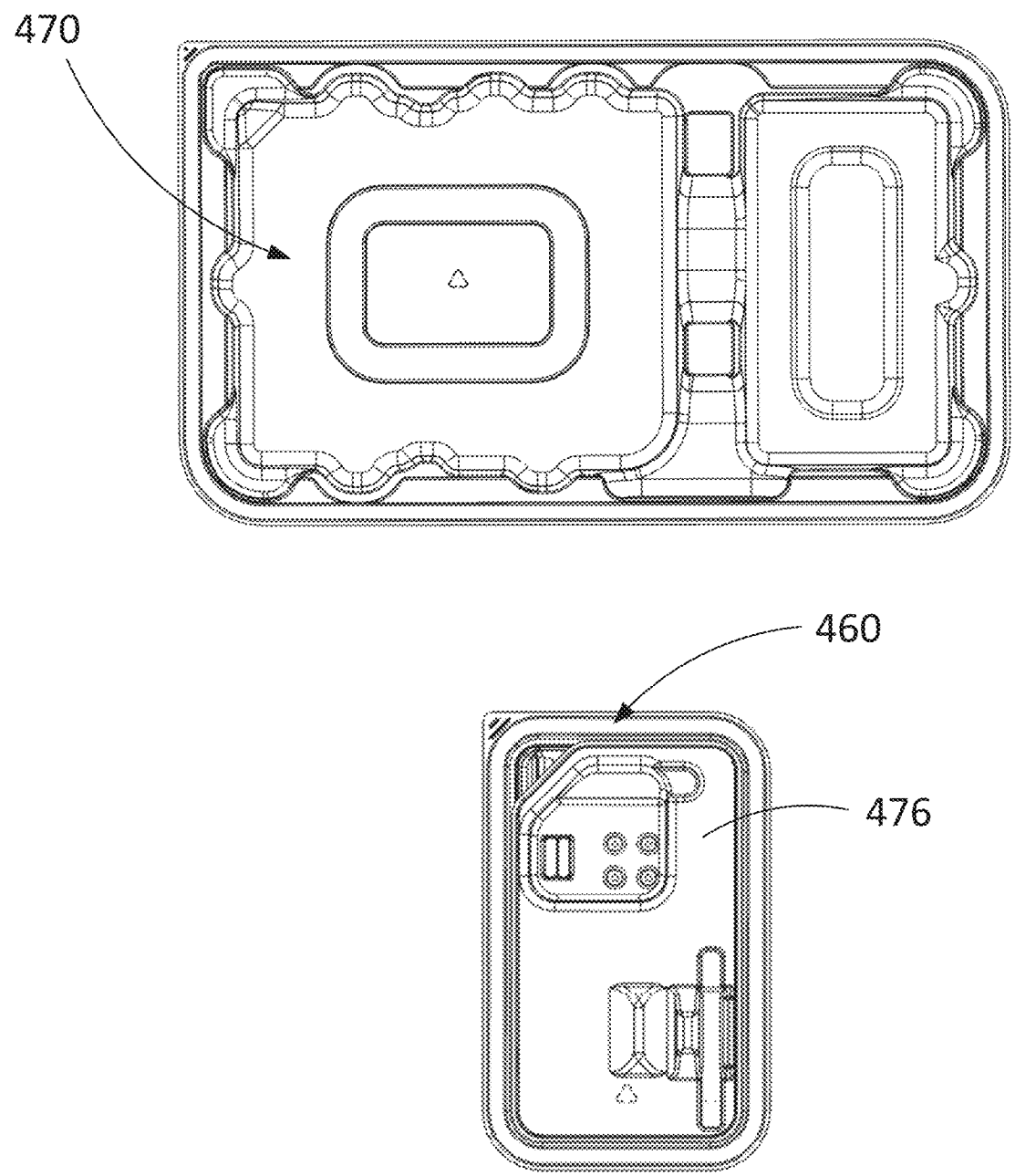
Figure 24:
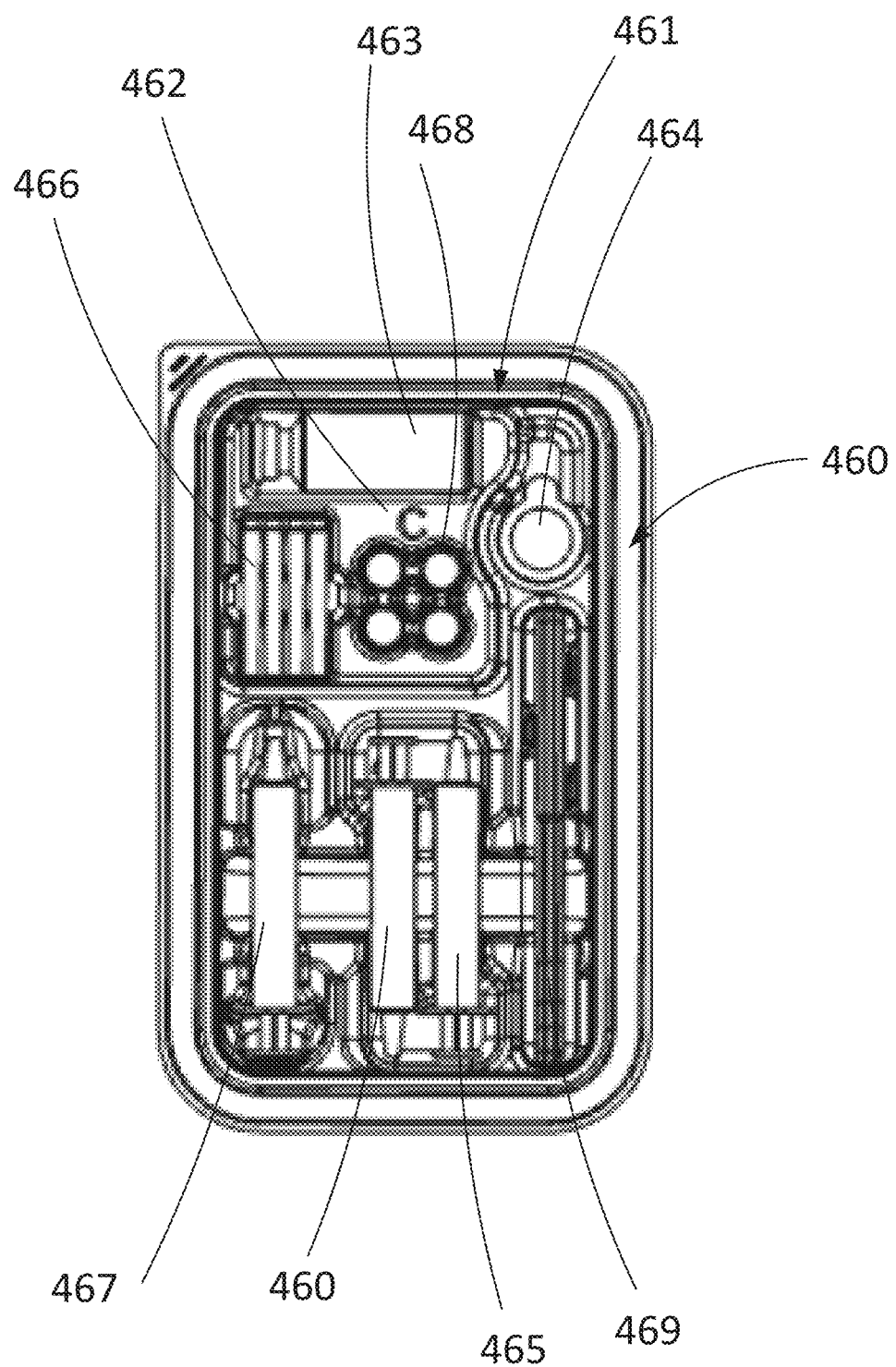

FIG. 23 is a top view of a partially disassembled housing, including the base 470 and the third housing portion 460 and its liner 476 removed and separated from the base 470. For example, the third housing portion 460 may be lifted out of the base 470 and transferred to a work area to aid in performance of a third portion of a tissue processing method. FIG. 24 is a top view of the third housing portion 460 with the liner 476 removed.

FIG. 14 is a top view of the device 410 with a cover portion of the device 410 removed. As shown, the device 410 includes a preparation tray 417 disposed in a recessed area 458 of the device 410. The device 410 also defines a first reservoir 411, a second reservoir 413, and a third reservoir 415. The device 410 also includes a first label 412, a second label 414, and a third label 416 (e.g., colored and labeled rings arranged around the reservoirs). The first label 412 may correspond to the first visual indicator 432 (e.g., by including a common color and/or the letter "A"), the second label 414 may correspond to the second visual indicator 442 (e.g., by including a common color and/or the letter "B"), and the third label 416 may correspond to the third visual indicator 462 (e.g., the letter "C"). FIG. 16 is a perspective view of an example embodiment of an enzyme vial 482. In some implementations, the first reservoir 411 may be configured to receive the enzyme vial 482. In some implementations, the first reservoir 411 may be configured to receive the contents of the enzyme vial 482 via a syringe.

The preparation tray 417 may include a bottom surface surrounded by sidewalls. A portion or all of the bottom surface may form a skin tissue manipulation area. The preparation tray 417 may include one or more collection areas 409, such as two collection areas on opposite sides of the preparation tray 417. The collection areas 409 may include surfaces that are recessed relative to other portions of the bottom surface of the preparation tray 417 such that fluid injected into the preparation tray 417 may flow and/or pool into the collection areas 409. FIG. 15 shows a top view of the device 410 with the preparation tray 417 removed from the recessed area 458. Other example features of the preparation tray 417 are described in further detail below.

Figure 20:
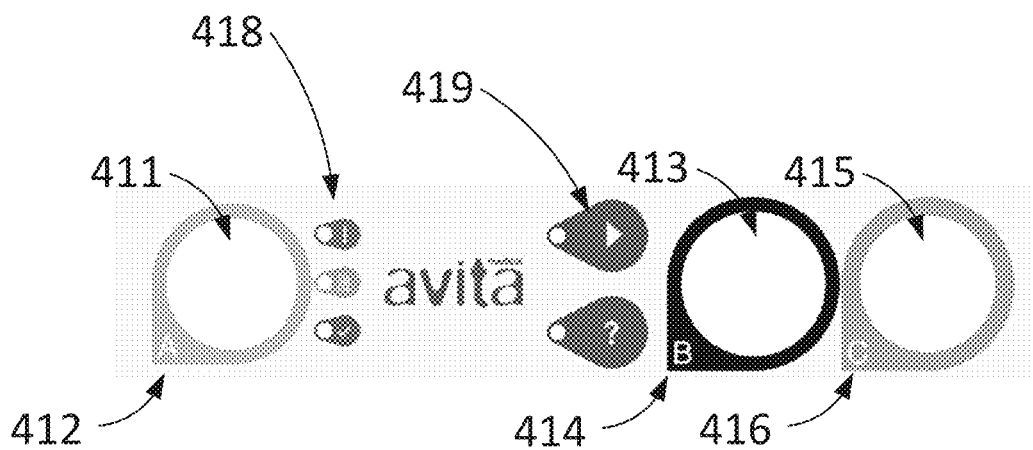
Figure 21:
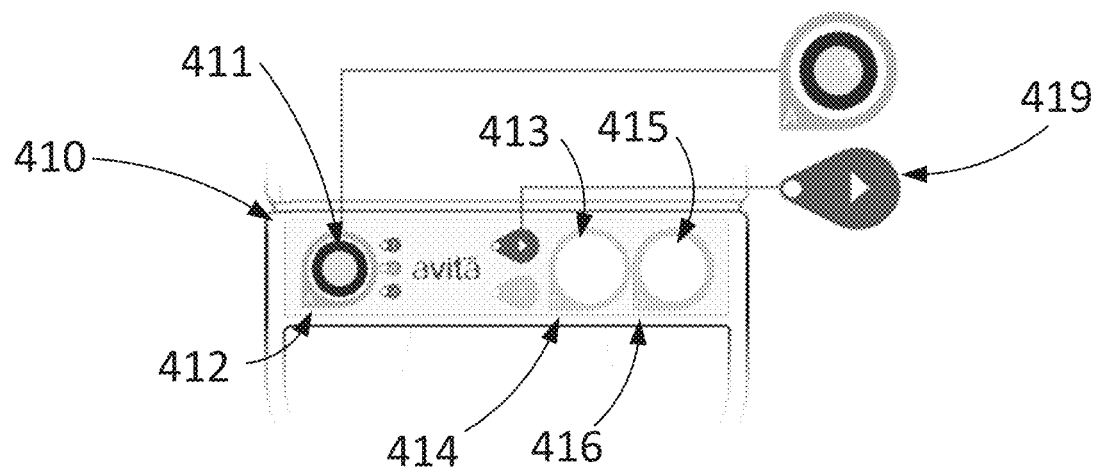

FIG. 20 is a view of a portion of the device 410. As shown, the first label 412 surrounds the first reservoir 411, the second label 414 surrounds the second reservoir 413, and the third label 416 surrounds the third reservoir 415. The device 410 may include various buttons, such as a button 419 which may be pressed to activate a heating assembly as described above with respect to the kit 100 of FIG. 1. Additionally, the device 410 may include a set of one or more heating assembly indicators 418. The one or more heating assembly indicators 418 may include indicators configured to be associated with indicator lights of the device to indicate one or more statuses of the device 410 (e.g., one or more statuses of the heating assembly of the device 410) as described above with respect to the kit 100 of FIG. 1. FIG. 21 shows the portion of the device 410 shown in FIG. 20 disposed on the device 410 (e.g., adjacent a preparation tray for manipulating tissue).

Figure 22:
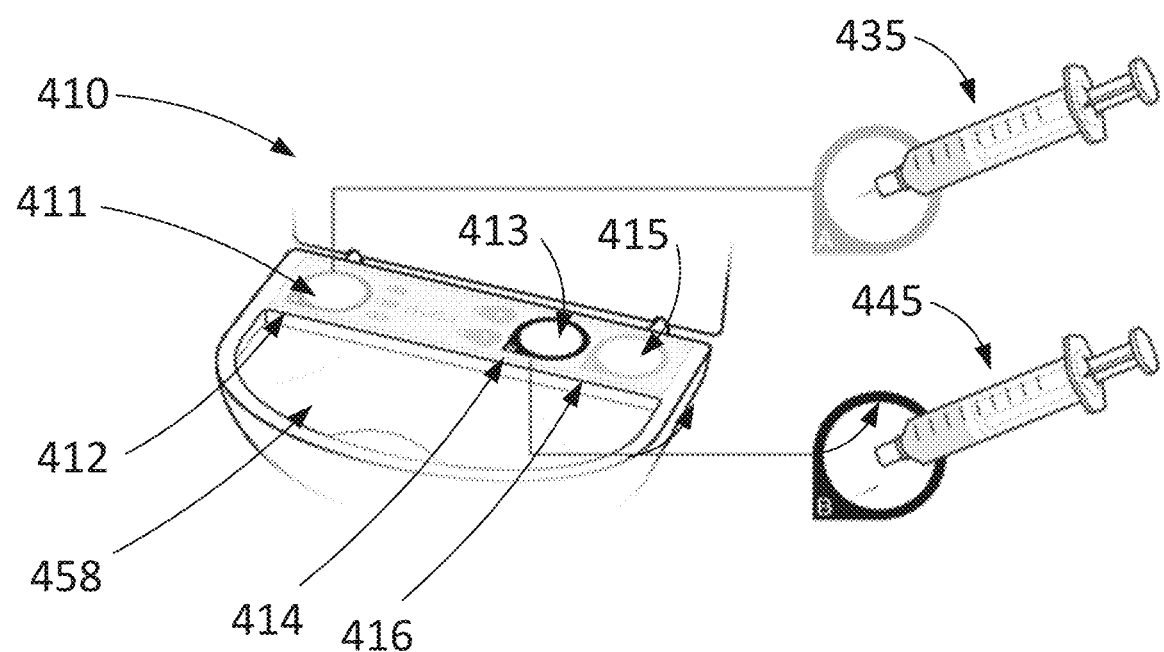

FIG. 22 is a perspective view of the device 410 with portions enlarged to show an intended relationship between the enzyme syringe 435 of the first set of components 430 and the first reservoir 411 and an intended relationship between the buffer syringe 445 of the second set of components 440 and the second reservoir 413.

Figure 25:
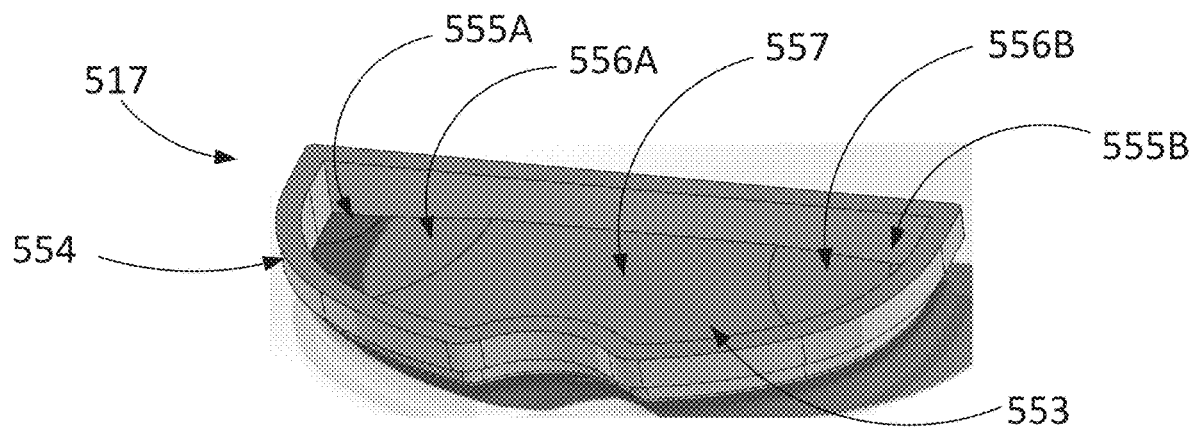
FIGS. 25 and 26 are a perspective view and a cross-sectional view, respectively, of a preparation tray, according to an embodiment.
Figure 26:
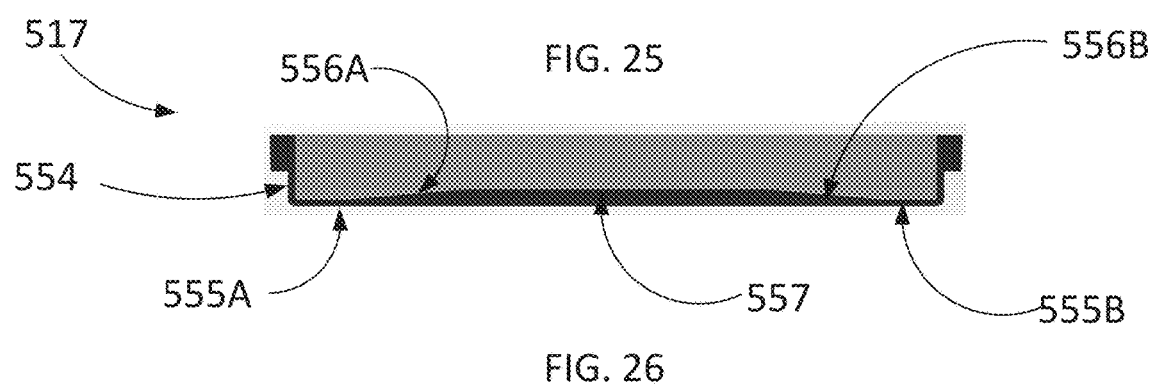

The preparation tray of any of the devices described herein (e.g., the device 110, the device 210, and the device 410) may have any suitable bottom surface shape and contour such that fluid collection from the preparation tray (e.g., via a syringe needle) may be effective. For example, FIGS. 25 and 26 are a perspective view and a cross-sectional view of a preparation tray 517, respectively. The preparation tray 517 includes a bottom surface 553 surrounded by sidewalls 554 around its perimeter. The bottom surface 553 includes a primary surface 557, a first lower surface 555A, and a second lower surface 555B. The primary surface 557 may be or include a skin tissue manipulation area. The bottom surface 553 also includes a first transition surface 556A that tapers and slopes downward from the primary surface 557 to the first lower surface 555A. The bottom surface 553 also includes a second transition surface 556B that tapers and slopes downward from the primary surface 557 to the second lower surface 555B. As depicted in FIG. 26, the first and second transition surfaces are shown as having linear slopes; however, it should be understood that in some embodiments the transition may be curved (e.g., convex, concave, etc.) or have any suitable shape. Furthermore, in some embodiments the transition surfaces 556A and 556B may extend into respective corners or edges of the preparation tray 517 (e.g., omitting the lower surfaces 555A and 555B). The first lower surface 555A and/or the first transition surface 556A may collectively define a first collection area and the second lower surface 555B and/or the second transition surface 556B may collectively define a second collection area such that fluid may flow from the primary surface 557 into one or both of the first collection area and the second collection area. The first collection area and the second collection area may be disposed on opposite ends of the preparation tray 517 (e.g., to help facilitate easy tissue collection for both left-handed and right-handed users). In some embodiments, the preparation tray may additionally or alternatively include a collection area on the front region and/or back region of the preparation tray 517 using similar transition and lower surfaces as shown in FIGS. 25 and 26. Although the preparation tray 517 is shown as having a substantially semi-circular or half-moon shape, the preparation tray 517 may have any suitable shape (e.g., ovular, rectangular, circular).

Figure 27:
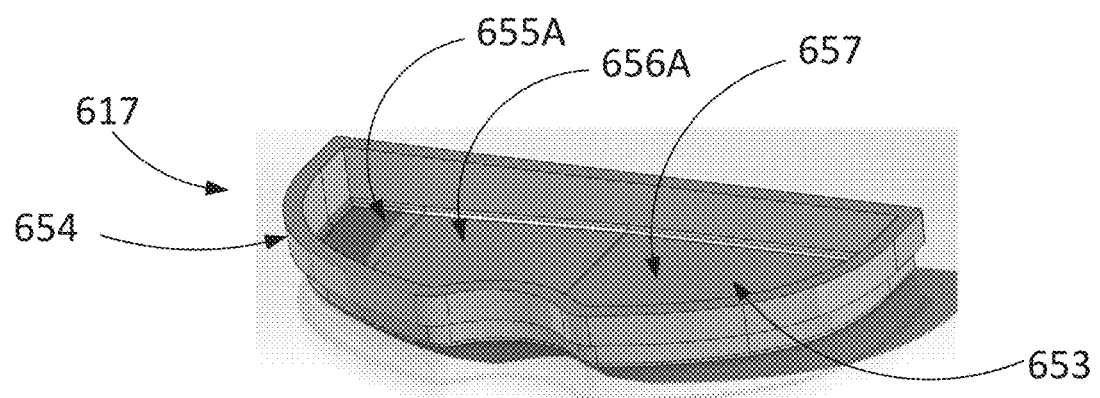
FIGS. 27 and 28 are a perspective view and a cross-sectional view, respectively, of a preparation tray, according to an embodiment.
Figure 28:
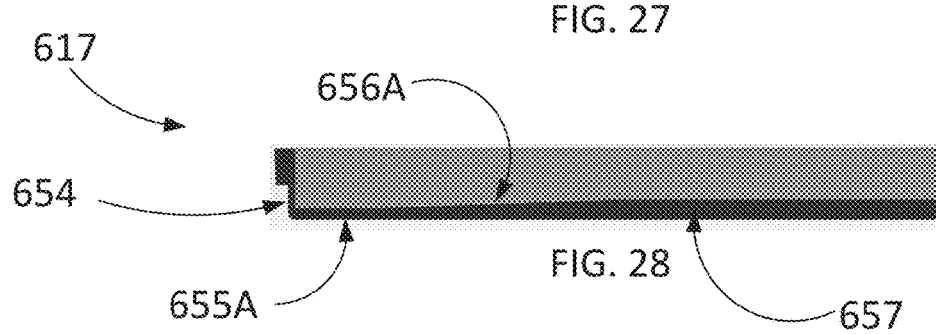

FIGS. 27 and 28 are a perspective view and a cross-sectional view of a preparation tray 617, respectively. The preparation tray 617 includes a bottom surface 653 surrounded by sidewalls 654 around its perimeter. The bottom surface 653 includes a primary surface 657, a lower surface 655A, and a transition surface 656A that tapers and slopes downward from the primary surface 657 to the first lower surface 655A. As depicted in FIG. 28, the transition surface 656A is shown as having a generally linear slope; however, it should be understood that in some embodiments the transition may be curved (e.g., convex, concave, etc.) or have any suitable shape. Furthermore, in some embodiments the transition surface 656A may extend into a corner or edge of the preparation tray 617 (e.g., omitting the lower surface 655A). The primary surface 657 may be or include a skin tissue manipulation area. The lower surface 655A and/or the transition surface 656A may collectively define a collection area such that fluid may flow from the primary surface 657 into the collection area. The lower surface 655A is shown in FIGS. 27 and 28 as being arranged on a left side of the preparation tray, but it should be understood that in some embodiments a similar lower surface 655A may be arranged on a right side of the preparation tray in a mirrored manner. Furthermore, in some embodiments, the preparation tray may additionally or alternatively include a collection area on the front region and/or back region of the preparation tray 617 using similar transition and lower surfaces as shown in FIGS. 27 and 28. Although the preparation tray 617 is shown as having a substantially semi-circular or half-moon shape, the preparation tray 617 may have any suitable shape (e.g., ovular, rectangular, circular).

Figure 29:
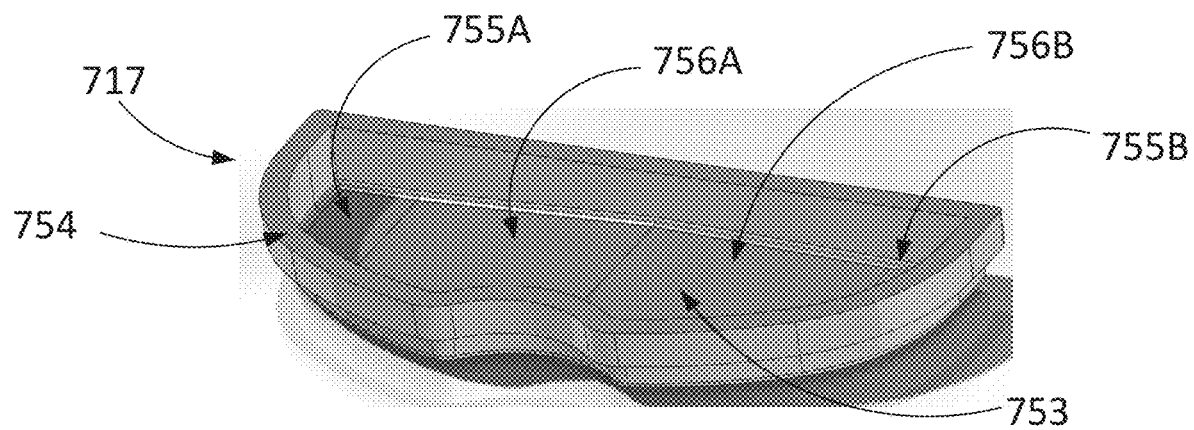
FIGS. 29 and 30 are a perspective view and a cross-sectional view, respectively, of a preparation tray, according to an embodiment.
Figure 30:
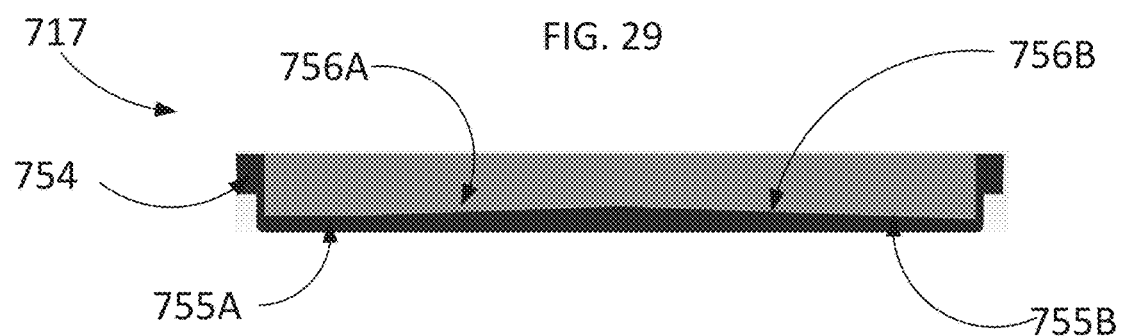

FIGS. 29 and 30 are a perspective view and a cross-sectional view of a preparation tray 717, respectively. The preparation tray 717 may be similar to preparation tray 517 described above with respect to FIGS. 25 and 26, except that preparation tray 717 omits the primary surface 557. The preparation tray 717 includes a bottom surface 753 surrounded by sidewalls 754 around its perimeter. The bottom surface 753 includes a first lower surface 755A and a second lower surface 755B. The bottom surface 753 also includes a first transition surface 756A that tapers and slopes downward from a midline of the preparation tray toward the first lower surface 755A. The bottom surface 753 also includes a second transition surface 756B that tapers and slopes downward from the midline of the preparation tray (e.g., an upper edge of the first transition surface 756A) to the second lower surface 755B. Alternatively, the first transition surface 756A and/or the second transition surface 756B may have upper edges that are not coincident with the midline of the preparation tray, such that their upper edges are offset (e.g., angled, laterally displaced, etc.) from the midline of the preparation tray, thereby making either the first transition surface 756A or the second transition surface 756B larger than the other transition surface. Additionally, it should be understood than in some embodiments, one or both transition surfaces may be curved (e.g., convex, concave, etc.) or have any suitable shape. Furthermore, in some embodiments one or both transition surfaces may extend into a corner or edge of the preparation tray 717 (e.g., omitting the lower surfaces 755A and/or 75B. The first transition surface 756A and the second transition surface 756B may each be or include a skin tissue manipulation area. The first lower surface 755A and/or the first transition surface 756A may collectively define a first collection area and the second lower surface 755B and/or the second transition surface 756B may collectively define a second collection area such that fluid may flow into one or both of the first collection area and the second collection area. The first collection area and the second collection area may be disposed on opposite ends of the preparation tray 717. Furthermore, in some embodiments, the preparation tray may additionally or alternatively include a collection area on the front region and/or back region of the preparation tray 717 using similar transition and lower surfaces as shown in FIGS. 29 and 30. Although the preparation tray 717 is shown as having a substantially semi-circular or half-moon shape, the preparation tray 717 may have any suitable shape (e.g., ovular, rectangular, circular).

Figure 31:
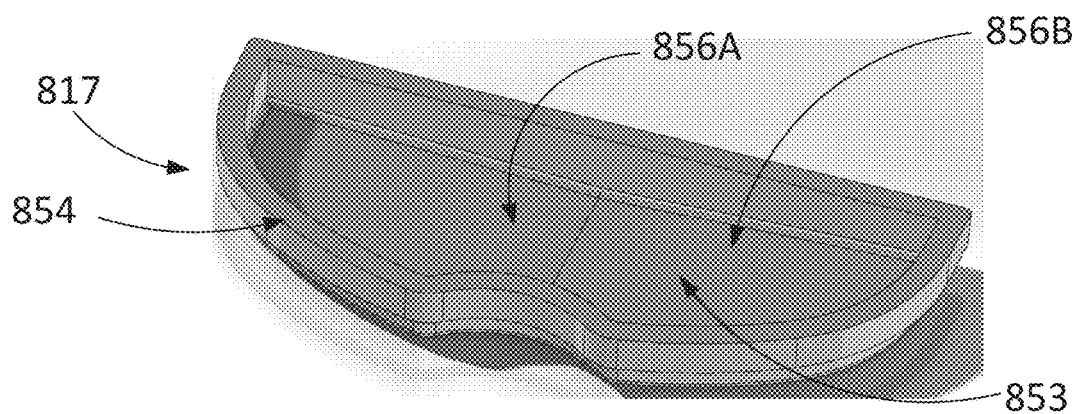
FIGS. 31 and 32 are a perspective view and a cross-sectional view, respectively, of a preparation tray, according to an embodiment.
Figure 32:
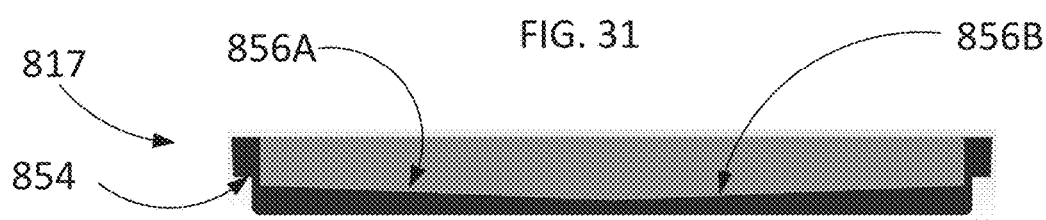

While FIGS. 25-30 depict example embodiments of preparation trays having at least one collection area on a lateral portion (e.g., left side, right side) of the preparation tray, in some embodiments the preparation tray may include one or more collection areas arranged in other areas of the tray. For example, FIGS. 31 and 32 are a perspective view and a cross-sectional view of a preparation tray 817, respectively, where the preparation tray 817 includes a collection area positioned in a central region of the preparation tray 817. The preparation tray 817 includes a bottom surface 853 surrounded by sidewalls 854 around its perimeter. The bottom surface 853 includes a first transition surface 856A that tapers and slopes downward from a first end of the preparation tray 817 toward a center of the preparation tray 817 and a second transition surface 856B that tapers and slopes downward from a second end of the preparation tray 817 toward the center of the preparation tray 817 (e.g., a lower edge of the first transition surface 856A). Alternatively, the first transition surface 856A and/or the second transition surface 856B may have lower edges that are not coincident with the midline of the preparation tray, such that their lower edges are offset (e.g., angled, laterally displaced, etc.) from the midline of the preparation tray, thereby making either the first transition surface 856A or the second transition surface 856B larger than the other transition surface. Additionally, it should be understood than in some embodiments, one or both transition surfaces may be curved (e.g., convex, concave, etc.) or have any suitable shape. The first transition surface 856A and the second transition surface 856B may each be or include a skin tissue manipulation area. The first transition surface 856A and the second transition surface 856B may collectively define a collection area such that fluid may flow toward the intersection of the first transition surface 856A with the second transition surface 756B. Furthermore, in some embodiments, the preparation tray may additionally or alternatively include a collection area on the front region and/or back region of the preparation tray 817 using similar transition and lower surfaces as shown in FIGS. 31 and 32. Although the preparation tray 717 is shown as having a substantially semi-circular or half-moon shape, the preparation tray 717 may have any suitable shape (e.g., ovular, rectangular, circular).

Figure 33:
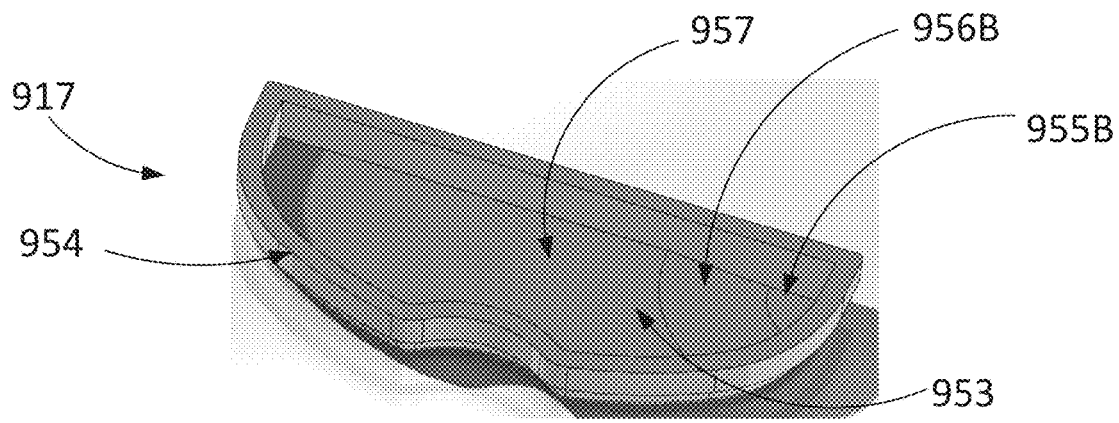
FIGS. 33 and 34 are a perspective view and a cross-sectional view, respectively, of a preparation tray, according to an embodiment.
Figure 34:
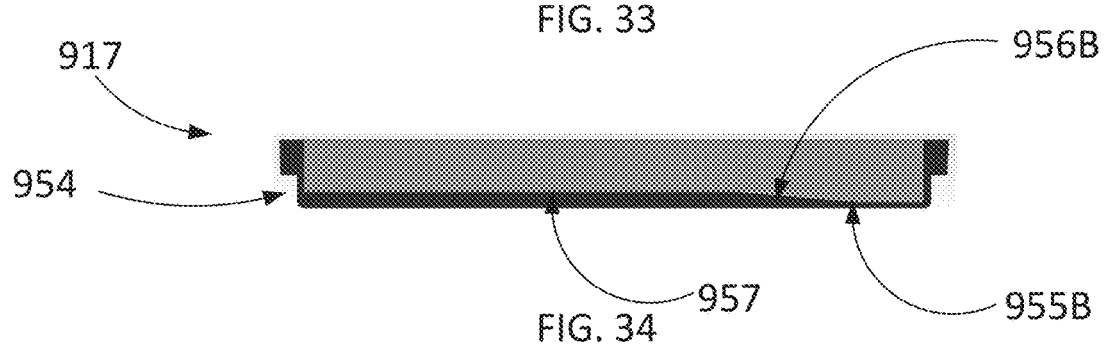

FIGS. 33 and 34 are a perspective view and a cross-sectional view of a preparation tray 917, respectively. The preparation tray 917 includes a bottom surface 953 surrounded by sidewalls 954 around its perimeter. The bottom surface 953 includes a primary surface 957, a lower surface 955B, and a transition surface 956B. The primary surface 957 may be or include a skin tissue manipulation area. The transition surface 956A tapers or slopes downward from the primary surface 957 to the lower surface 955A. As depicted in FIG. 34, the transition surface 956B is shown as having a generally linear slope; however, it should be understood that in some embodiments the transition may be curved (e.g., convex, concave, etc.) or have any suitable shape. The lower surface 955A and the transition surface 956A may collectively define a collection area such that fluid may flow from the primary surface 957 into the first collection area. The collection area may be disposed on an end and/or in a corner of the preparation tray 917. Although the collection area in the preparation tray shown in FIGS. 33 and 34 is on the right side of the preparation tray 917, in some embodiments the collection area may be on the left side (or front or back, etc.) of the preparation tray in a similar manner. Although the preparation tray 917 is shown as having a substantially semi-circular or half-moon shape, the preparation tray 917 may have any suitable shape (e.g., ovular, rectangular, circular).

Figure 35:
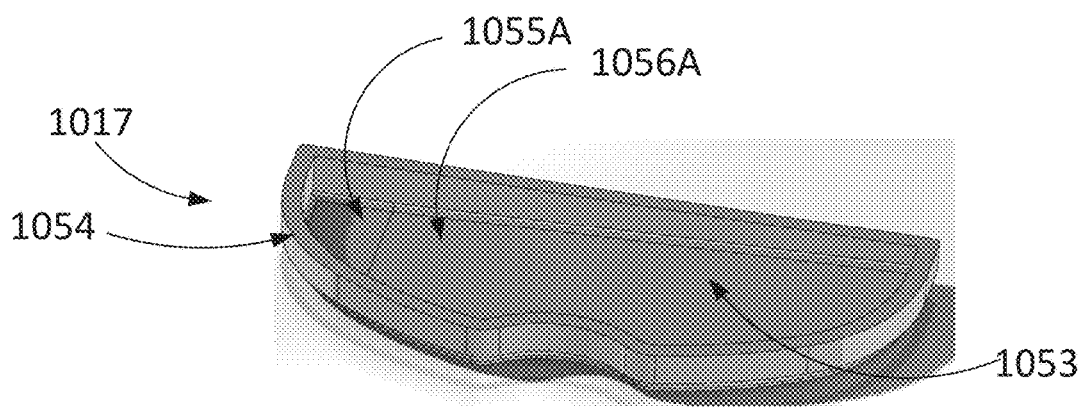
FIGS. 35 and 36 are a perspective view and a cross-sectional view, respectively, of a preparation tray, according to an embodiment.
Figure 36:
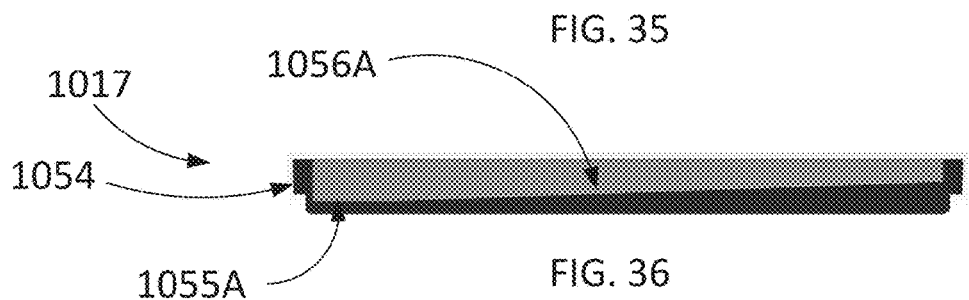

FIGS. 35 and 36 are a perspective view and a cross-sectional view of a preparation tray 1017, respectively. The preparation tray 1017 includes a bottom surface 1053 surrounded by sidewalls 1054 around it perimeter. The bottom surface 1053 includes a lower surface 1055A and a transition surface 1056A that tapers or slopes downward from a first end of the bottom surface 1053 to the first lower surface 1055A disposed at a second end of the preparation tray 1017. As depicted in FIG. 36, the transition surface 1056A is shown as having a generally linear slope; however, it should be understood that in some embodiments the transition may be curved (e.g., convex, concave, etc.) or have any suitable shape. The transition surface 1056A may be or include a skin tissue manipulation area. The lower surface 1055A and the transition surface 1056A may collectively define a collection area such that fluid may flow toward the collection area. Although the collection area in the preparation tray shown in FIGS. 35 and 36 is on the left side of the preparation tray 1017, in some embodiments the collection area may be on the left side (or front or back, etc.) of the preparation tray in a similar manner. Although the preparation tray 1017 is shown as having a substantially semi-circular or half-moon shape, the preparation tray 1017 may have any suitable shape (e.g., ovular, rectangular, circular).

Additionally or alternatively, in some embodiments the preparation tray may include at least one textured surface. The at least one textured surface may be arranged on a skin tissue manipulating area of the preparation tray, such that a skin sample may be scraped, pressed, or otherwise forced against the textured surface to help mechanically disaggregate the skin sample. In some embodiments, the at least one textured surface may include one or more raised features. For example, the one or more raised features may have a height between about 0.05 mm and about 2 mm, between about 0.05 mm and about 1.5 mm, between 0.05 mm and about 1 mm, between about 0.1 mm and about 2 mm, between about 0.1 mm and about 1.5 mm, or between about 0.1 mm and about 1 mm. In some embodiments, the at least one textured surface may additionally or alternatively include one or more recessed features. For example, the one or more recessed features may have a depth between about between about 0.05 mm and about 2 mm, between about 0.05 mm and about 1.5 mm, between 0.05 mm and about 1 mm, between about 0.1 mm and about 2 mm, between about 0.1 mm and about 1.5 mm, or between about 0.1 mm and about 1 mm. In some embodiments, the one or more raised features and/or the one or more recessed features may have a width or depth between about 0.05 and about 1 mm, between about 0.05 mm and about 0.5 mm, or between about 0.5 mm and about 1 mm.

Figure 37:
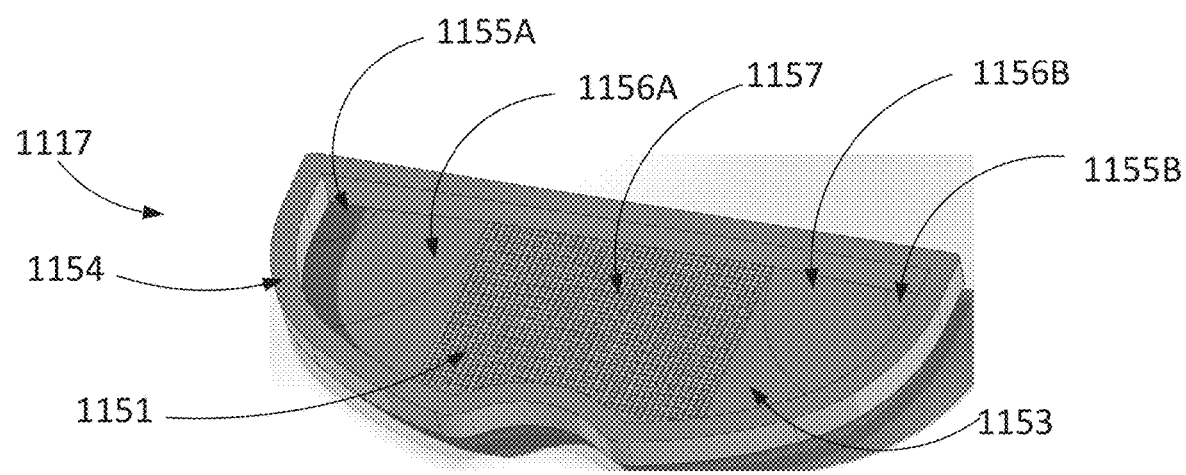
FIG. 37 is a perspective view of a preparation tray, according to an embodiment.

For example, as shown in FIG. 37, the skin tissue manipulation area 1151 may include a set of one or more raised textural features arranged in a two-dimensional array. At least one of the raised features may be columnar (e.g., circular cross-section, other polygonal cross-section), and/or at least one of the raised features may be tapered (e.g., pyramidal, domed, etc.), or have any suitable shape. For example, in some embodiments, some or all of the raised features may taper so as to have an uppermost point. Such tapered features may, in some features, have a height and/or width similar to that described above. The set of raised features may be arranged in any suitable manner, such as a rectangular array as shown in FIG. 37, or a triangular array, hexagonal array, irregular or random array, etc. Similarly, in some embodiments a preparation tray may additionally or alternatively include a set of recessed features (e.g., dimples) arranged in a rectangular array similar to that shown in FIG. 37, and/or any suitable array. While for sake of illustration FIG. 37 depicts a textured surface on a preparation tray having two collection areas similar to that described above with respect to FIGS. 25 and 26, it should be understood that any preparation tray (e.g., preparation trays described above with respect to FIGS. 25-36) may include at least one textured surface with raised features and/or recesses similar to that described above with respect to FIG. 37.

Figure 38:
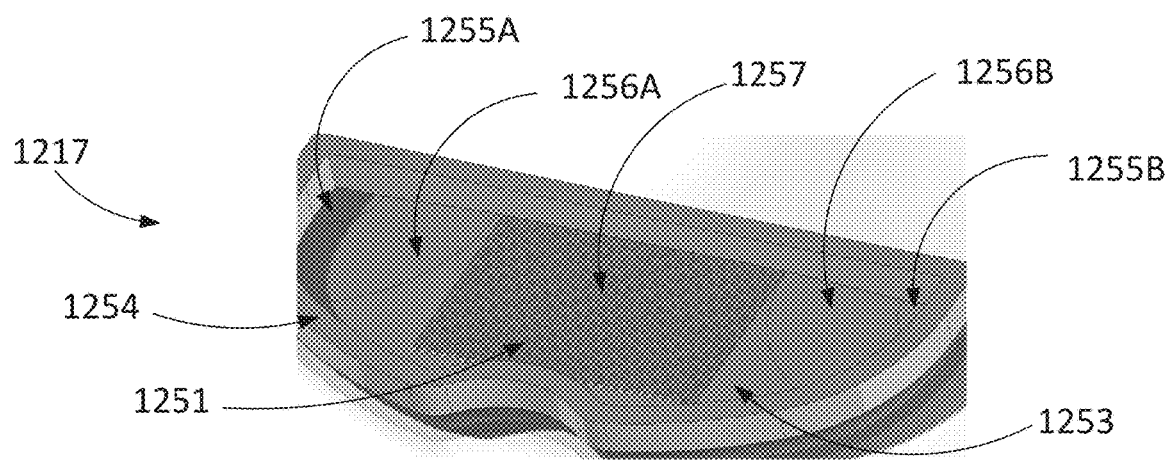
FIG. 38 is a perspective view of a preparation tray, according to an embodiment.

As another example of a preparation tray with a textured surface, FIG. 38 is a perspective view of a preparation tray 1217 including a skin manipulation area 1251 including one or more raised textural features arranged in a one-dimensional array. For example, as shown in FIG. 38, the skin tissue manipulation area may include one or more elongated ridges (e.g., parallel ridges). In some embodiments, the one or more elongated ridges may be generally prismatic (e.g., rectangular prismatic), angled (e.g., slanted fins), or may be domed (e.g., curvilinear in cross-sectional profile). The elongated ridges may be arranged parallel to one another, or in any suitable manner (e.g., angled or non-parallel, random, etc.). Similarly, in some embodiments a preparation tray may additionally or alternatively include a set of recessed features (e.g., trenches) arranged in a manner similar to that shown in FIG. 38, and/or any suitable array. Furthermore, while for sake of illustration FIG. 38 depicts a textured surface on a preparation tray having two collection areas similar to that described above with respect to FIGS. 25 and 26, it should be understood that any preparation tray (e.g., preparation trays described above with respect to FIGS. 25-36) may include at least one textured surface with raised features and/or recesses similar to that described above with respect to FIG. 38.

Figure 39:
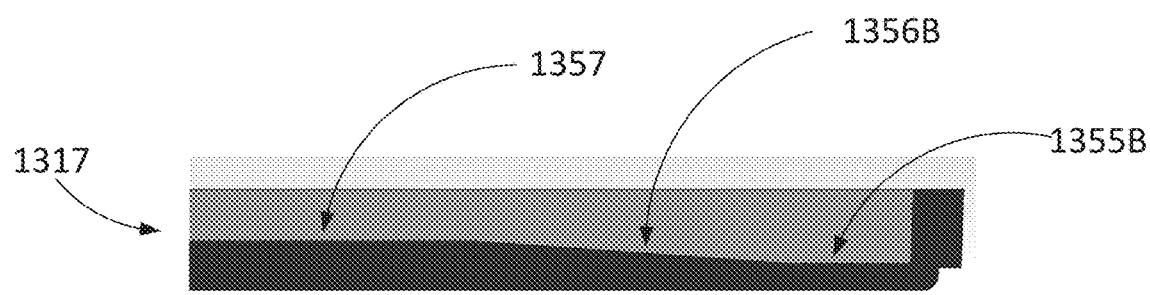
FIG. 39 is a portion of a cross-sectional view of a preparation tray according to an embodiment.

The transition surfaces of the preparation trays described herein may have any suitable taper or slope angle for directing flow of cells toward one or more suitable collection areas of the preparation trays. In some embodiments, the slope or grade of a preparation tray may be between about 0.5 degrees and about 35 degrees, between about 0.5 degrees and about 25 degrees, between about 0.5 degrees and about 15 degrees, between about 5 degrees and about 35 degrees, between about 5 degrees and about 25 degrees, between about 5 degrees and about 15 degrees, between about 15 degrees and about 35 degrees, or between about 15 degrees and about 25 degrees. In some embodiments the suitable slope may vary depending on factors including, for example, properties (e.g., hydrophobic properties) of the material and/or surface coating of the preparation tray. For example, a preparation tray having a highly hydrophobic material and/or surface coating may have a shallower transition surface sufficient for directing flow of cells toward a collection area. For example, FIG. 39 is a portion of a cross-sectional view of a preparation tray 1317. The preparation tray 1317 may be the same or similar in structure and/or function to any of the preparation trays described herein, such as the preparation tray 517. For example, the preparation tray 1317 includes a primary surface 1357, a lower surface 1355B, and a transition surface 1356B tapering from the primary surface 1357 to the lower surface 1355B. The transition surface 1356B tapers from the primary surface 1357 to the lower surface 1355B at a four degree angle relative to the primary surface 1357.

Figure 40:
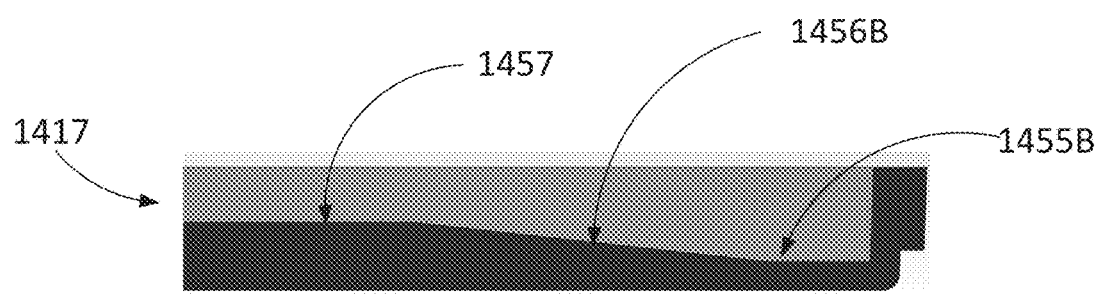
FIG. 40 is a portion of a cross-sectional view of a preparation tray according to an embodiment.

FIG. 40 is a portion of a cross-sectional view of a preparation tray 1417. The preparation tray 1417 may be the same or similar in structure and/or function to any of the preparation trays described herein, such as the preparation tray 517. For example, the preparation tray 1417 includes a primary surface 1457, a lower surface 1455B, and a transition surface 1456B tapering from the primary surface 1457 to the lower surface 1455B. The transition surface 1456B tapers from the primary surface 1457 to the lower surface 1455B at a four degree angle relative to the primary surface 1457.

Figure 41:
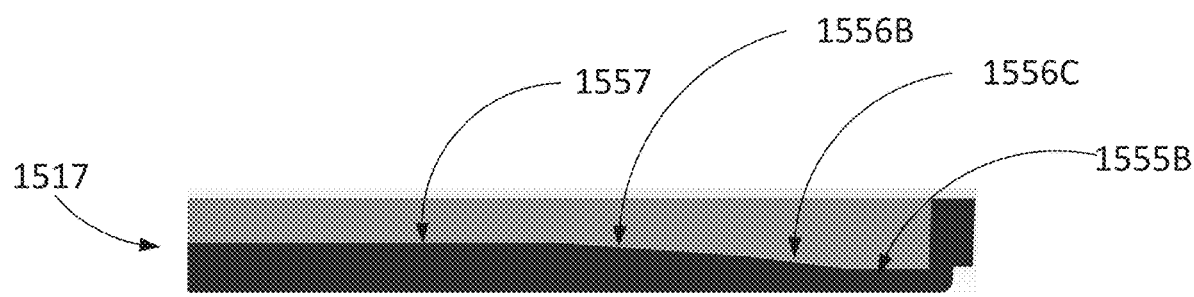
FIG. 41 is a portion of a cross-sectional view of a preparation tray according to an embodiment.

FIG. 41 is a portion of a cross-sectional view of a preparation tray 1517. The preparation tray 1517 may be the same or similar in structure and/or function to any of the preparation trays described herein, such as the preparation tray 517. For example, the preparation tray 1517 includes a primary surface 1557, a lower surface 1555B, a first transition surface 1556B, and a second transition surface 1556C. The first transition surface 1556B may taper at a first angle from the primary surface 1557 to the second transition surface 1556C. The second transition surface 1556C may taper at a second angle from the first transition surface 1556B to the lower surface 1555B. The first transition surface 1556B tapers from the primary surface 1557 to the second transition surface 1556C at a four degree angle relative to the primary surface 1557. The second transition surface 1556C tapers from the first transition surface 1556B to the lower surface 1555B at a seven degree angle relative to the primary surface 1557.

Figure 59:
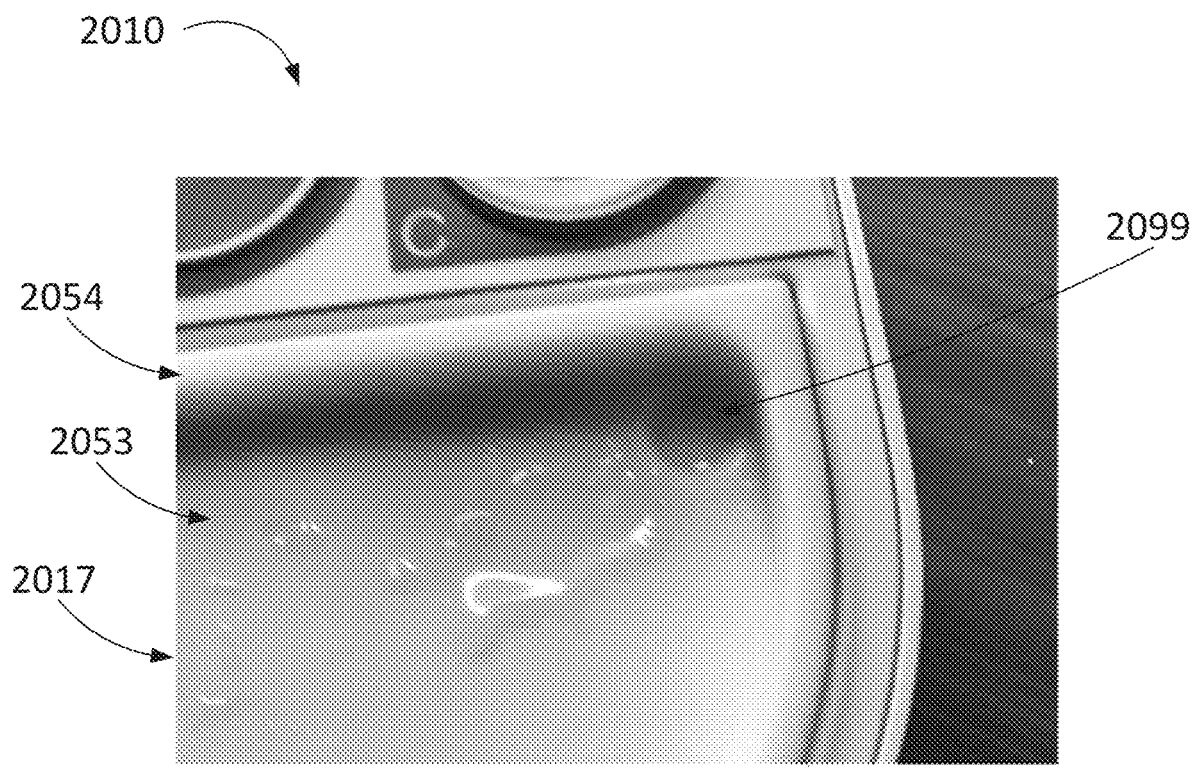
FIG. 59 is a top view of a portion of a device for preparing a cell suspension, according to an embodiment.

FIG. 59 is a top view of a device 2010 for creating a cell suspension. The device 2010 may be the same or similar in structure and/or function to any of the devices described herein. For example, the device 2010 includes a preparation tray 2017. The preparation tray 2017 includes a bottom surface 2053 surrounded by sidewalls 2054. The bottom surface 2053 includes a dimple or cavity 2099 (e.g., a circular collection area) disposed in a corner of the preparation tray 2017 such that fluid may collect in the dimple or cavity 2099 (e.g., if an opposite end of the preparation tray 2017 is tipped upward). Pooling of fluid in the dimple of cavity 2099 may, for example, enable more efficient bulk retrieval of the fluid using a syringe, etc. as described in further detail above. Any of the above-described preparation trays may, in some embodiments, include a similar dimple or cavity in a collection area.

Figure 42:
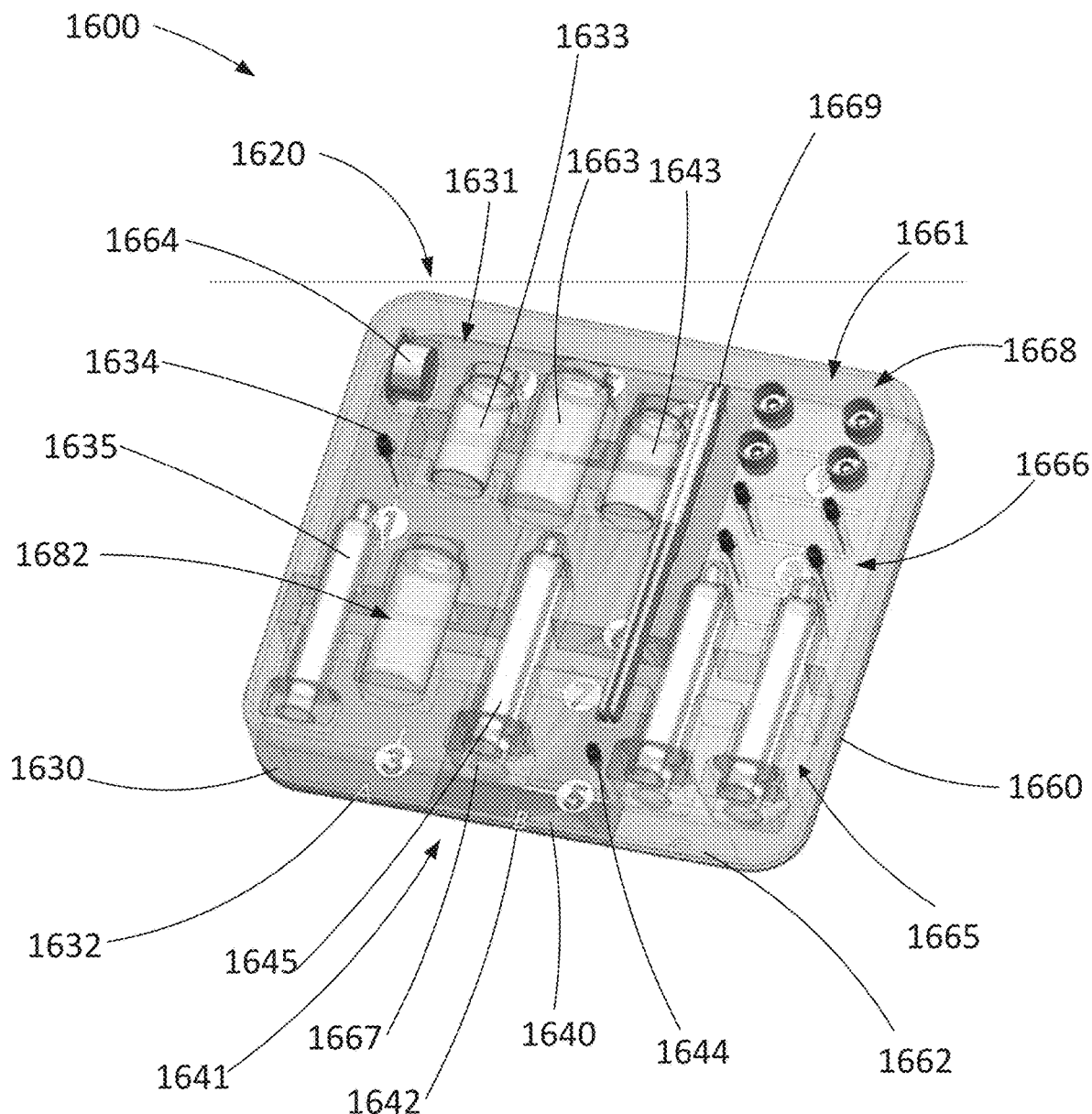
FIG. 42 is a perspective view of a kit for preparing a cell suspension, according to an embodiment.

FIG. 42 is a perspective view of an example embodiment of a kit 1600. The kit 1600 may be the same or similar in structure and/or function to any of the kits described herein. For example, the kit 1600 includes a housing 1620 including a first housing portion 1630, a second housing portion 1640, and a third housing portion 1660. The first housing portion 1630 includes recesses configured to receive a first set of components 1631 associated with a first portion of a tissue processing method, such as any tissue processing method described herein. The second housing portion 1640 includes recesses configured to receive a second set of components 1641 associated with a second portion of the tissue processing method. The third housing portion 1660 includes recesses configured to receive a third set of components 1661 associated with a third portion of the tissue processing method. The first housing portion 1630 includes a first visual indicator 1632 associated with a first label of a device. The device may be the same or similar in structure and/or function to any of the devices described herein. The second housing portion 1640 includes a second visual indicator 1642 associated with a second label of the device. The third housing portion 1660 includes a third visual indicator 1662 associated with a third label of the device.

As shown in FIG. 42, the first housing portion 1630, the second housing portion 1640, and the third housing portion 1660 are integrally formed with each other to form one unitary structure (e.g., a tray). As shown in FIG. 42, the first visual indicator 1632 includes the letter "A", the second visual indicator 1642 includes the letter "B", and the third visual indicator 1662 includes the letter "C". Other kinds of visual indicators (e.g., letter, symbolic, punctuation, textural, etc.) may additionally or alternatively be included on the housing portions. For example, a portion of the housing 1620 may be transparent and the first visual indicator 1632 may include a blue background that may viewed through an upper portion of the housing 1620, the second visual indicator 1642 may include a grey background that may be viewed through an upper portion of the housing 1620, and the third visual indicator 1662 may include a green background that may be viewed through an upper portion of the housing. Additionally, as shown in FIG. 42, one or more of the recesses or cavities configured to receive each of the components of each of the first set of components 1631, the second set of components 1641, and the third set of components 1661 may be identified with a reference numeral corresponding to a particular step of a tissue processing method such that a user may be guided to use (e.g., retrieve and implement) each component in an intended order.

As shown in FIG. 42, the first set of components 1631 includes a vial 1633 containing a volume of water (e.g., sterile water), a needle 1634, an enzyme syringe 1635, and a cell strainer 1664. For example, the enzyme syringe 1635 may be a 10 ml syringe. The needle 1634 is configured to be coupled to the enzyme syringe 1635. The first set of components 1631 optionally also includes an enzyme vial 1682, similar to that described above.

The second set of components 1641 includes a vial 1643 containing a buffer, a needle 1644, a buffer syringe 1645, and an unfiltered suspension syringe 1667. The needle 1644 is configured to be coupled to the buffer syringe 1645. The needle 1644 may be, for example, a blunt fill needle. The second set of components 1641 also includes a pair of scalpels 1669. The second set of components 1641 may also include a vial 1663 containing a buffer similar to that described above. The buffer vial 1663 may include, for example, 30 ml of buffer.

The third set of components 1661 includes a set of skin cell syringes 1665, a set of needles 1666, and a set of spray nozzles 1668. The set of skin cell syringes 1665 may include any suitable number of skin cell syringes, such as four skin cell syringes (e.g., 10 ml syringes). The set of needles 1666 may include any suitable number of needles, such as four needles (e.g., blunt fill needles stacked 2 by 2 in the third housing portion 1660). The set of spray nozzles 1668 may include any suitable number of spray nozzles, such as four spray nozzles. Each needle of the set of needles 1666 may be coupled to a skin cell syringe of the set of skin cell syringes 1665. Additionally, in the alternative to a needle from the set of needles 1666, each spray nozzle of the set of spray nozzles 1668 may be coupled to a skin cell syringe of the set of skin cell syringes 1665.

Figure 43:
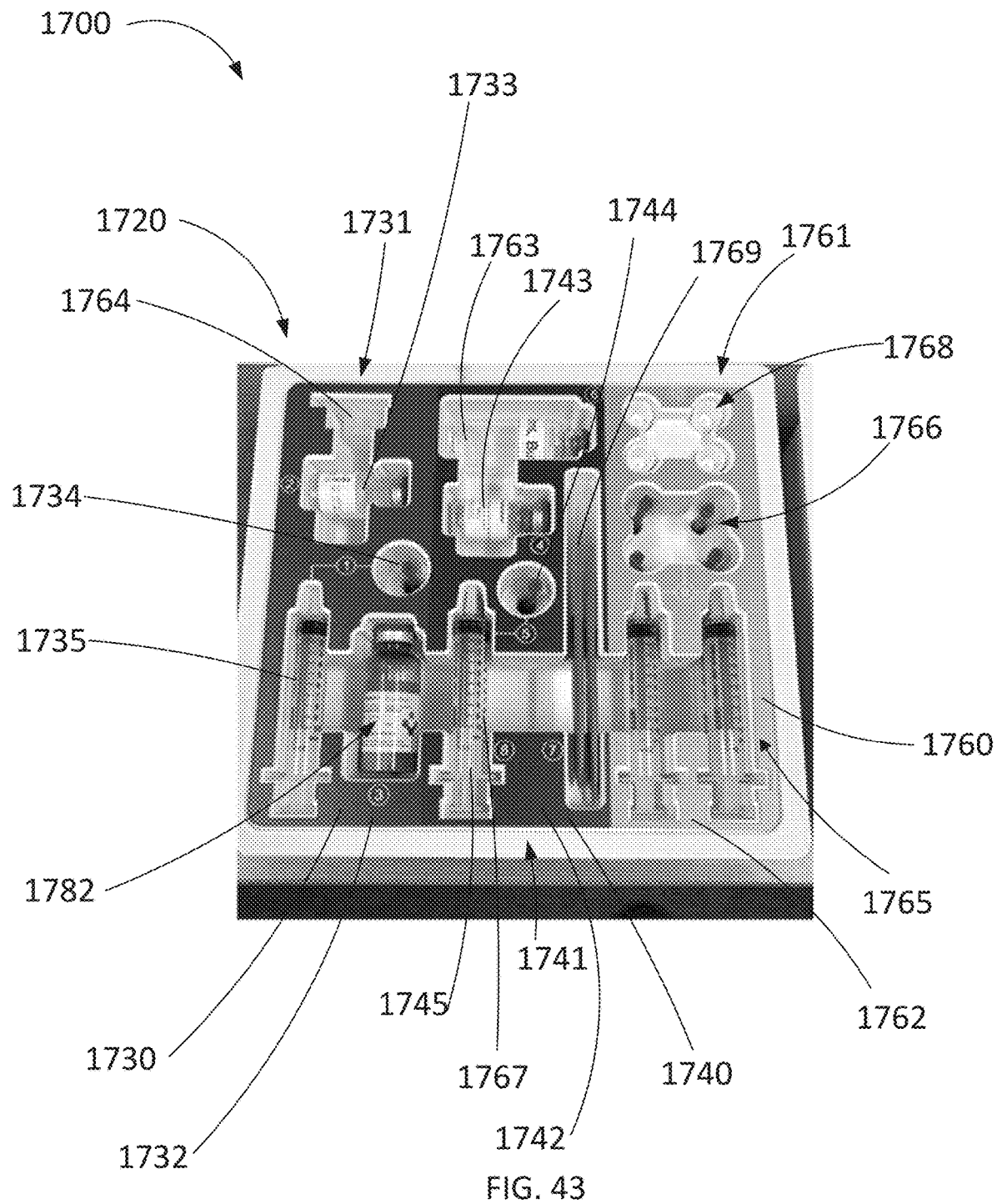
FIG. 43 is a perspective view of a kit for preparing a cell suspension, according to an embodiment.

FIG. 43 is a perspective view of an example embodiment of a kit 1700. The kit 1700 may be the same or similar in structure and/or function to any of the kits described herein. For example, the kit 1700 includes a housing 1720 including a first housing portion 1730, a second housing portion 1740, and a third housing portion 1760. The first housing portion 1730 includes recesses configured to receive a first set of components 1731 associated with a first portion of a tissue processing method, such as any tissue processing method described herein. The second housing portion 1740 includes recesses configured to receive a second set of components 1741 associated with a second portion of the tissue processing method. The third housing portion 1760 includes recesses configured to receive a third set of components 1761 associated with a third portion of the tissue processing method. The first housing portion 1730 includes a first visual indicator 1732 associated with a first label of a device. The device may be the same or similar in structure and/or function to any of the devices described herein. The second housing portion 1740 includes a second visual indicator 1742 associated with a second label of the device. The third housing portion 1760 includes a third visual indicator 1762 associated with a third label of the device.

As shown in FIG. 43, the first housing portion 1730, the second housing portion 1740, and the third housing portion 1760 are integrally formed with each other to form one unitary structure (e.g., a tray). As shown in FIG. 43, the first visual indicator 1732 may include a first color label (e.g., blue) at least partially surrounding the components of the first set of components, the second visual indicator 1742 may include a second color label (e.g., grey) at least partially surrounding the components of the second set of components, and the third visual indicator 1762 may include a third color label (e.g., green) at least partially surrounding the components of the first set of components. Additionally, as shown in FIG. 43, one or more of the recesses or cavities configured to receive each of the components of each of the first set of components 1631, the second set of components 1641, and the third set of components 1661 may be identified with a reference numeral corresponding to a particular step of a tissue processing method such that a user may be guided to use (e.g., retrieve and implement) each component in an intended order.

As shown in FIG. 43, the first set of components 1731 includes a vial 1733 containing a volume of water (e.g., sterile water), a needle 1734, an enzyme syringe 1735, and a cell strainer 1764. For example, the enzyme syringe 1735 may be a 10 ml syringe. The needle 1734 is configured to be coupled to the enzyme syringe 1735. The first set of components 1731 optionally also includes an enzyme vial 1782.

The second set of components 1741 includes a vial 1743 containing a buffer, a needle 1744, a buffer syringe 1745, and an unfiltered suspension syringe 1767. The needle 1744 is configured to be coupled to the buffer syringe 1745. The needle 1744 may be, for example, a blunt fill needle. The second set of components 1741 also includes a pair of scalpels 1769. The second set of components 1741 may also include a vial 1763 containing a buffer. The buffer vial 1763 may include, for example, 30 ml of buffer.

The third set of components 1761 includes a set of skin cell syringes 1765, a set of needles 1766, and a set of spray nozzles 1768. The set of skin cell syringes 1765 may include any suitable number of skin cell syringes, such as four skin cell syringes (e.g., 10 ml syringes). The set of needles 1766 may include any suitable number of needles, such as four needles (e.g., blunt fill needles stacked 2 by 2 in the third housing portion 1760). The set of spray nozzles 1768 may include any suitable number of spray nozzles, such as four spray nozzles. Each needle of the set of needles 1766 may be coupled to a skin cell syringe of the set of skin cell syringes 1765. Additionally, in the alternative to a needle from the set of needles 1766, each spray nozzle of the set of spray nozzles 1768 may be coupled to a skin cell syringe of the set of skin cell syringes 1765.

Figure 44:
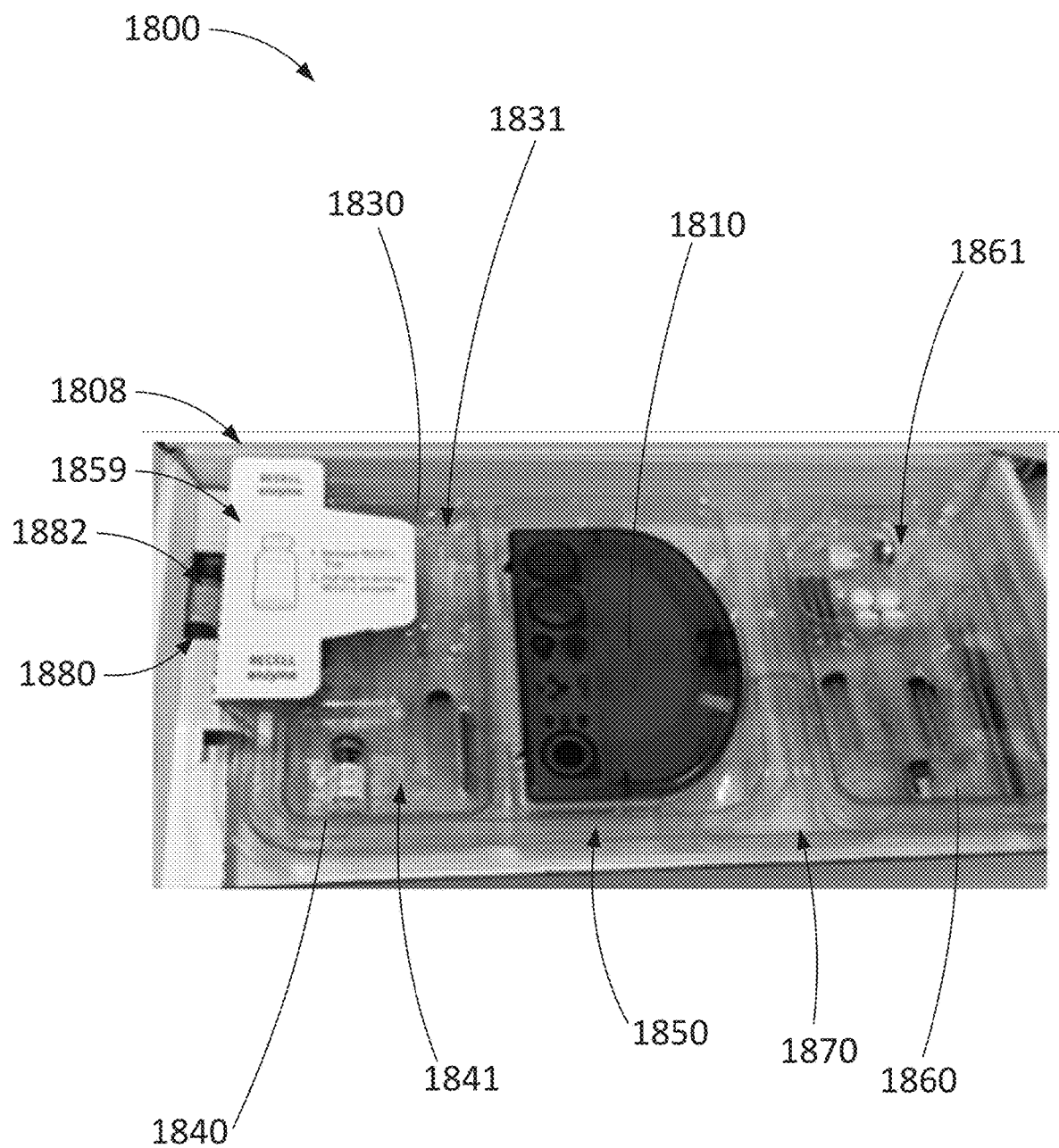
FIG. 44 is a perspective view of a kit for preparing a cell suspension, according to an embodiment.

FIG. 44 is a perspective view of an example embodiment of a kit 1800. The kit 1800 may be the same or similar in structure and/or function to any of the kits described herein. For example, the kit 1800 includes a housing 1820 including a first housing portion 1830, a second housing portion 1840, and a third housing portion 1860. The first housing portion 1830 includes recesses configured to receive a first set of components 1831 associated with a first portion of a tissue processing method, such as any tissue processing method described herein. The second housing portion 1840 includes recesses configured to receive a second set of components 1841 associated with a second portion of the tissue processing method. The third housing portion 1860 includes recesses configured to receive a third set of components 1861 associated with a third portion of the tissue processing method.

The kit 1800 includes a device 1810 that may be the same or similar in structure and/or function to any of the devices described herein. The kit 1800 includes an integrated tray 1850 configured to receive the first housing portion 1830, the second housing portion 1840, and the device 1810. The first housing portion 1830 and the second housing portion 1840 are formed as a unitary tray structure configured to be lifted out of the integrated tray 1850.

The kit 1800 also includes a base 1870 and a box 1808. The base 1870 is configured to receive the integrated tray 1850 and the third housing portion 1860. The box 1808 is configured to receive the base 1870 in a first portion of the box 1808 and is configured to receive an enzyme vial 1882 in an enzyme vial recess 1880 in a second portion of the box 1808. The box 1808 may include a divider 1859 disposed to separate the first portion of the box 1808 from the second portion of the box 1808 such that the sterility of the contents of the base 1870 in the first portion of the box 1808 may be maintained regardless of the sterility of the enzyme vial 1882 or a pouch containing the enzyme vial 1882 in the second portion of the box 1808.

In some implementations, the base 1870 may be formed as a single piece protective packaging layer that includes a pull tab coupled to a removable sealing portion of the base 1870 such that pulling on the pull tab breaks the sealing portion and allows the interior of the base 1870 to be accessed. Additionally, the base 1870, the integrated tray portion 1850, the first housing portion 1830, the second housing portion 1840, and the third housing portion 1860 may each be transparent to allow a user to see the components disposed within the interior of the kit 1800.

Methods of Packaging Kits

FIGS. 45-58 show the steps of packaging a kit or set of kits, such as any of the kits described herein, for shipment. While FIGS. 45-58 depict a method of packaging three kits in a single shipping container, it should be understood that in some embodiments, the method may be modified to package any suitable number of kits (e.g., one, two, four, five, more than five, etc.) in a shipping container. The method illustrated in FIGS. 45-58 may include layering of cold-chain shipping materials to maintain stable temperature of the kits at a desired temperature or temperature range (e.g., between about 20° C. and about 25° C.) for a predetermined period of time, such as up to about 48 hours. Maintaining a stable temperature for the kits within a certain desired temperature range may be important, for example, to avoid compromising the viability or otherwise the chemical state of one or more components of the kit (e.g., enzyme).

Generally, the method of packaging kits (such as any of the kits described herein) may include layering one or more kits between foam inserts and refrigerated brick material, within an insulated container. The container may be insulated, for example, by being at least partially made from insulating material (e.g., insulating foam) and/or having one or more insulating liners or pads. Absorbent wipes may be arranged within the stack-up of packaging materials, such as to help absorb condensation.

Figures 45, 46, 47:
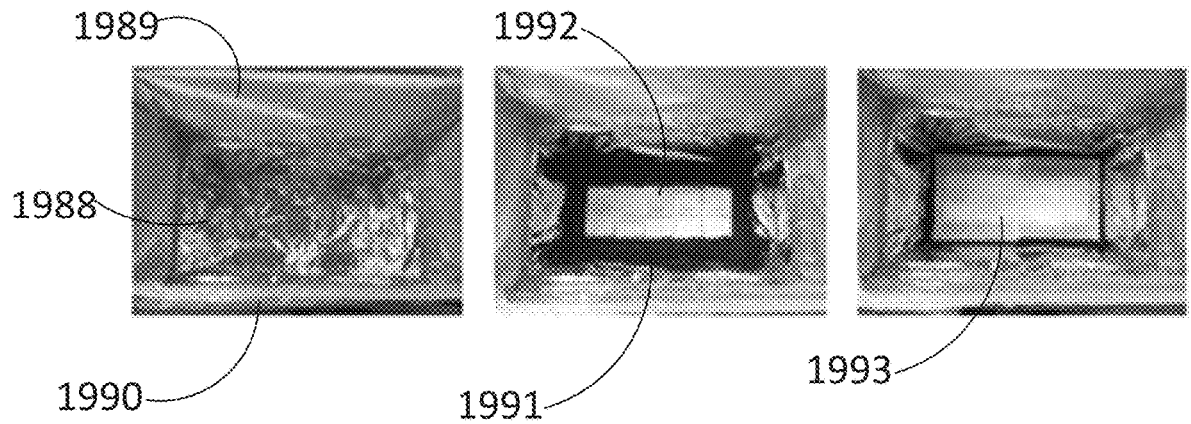
FIGS. 45-58 are images of the steps of packaging a kit for transport, according to an embodiment.

For example, FIG. 45 shows an empty container 1990. The container 1990 may be formed of any suitable material, such as, for example, cardboard, foam, etc. The container 1990 includes insulation 1988 and a liner 1989. As shown in FIG. 46, a first foam insert 1991 may be disposed in the container 1990. The first foam insert 1991 may define a central opening within which a set of refrigerated bricks 1992 (e.g., refrigerated FB24 bricks) may be disposed. For example, a set of five refrigerated bricks 1992 may be disposed in the central opening.

As shown in FIG. 47, absorbent wipes 1993 (e.g., two absorbent wipes) may be disposed on top of the set of refrigerated bricks 1992.

Figures 48, 49, 50:
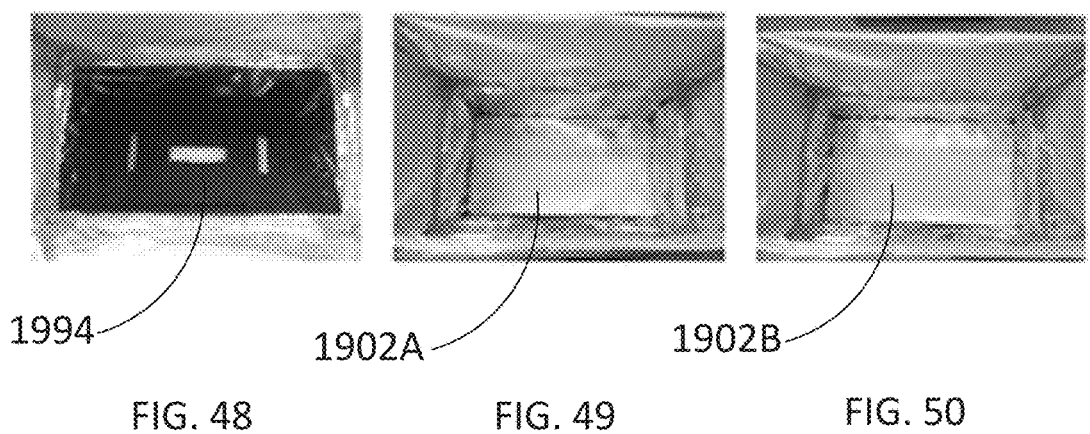

As shown in FIG. 48, a second foam insert 1994 may be disposed in the container 1990 on top of the absorbent wipes 1993

As shown in FIG. 49, a first kit 1902A may be disposed in the container 1990 on top of the second foam insert 1994.

As shown in FIG. 50, a second kit 1902B may be disposed in the container 1990 on top of the first kit 1902A.

Figures 51, 52, 53:
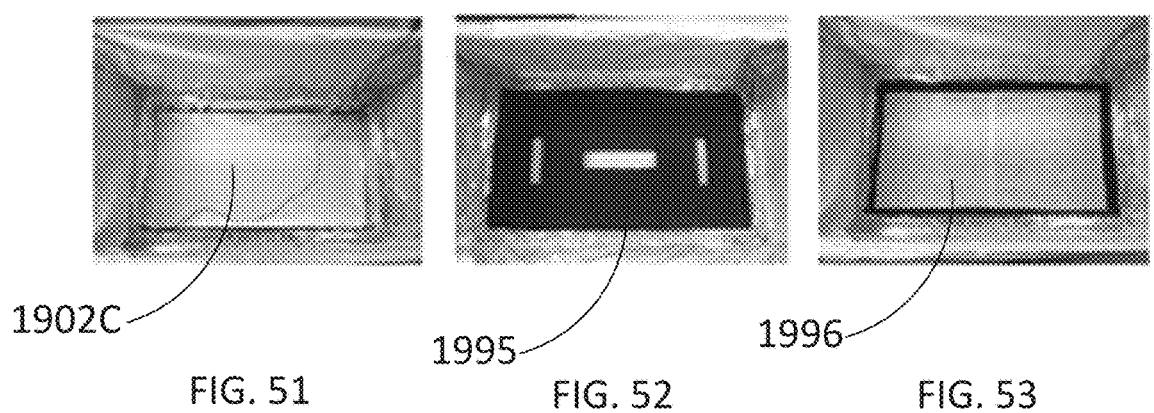

As shown in FIG. 51, a third kit 1902C may be disposed in the container 1990 on top of the second kit 1902B. Additional kits may be similarly arranged on top of the third kit.

As shown in FIG. 52, a third foam insert 1995 may be placed in the container 1990 on top of the third kit 1902C.

As shown in FIG. 53, absorbent wipes 1996 (e.g., two absorbent wipes) may be placed on top of the second foam insert 1995.

Figures 54, 55, 56:
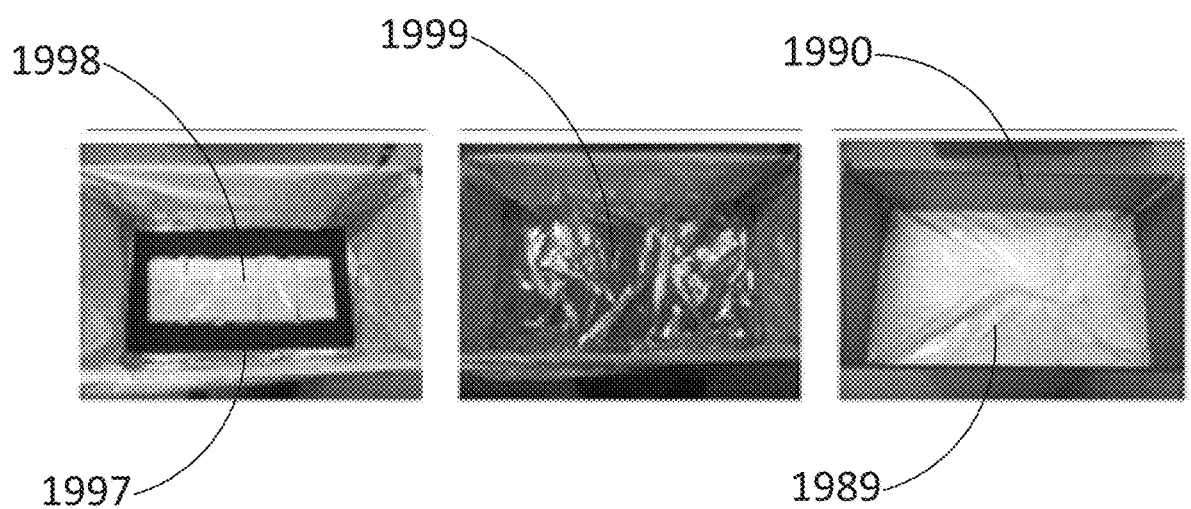

As shown in FIG. 54, a fourth foam insert 1997 may be disposed in the container 1990 on top of the absorbent wipes 1996. The fourth foam insert 1997 may define a central opening within which a set of refrigerated bricks 1998 (e.g., refrigerated FB24 bricks) may be disposed. For example, a set of five refrigerated bricks 1998 may be disposed in the central opening.

As shown in FIG. 55, an insulation pad 1999 (e.g., insulating foam) may be disposed in the container 1990 on top of the fourth foam insert 1997. The insulation pad 1999 may, for example, help create an enclosed space that traps thermal energy inside the container. In some embodiments, the insulation pad 1999 may be sized to fit as closely as possible to the walls of the container so as to reduce escape of thermal energy through gaps or spaces between the insulation pad 1999 and the walls of the container. Additionally or alternatively, the insulating pad may include an insulating foam encased in (e.g., lined with) a metallized foil to further help retain thermal energy inside the container as long as possible.

As shown in FIG. 56, the liner 1989 may be closed to define a closed interior space within the container 1990. The liner 1989 may, for example, function to help bind together the packaging components in a sufficiently tight (snug) manner, thereby reducing undesirable relative shafting of the packaging components. The liner 1989 may additionally or alternatively function to help protect the surrounding container (e.g., cardboard box) from condensation that may otherwise cause the container from degrading and endangering the kit(s) inside. For example, the liner 1989 may include a suitable water-resistant or waterproof layer (e.g., sheet, bag, other cover) such as polyethylene. In some embodiments, multiple liners 1989 (e.g., two or more) may be included in the container 1990 so as to provide extra or redundant protection of the container (or other components vulnerable to moisture) from condensation or other moisture.

Figures 57, 58:
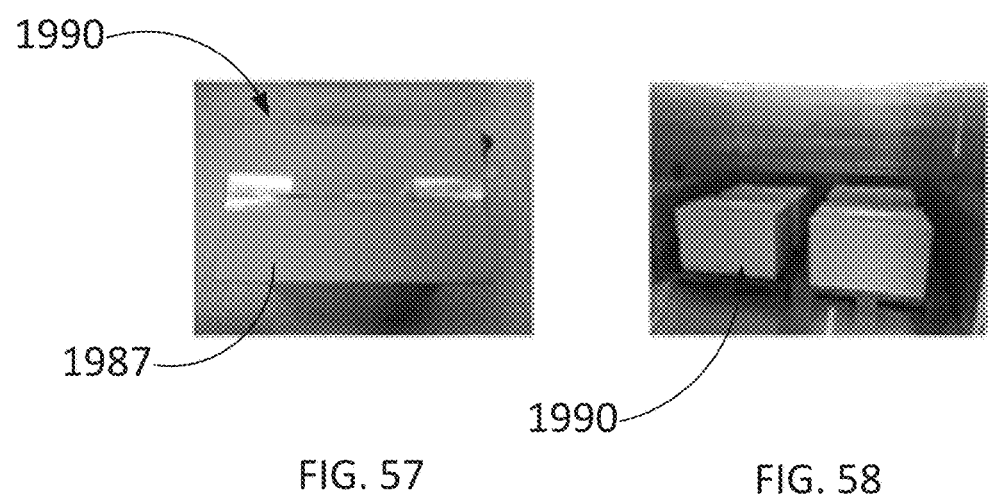

As shown in FIG. 57, flaps 1987 of the container 1990 may be closed and secured to seal the container 1990 (e.g., with tape).

As shown in FIG. 58, the container 1990 may be placed into a chamber with other containers and tested.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they may not be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While specific embodiments of the present disclosure have been outlined above, many alternatives, modifications, and variations will be apparent to those skilled in the art. Accordingly, the embodiments set forth herein are intended to be illustrative, not limiting. Various changes may be made without departing from the spirit and scope of the disclosure. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. A kit for preparing a cell suspension, the kit comprising:
a device defining a first reservoir, a second reservoir, and a third reservoir;
the device including:
(a) a first label identifying the first reservoir configured for use preparing the cell suspension method;
(b) a second label identifying the second reservoir configured for use preparing the cell suspension;
(c) a third label identifying the third reservoir configured for use preparing the cell suspension;
(d) a heating assembly comprising a heating mechanism configured to heat the contents of the first reservoir, wherein the heating assembly is programed to:
(i) illuminate a first visual indicator light during a first time period, the first time period comprising a period of time during which the heating mechanism heats the contents to a target temperature;
(ii) illuminate a second visual indicator light during a second time period, the second time period comprising a period of time during which the heating mechanism maintains the contents at the target temperature, wherein the second time period is at least 15 minutes; and
(iii) automatically cease operating to provide heat to the first reservoir after the second time period;
(e) one or more buttons configured to activate the heating assembly;
(f) one or more heating assembly indicators configured to be associated with indicator lights of the device to indicate one or more statuses of the device;
(g) a preparation tray configured to be used to perform the cell suspension, wherein the preparation tray is removable from a complementary recessed area of the device, wherein the preparation tray comprises one or more collection areas disposed on a bottom surface of the preparation tray, wherein the bottom surface includes a skin tissue manipulation area, wherein the bottom surface is configured such that fluid flows from the skin tissue manipulation area along a transition surface having a slope toward the one or more collection areas, wherein the slope of the transition surface of the preparation tray is between about 0.5 degrees and about 35 degrees, and wherein the preparation tray is half-moon shaped;
(h) a housing configured to receive the device in an integrated tray portion wherein the housing is configured to function as packaging for storage and transport of the device, the housing including:
(i) a first housing portion configured to store a first set of components associated with preparing the cell suspension, wherein the first set of components includes an enzyme vial;
(ii) a the second housing portion configured to store a second set of components associated with preparing the cell suspension, wherein the first housing portion and the second housing portion are removably coupled to each other to form portions of the integrated tray portion;
(iii) a third housing portion configured to store a third set of components associated with preparing cell suspension, wherein the third housing portion is removably coupled to the first housing portion and the second housing portion; and
(iv) a base comprising a first recess configured to receive the integrated tray portion and a second recess configured to receive the third housing portion; and
(v) a box configured to receive the base.

2. The kit of claim 1, wherein the first housing portion is couple to the second housing portion via a perforated connecting portion.

3. The kit of claim 1, wherein the first housing portion includes a recess configured to receive the enzyme vial.

4. The system of claim 1, wherein the first visual indicator and the first label each include a first color, and the second visual indicator and the second label each include a second color.

5. The system of claim 1, wherein the first visual indicator and the first label each include a first letter, and the second visual indicator and the second label each include a second letter.

6. The system of claim 1, wherein the skin tissue manipulation area further comprises a textured surface region.

7. The system of claim 1, wherein the second set of components includes a vial containing a buffer.

8. The kit of claim 1, further comprising a first liner, wherein the first liner includes one or more recesses with a perimeter that matches the shape of the first housing portion.

9. The kit of claim 8, further comprising a second liner, wherein the second liner includes one or more recesses with a perimeter that matches the shape of the second housing portion.

10. The kit of claim 9, further comprising a third liner, wherein the third liner includes one or more recesses with a perimeter that matches the shape of the third housing portion.

11. A packaging system for the device of claim 1 for preparing a cell suspension, the packaging system comprising: a first housing portion defining a set of recesses configured to receive the first set of components associated with the cell suspension, the first housing portion including the first visual indicator associated with the first label of the device; and a second housing portion defining a set of recesses configured to receive a second set of components associated with of the cell suspension, the second housing portion including the second visual indicator associated with the second label of the device.

12. The packaging system of claim 11, wherein the first housing portion is integrally formed with the second housing portion in an integrated tray portion.

13. The packaging system of claim 12, wherein the integrated tray portion comprises a recess configured to receive the device of claim 1.

14. The packaging system of claim 11, wherein the first housing portion is separate from the second housing portion.

15. The packaging system of claim 11, wherein the first housing portion is coupled to the second housing portion via a perforated connecting portion.

16. The packaging system of claim 11, further comprising a base configured to receive the first housing portion and the second housing portion.

17. The packaging system of claim 11, wherein the packaging system further includes a third housing portion configured to store a third set of components associated with the third portion of the cell suspension, the third housing portion including a third visual indicator associated with the third label of the device of claim 1.

18. The packaging system of claim 17, further comprising a base configured to receive the first housing portion, the second housing portion, and the third housing portion.

19. A method for preparing a cell suspension using the device of claim 1 packaged in a housing, comprising:
identifying a first match between the first label disposed proximate the first reservoir of the device and the first visual indicator included in a first housing portion of the housing;
in response to identifying the first match, removing the first set of components from the first housing portion and using the first set of components to perform the cell suspension associated with the first reservoir;
identifying a second match between the second label disposed proximate a second reservoir of the device and the second visual indicator included in a second housing portion of the housing; and
in response to identifying the second match, removing a second set of components from the second housing portion and using the second set of components to perform the cell suspension associated with the second reservoir.

20. The method of claim 19, further comprising: in response to identifying the first match, transferring the first housing portion into a sterile procedure area.

21. The method of claim 19, further comprising: in response to identifying the second match, transferring the second housing portion into a sterile procedure area.

22. The method of claim 19, further comprising: identifying a third match between a third label disposed proximate a third reservoir of the device of claim 1 and a third visual indicator included in a third housing portion of the housing; and in response to identifying the third match, removing a third set of components from the third housing portion and using the third set of components to perform preparing the cell suspension associated with the third reservoir.

23. The method of claim 19, further comprising: performing a tissue manipulation portion of the tissue processing method on a preparation tray of the device.

24. The method of claim 19, wherein the first set of components includes a vial of sterile water, a syringe, and an enzyme vial, the cell suspension associated with the first reservoir including: preparing an enzyme mixture; and delivering the enzyme mixture into the first reservoir.

25. The method of claim 19, further comprising: removing an enzyme vial from a sterile pouch; and disposing the enzyme vial in a recess defined in the first housing portion.

26. The method of claim 19, wherein the second set of components includes a buffer vial and a syringe, the cell suspension associated with the second reservoir including: drawing a volume of the buffer from the buffer vial into the syringe; and delivering the volume of the buffer from the syringe to the second reservoir.

27. The method of claim 20, wherein the third set of components includes a syringe, the cells suspension associated with the third reservoir including: disaggregating a skin sample; creating the cell suspension including cells from the disaggregated skin sample; and drawing the cell suspension into the syringe.

* * * * *